US008633437B2

(12) United States Patent
Dantus et al.

(10) Patent No.: US 8,633,437 B2
(45) Date of Patent: Jan. 21, 2014

(54) ULTRA-FAST LASER SYSTEM

(75) Inventors: Marcos Dantus, Okemos, MI (US); Vadim V. Lozovoy, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1482 days.

(21) Appl. No.: 11/883,703

(22) PCT Filed: Feb. 14, 2006

(86) PCT No.: PCT/US2006/005129
§ 371 (c)(1), (2), (4) Date: Aug. 3, 2007

(87) PCT Pub. No.: WO2006/088841
PCT Pub. Date: Aug. 24, 2006

(65) Prior Publication Data

US 2008/0170218 A1 Jul. 17, 2008

Related U.S. Application Data

(60) Provisional application No. 60/652,772, filed on Feb. 14, 2005.

(51) Int. Cl.
*H01J 49/00* (2006.01)

(52) U.S. Cl.
USPC ............. 250/288; 250/281; 250/282; 372/25; 372/9; 356/301

(58) Field of Classification Search
None
See application file for complete search history.

(56) References Cited

U.S. PATENT DOCUMENTS

| | | | | |
|---|---|---|---|---|
| 3,214,563 | A | 10/1965 | Ford | |
| 3,611,182 | A | 10/1971 | Treacy | |
| 3,919,881 | A | 11/1975 | Metherell | |
| 3,988,704 | A | 10/1976 | Rice et al. | |
| 4,167,662 | A | 9/1979 | Steen | |
| 4,288,691 | A | 9/1981 | Horton | |
| 4,394,780 | A * | 7/1983 | Mooradian | 398/125 |
| 4,477,905 | A | 10/1984 | Sweeney | |
| 4,512,660 | A * | 4/1985 | Goldberg | 356/301 |

(Continued)

FOREIGN PATENT DOCUMENTS

| | | |
|---|---|---|
| EP | 0 605 110 | 7/1994 |
| EP | 1742311 A1 | 1/2007 |

(Continued)

OTHER PUBLICATIONS

Oron et al: "Quantum control of coherent anti-Stokes Raman processes", Physical Review A (Atomic, Molecular, and Optical Physics)APS Through AIP USA, vol. 65, No. 4, Apr. 2002, pp. 043408/1-4, XP002386695 ISSN: 1050-2947.*

(Continued)

*Primary Examiner* — Andrew Smyth
(74) *Attorney, Agent, or Firm* — Harness, Dickey & Pierce, P.L.C.

(57) ABSTRACT

A laser system is provided which selectively excites Raman active vibrations in molecules. In another aspect of the present invention, the system includes a laser, pulse shaper and detection device. A further aspect of the present invention employs a femtosecond laser and binary pulse shaping (BPS). Still another aspect of the present invention uses a laser beam pulse, a pulse shaper and remote sensing.

52 Claims, 8 Drawing Sheets

(56) References Cited

U.S. PATENT DOCUMENTS 4,621,006 A 11/1986 Terry et al.
4,655,547 A 4/1987 Heritage et al.
4,746,193 A 5/1988 Heritage et al.
4,772,854 A 9/1988 Silberberg
4,812,776 A 3/1989 Sasaki
4,819,239 A 4/1989 Sharp et al.
4,834,474 A 5/1989 George et al.
4,853,065 A 8/1989 Terry et al.
4,856,860 A 8/1989 Silberberg et al.
4,866,699 A 9/1989 Brackett et al.
4,913,934 A 4/1990 Sharp et al.
4,928,316 A 5/1990 Heritage et al.
4,999,840 A 3/1991 Negus
5,021,282 A 6/1991 Terry et al.
5,034,613 A 7/1991 Denk et al.
5,048,029 A 9/1991 Skupsky et al.
5,054,027 A 10/1991 Goodberlet et al.
5,077,619 A 12/1991 Toms
5,095,487 A * 3/1992 Meyerhofer et al. ........... 372/23
5,130,994 A 7/1992 Madey et al.
5,132,512 A 7/1992 Sanders et al.
5,132,824 A 7/1992 Patel et al.
5,154,963 A 10/1992 Terry
5,166,818 A 11/1992 Chase et al.
5,235,606 A 8/1993 Mourou et al.
5,239,607 A 8/1993 de Silva et al.
5,341,236 A 8/1994 Stappaerts
5,349,591 A 9/1994 Weston et al.
5,359,410 A 10/1994 Diels et al.
5,400,350 A 3/1995 Galvanauskas
5,406,408 A 4/1995 Ellingson et al.
5,414,540 A 5/1995 Patel et al.
5,414,541 A 5/1995 Patel et al.
5,463,200 A 10/1995 James et al.
5,526,155 A 6/1996 Knox et al.
5,526,171 A 6/1996 Warren
5,530,544 A 6/1996 Trebino et al.
5,541,947 A 7/1996 Mourou et al.
5,572,355 A 11/1996 Cotton et al.
5,585,913 A 12/1996 Hariharan et al.
5,589,955 A 12/1996 Amako et al.
5,615,673 A 4/1997 Berger et al.
5,631,758 A 5/1997 Knox et al.
5,633,885 A 5/1997 Galvanauskas et al.
5,636,050 A 6/1997 Alfano et al.
5,637,966 A 6/1997 Umstadter et al.
5,682,262 A 10/1997 Wefers et al.
5,684,595 A 11/1997 Kato et al.
5,689,361 A 11/1997 Damen et al.
5,704,700 A 1/1998 Kappel et al.
5,719,650 A 2/1998 Wefers et al.
5,726,855 A 3/1998 Mourou et al.
5,734,503 A 3/1998 Szipocs et al.
5,754,292 A 5/1998 Kane et al.
5,759,767 A 6/1998 Lakowicz
5,774,213 A 6/1998 Trebino et al.
5,793,091 A 8/1998 Devoe
5,798,867 A 8/1998 Uchida et al.
5,822,097 A 10/1998 Tournois
5,828,459 A 10/1998 Silberberg
5,832,013 A 11/1998 Yessik et al.
5,854,431 A 12/1998 Linker et al.
5,862,287 A 1/1999 Stock et al.
5,867,304 A 2/1999 Galvanauskas et al.
5,883,309 A 3/1999 Vossiek et al.
5,898,373 A 4/1999 Murad et al.
5,915,268 A 6/1999 Linker et al.
5,936,732 A 8/1999 Smirl et al.
5,956,173 A 9/1999 Svelto et al.
5,956,354 A 9/1999 Yan
5,994,687 A 11/1999 Chanteloup et al.
6,002,480 A * 12/1999 Izatt et al. ..................... 356/479
6,008,899 A 12/1999 Trebino et al.
6,042,603 A 3/2000 Fisher et al.
6,057,919 A 5/2000 Machida et al.
6,058,132 A 5/2000 Iso et al.
6,072,813 A 6/2000 Tournois
6,080,148 A 6/2000 Damasco et al.
6,081,543 A 6/2000 Liu et al.
6,111,251 A 8/2000 Hillenkamp
6,122,419 A 9/2000 Kurokawa et al.
6,130,426 A 10/2000 Laukien et al.
6,156,527 A 12/2000 Schmidt et al.
6,166,385 A 12/2000 Webb et al.
6,178,041 B1 1/2001 Simon
6,181,463 B1 1/2001 Galvanauskas et al.
6,184,490 B1 2/2001 Schweizer
6,191,386 B1 2/2001 Albright et al.
6,198,568 B1 3/2001 Galvanauskas et al.
6,219,142 B1 4/2001 Kane
6,259,104 B1 7/2001 Baer
6,272,156 B1 8/2001 Reed et al.
6,288,782 B1 9/2001 Worster
6,295,860 B1 10/2001 Sakairi et al.
6,296,810 B1 10/2001 Ulmer
6,316,153 B1 11/2001 Goodman
6,327,068 B1 12/2001 Silberberg et al.
6,337,606 B1 1/2002 Brombaugh et al.
6,344,653 B1 2/2002 Webb et al.
6,375,697 B2 4/2002 Davies
6,391,220 B1 5/2002 Zhang et al.
6,396,856 B1 5/2002 Sucha et al.
6,402,898 B1 6/2002 Brumer et al.
6,421,154 B1 7/2002 Diels et al.
6,479,822 B1 * 11/2002 Nelson et al. .............. 250/341.1
6,480,656 B1 11/2002 Islam et al.
6,498,801 B1 12/2002 Dudelzak et al.
6,504,612 B2 1/2003 Trebino
6,515,257 B1 2/2003 Jain et al.
6,539,156 B1 3/2003 Dickson et al.
6,566,667 B1 5/2003 Partlo et al.
6,573,493 B1 6/2003 Futami et al.
6,577,782 B1 6/2003 Leaird et al.
6,603,600 B2 8/2003 Pang
6,610,351 B2 * 8/2003 Shchegolikhin et al. ......... 427/7
6,610,977 B2 8/2003 Megerle
6,621,613 B2 9/2003 Silberberg et al.
6,625,181 B1 9/2003 Oshemkov et al.
6,631,333 B1 10/2003 Lewis et al.
6,642,513 B1 11/2003 Jenkins et al.
6,678,450 B1 1/2004 Franson
6,684,682 B2 2/2004 Stemmle et al.
6,697,196 B2 2/2004 Suzuki
6,708,572 B2 3/2004 Jenkins et al.
6,723,991 B1 4/2004 Sucha et al.
6,753,957 B1 6/2004 Nagli et al.
6,757,463 B2 6/2004 Hutchinson et al.
6,795,456 B2 * 9/2004 Scaggs ............................ 372/23
6,795,777 B1 9/2004 Scully et al.
6,801,318 B2 10/2004 Fu et al.
6,801,551 B1 10/2004 Delfyett et al.
6,804,000 B2 10/2004 Roorda et al.
6,804,045 B2 10/2004 Barty
6,857,744 B2 2/2005 Nakada et al.
6,879,426 B1 4/2005 Weiner
6,885,325 B2 4/2005 Omelyanchouk et al.
6,885,683 B1 4/2005 Fermann et al.
6,914,668 B2 7/2005 Brestel et al.
6,915,040 B2 7/2005 Willner et al.
6,917,631 B2 7/2005 Richardson et al.
6,930,779 B2 8/2005 McGrew
6,963,591 B2 11/2005 Tulloch et al.
7,033,519 B2 4/2006 Taylor et al.
7,049,543 B2 5/2006 Roos et al.
7,057,788 B2 6/2006 Ohbayashi et al.
7,088,435 B2 8/2006 Brestel et al.
7,096,125 B2 8/2006 Padmanabhan et al.
7,105,811 B2 9/2006 Dantus et al.
7,113,327 B2 9/2006 Gu et al.
7,132,223 B2 11/2006 Schroeder et al.
7,169,709 B2 1/2007 Koide
7,170,030 B2 1/2007 Haight et al.
7,170,598 B2 1/2007 Walla et al.
7,224,518 B2 5/2007 Tauser et al.

(56) References Cited

U.S. PATENT DOCUMENTS 7,256,885 B2* 8/2007 Silberberg et al. ............ 356/301
7,276,103 B2 10/2007 Wöste et al.
7,289,203 B2* 10/2007 Frankel ......................... 356/301
7,342,223 B2 3/2008 Ohkubo et al.
7,348,569 B2 3/2008 Feurer et al.
7,391,557 B1 6/2008 Bruch et al.
7,403,281 B2* 7/2008 Carron et al. ................. 356/301
7,403,282 B2 7/2008 Silberberg et al.
7,411,166 B2 8/2008 Wolleschensky et al.
7,439,497 B2 10/2008 Dantus et al.
7,450,618 B2* 11/2008 Dantus et al. ................... 372/25
7,474,467 B2 1/2009 Trebino
7,567,596 B2 7/2009 Dantus et al.
7,576,907 B1 8/2009 Bartels et al.
7,583,710 B2 9/2009 Dantus et al.
7,609,731 B2* 10/2009 Dantus et al. ................... 372/30
7,826,051 B2* 11/2010 Silberberg et al. ............ 356/301
7,973,936 B2 7/2011 Dantus
7,989,731 B2 8/2011 Bischoff et al.
8,208,504 B2 6/2012 Dantus et al.
8,208,505 B2 6/2012 Dantus et al.
8,265,110 B2 9/2012 Dantus et al.
8,300,669 B2 10/2012 Dantus et al.
8,311,069 B2 11/2012 Dantus et al.
2001/0015411 A1 8/2001 Ohdaira et al.
2001/0015990 A1 8/2001 Miyai
2001/0017727 A1 8/2001 Sucha et al.
2002/0025490 A1* 2/2002 Shchegolikhin et al. 430/270.15
2002/0086245 A1 7/2002 Zait et al.
2002/0093653 A1 7/2002 Detalle et al.
2002/0097761 A1 7/2002 Sucha et al.
2002/0176809 A1 11/2002 Siess
2003/0063884 A1* 4/2003 Smith et al. ................... 385/129
2003/0099264 A1* 5/2003 Dantus et al. ................... 372/25
2003/0123051 A1 7/2003 McGrew
2003/0144582 A1 7/2003 Cohen et al.
2003/0194165 A1 10/2003 Silberberg et al.
2003/0210400 A1 11/2003 Joffre et al.
2004/0012837 A1 1/2004 Kaplan et al.
2004/0021243 A1 2/2004 Shih et al.
2004/0031906 A1* 2/2004 Glecker ..................... 250/208.1
2004/0043443 A1 3/2004 Lejeune
2004/0058058 A1* 3/2004 Shchegolikhin et al. ......... 427/7
2004/0089804 A1* 5/2004 Dantus et al. ................. 250/288
2004/0128081 A1* 7/2004 Rabitz et al. .................... 702/23
2004/0145735 A1* 7/2004 Silberberg et al. ............ 356/301
2004/0155184 A1 8/2004 Stockman et al.
2004/0189990 A1 9/2004 Shilling
2004/0233944 A1 11/2004 Dantus et al.
2004/0240037 A1 12/2004 Harter
2004/0259234 A1 12/2004 Chou et al.
2004/0263950 A1 12/2004 Fermann et al.
2005/0017160 A1 1/2005 Wolleschensky et al.
2005/0021243 A1 1/2005 Dantus et al.
2005/0036202 A1 2/2005 Cohen et al.
2005/0103759 A1 5/2005 Li et al.
2005/0155958 A1 7/2005 Arai et al.
2005/0161669 A1* 7/2005 Jovanovich et al. ............ 257/48
2005/0185188 A1 8/2005 McGrew
2005/0226287 A1 10/2005 Shah et al.
2005/0230365 A1 10/2005 Lei et al.
2005/0232313 A1 10/2005 Fermann et al.
2005/0248758 A1* 11/2005 Carron et al. ................. 356/301
2006/0000988 A1* 1/2006 Stuart et al. ............... 250/504 R
2006/0006964 A1 1/2006 Huang et al.
2006/0019171 A1 1/2006 Hosono et al.
2006/0028655 A1 2/2006 Cordingley et al.
2006/0032841 A1 2/2006 Tan et al.
2006/0039419 A1 2/2006 Deshi
2006/0051025 A1 3/2006 Mizuuchi et al.
2006/0056468 A1 3/2006 Dantus et al.
2006/0058683 A1 3/2006 Chance
2006/0066848 A1* 3/2006 Frankel ......................... 356/301
2006/0071803 A1 4/2006 Hamburger et al.
2006/0096426 A1 5/2006 Park
2006/0096962 A1 5/2006 Park
2006/0119743 A1 6/2006 Lin
2006/0120412 A1 6/2006 Liu
2006/0134004 A1* 6/2006 Gellermann et al. .......... 424/9.6
2006/0169677 A1 8/2006 Deshi
2006/0187974 A1 8/2006 Dantus
2006/0207975 A1 9/2006 Ehrmann et al.
2006/0207976 A1 9/2006 Bovatsek et al.
2006/0243712 A1 11/2006 Haight et al.
2006/0274403 A1 12/2006 Kaplan et al.
2006/0285071 A1 12/2006 Erickson et al.
2007/0034615 A1 2/2007 Kleine
2007/0093970 A1 4/2007 Padmanabhan et al.
2007/0103778 A1 5/2007 Kaplan et al.
2008/0309931 A1* 12/2008 Silberberg et al. ............ 356/301
2009/0122819 A1 5/2009 Dantus et al.
2009/0188901 A1 7/2009 Dantus
2009/0207869 A1 8/2009 Dantus et al.
2009/0238222 A1 9/2009 Dantus et al.
2009/0256071 A1 10/2009 Dantus et al.
2009/0257464 A1 10/2009 Dantus et al.
2009/0296744 A1 12/2009 Dantus et al.
2011/0005090 A1 1/2011 Lee et al.

FOREIGN PATENT DOCUMENTS

JP 11095051 A 4/1999
JP 2000055781 A 2/2000
JP 2001337301 A 12/2001
JP 2002139716 A 5/2002
JP 2003 155256 5/2003
WO WO 99/57318 11/1999
WO WO 00/70647 11/2000
WO WO 01/54323 7/2001
WO WO-0231799 A1 4/2002
WO WO 02/061799 8/2002
WO WO-2004023413 A2 3/2004
WO WO 2005/088783 9/2005
WO WO-2005111677 A2 11/2005
WO WO-2006079083 A2 7/2006
WO WO-2006138442 A2 12/2006
WO WO-2007001308 A2 1/2007
WO WO-2007028119 A2 3/2007
WO WO-2007064703 6/2007
WO WO-2007145702 A2 12/2007
WO WO-2008063602 A2 5/2008
WO WO-2009086122 A2 7/2009

OTHER PUBLICATIONS

Weiner et al: "Generation of Terahertz-Rate Trains of Femtosecond Pulses by Phase-Only Filtering" Optics Letters, OSA, Optical Society of America, Washington, DC, US, vol. 15, No. 1, Jan. 1990, pp. 51-53, XP000095196 ISSN: 0146-9592.*

Dong Gun Lee et al., "Coherent Control of High-Order Harmonics with Chirped Femtosecond Laser Pulses"; Physical Review Letters, vol. 87, No. 24, Dec. 10, 2001; pp. 243902-1-243902-4.

M. Armstrong et al., "Versatile seven-femtosecond pulse compressor of parametrically amplified pulses using adaptive optics; studies of the primary events in protein dynamics"; Applied Physics B 74 (Suppl), 2002; pp. S127-S132.

D.S. Chemla et al., "Ultrafast phase dynamics of coherent emission from excitons in GaAs quantum wells"; Physical Review B, vol. 50, No. 12, Sep. 15, 1995; pp. 8439-8453.

Jerome Tignon et al., "Spectral Interferometry of Semiconductor Nanostructures"; IEEE Jounral of Quantum Electronics, vol. 35, vol. 4; Apr. 1999; pp. 510-522.

Arthur L. Smirl et al., "Heavy-Hole and Light-Hole Quantum Beats in the Polarization State of Coherent Emission from Quantum Wells"; IEEE Journal of Quantum Electronics, vol. 35, No. 4; Apr. 1999; pp. 523-531.

John D. Hybl et al., "Two-Dimensional Fourier transform electronic spectroscopy"; Journal of Chemical Physics, vol. 115, No. 14; Oct. 8, 2001; pp. 6606-6622.

C. Iaconis et al., "Direct measurement of the two-point field correlation function"; Optics Letters, vol. 21, No. 21; Nov. 1, 1996; pp. 1783-1785.

(56) References Cited

OTHER PUBLICATIONS

A.M. Weiner et al., "Femtosecond Pulse Sequences Used for Optical Manipulation of Molecular Motion", Reports; Mar. 16, 1990; pp. 1317-1319.
Ch. Warmuth et al., "Studying vibrational wavepacket dynamics by measuring fluorescence interference fluctuations"; Journal of Chemical Physics, vol. 112, No. 11; Mar. 15, 2000; pp. 5060-5069.
Ch. Warmuth et al., "Molecular quantum dynamics in a thermal system; fractional wave packet revivals probed by random-phase fluorescence interferometry"; Journal of Chemical Physics, vol. 114, No. 22; Jun. 8, 2001; pp. 9901-9910.
G.G. Paulus et al., "Absolute-phase phenomena in photoionization with few-cycle laser pulses"; Nature, vol. 414; Nov. 8, 2001; pp. 182-184.
Yaron Silberberg, "Physics at the attosecond frontier"; Nature, vol. 414, Nov. 29, 2001; pp. 494-495.
M. Hentschel et al., "Attosecond metrology"; Nature, vol. 414; Nov. 29, 2001; pp. 509-513.
L. Lepetit et al., "Linear techniques of phase measurement by femtosecond spectral interferometry for applications in spectroscopy"; J. Opt. Soc. Am. B., vol. 12, No. 12; Dec. 1995; pp. 2467-2474.
L. Lepetit et al., "Two-dimensional nonlinear optics using Fourier-transform spectral interferometry"; Optics Letters, vol. 21, No. 8; Apr. 15, 1996; pp. 564-566.
K.C. Chu et al., "Temporal interferometric measurement of femtosecond spectral phase"; Optics Letters, vol. 21, No. 22; Nov. 15, 1996; pp. 1842-1844.
W.J. Walecki et al., "Characterization of the polarization state of weak ultrashort coherent signals by dual-channel spectral interferometry"; Optics Letters, vol. 22, No. 2; Jan. 15, 1997; pp. 81-83.
J.P. Likforman et al., "Measurement of photon echoes by use of femtosecond Fourier-transform Spectral Interferometry"; Optics Letters, vol. 22, No. 14; Jul. 15, 1997; pp. 1104-1106.
Michel F. Emde et al, "Spectral Interferometry as an alternative to time-domain heterodyning"; Optics Letters, vol. 11, vol. 17; Sep. 1, 1997; pp. 1338-1340.
X. Chen et al., "Temporally and spectrally resolved amplitude and phase of coherent fourwave-mixing emission from GaAs quantum wells"; Physical Review B, vol. 56, No. 15; Oct. 15, 1997; pp. 9738-9743.
Christophe Dorrer, "Influence of the calibration of the detector on spectral interferometry", J. Opt. Soc. Am. B; vol. 16, No. 7; Jul. 1999; pp. 1160-1168.
Allison W. Albrecht et al., "Experimental distinction between phase shifts and time delays: Implications for femtosecond spectroscopy and coherent control of chemical reactions"; Journal of Chemical Physics, vol. 111, No. 24; Dec. 22, 1999; pp. 10934-10955.
Christophe Dorrer et al., "Spectral resolution and sampling issues in Fourier-transform spectral interferometry"; J. Opt. Soc. Am. B, vol. 17, No. 10; Oct. 2000; pp. 1795-1802.
G. Roberts; "Abstract-Interference effects in femtosecond spectroscopy"; Philosophical Transactions of the Royal Society of London Series A—Mathematical Physical and Engineering Sciences; 360 (1794); 987-1021; May 15, 2002 (1 page).
B. Chatel et al., "Role of quadratic and cubic spectral phases in ladder climbing with ultrashort pulses"; Physical Review A 70; 2004; pp. 053414-1-053414-10.
Richard S. Judson et al., "Teaching Lasers to Control Molecules", Physical Review Letters, vol. 68, No. 10; Mar. 9, 1992; pp. 1500-1503.
Michael Messina et al., "Quantum control of multidimensional systems: Implementation within the time-dependent Hartree approximation"; J. Chem Phys. 104; Jan. 1996; pp. 173-182.
D.H. Schirrmeister et al., "Femtosecond pulse dependence of dissipation in molecular systems"; Chemical Physics Letters Dec. 4, 1998; pp. 383-390.
Herschel Rabitz et al., "Optimal Control of Molecular Motion: Design, Implementation and Inversion", Acc. Chem. Res., vol. 33, No. 8; 2000; pp. 572-578.
R. deVivie-Riedle et al., "Design and interpretation of laser pulses for the control of quantum systems"; Applied Physics B; 2000; pp. 285-292.
Moshe Shapiro et al., "On the Origin of Pulse Shaping Control of Molecular Dynamics"; J. Phys. Chem. A, vol. 105, No. 105; 2001; pp. 2897-2902.
Y.J. Yan et al., "Pulse shaping and coherent Raman spectroscopy in condensed phases"; J. Chem. Phys 94 (2); Jan. 15, 1991; pp. 997-1001.
Bern Kohler et al., "Mode-Locking Matter with Light", J. Phys. Chem 1993, 97; pp. 12602-12608.
Jeffrey L. Krause et al., "Optical control of molecular dynamics; Molecular cannons, reflectrons and wave-packet focusers"; J. Chem. Phys. 99(9); Nov. 1, 1993; pp. 6562-6578.
V. Engel et al., "Two-photon wave-packet interferometry", J. Chem Phys. 100 (8); Apr. 15, 1994; pp. 5448-5458.
Jeffrey L. Krause et al., "Quantum Control of Molecular Dynamics: The Strong Response Regime"; J. Phys. Chem; 1995; 99; pp. 13736-13747.
Jianwei Che et al., "Detection and Control of Molecular Quantum Dynamics"; J. Phys. Chem.; 1995; pp. 14949-14958.
M. Sterling et al., "Interrogation and control of condensed phase chemical dynamics with linearly chirped pulses: I2 in solid Kr"; J. Chem. Phys. 104; May 1, 1996; pp. 6497-6506.
Jianwei Che et al., "Semiclassical Dynamics and Quantum Control in Condensed Phases: Application to I2 in a Solid Argon Matrix"; J. Phys. Chem. 1996, 100; pp. 7873-7883.
Jianshu Cao et al., "A simple physical picture for quantum control of wave packed localization"; J. Chem Phys., 107; Aug. 1, 1997; pp. 1441-1450.
Kenji Mishima et al., "A theoretical study on laser control of a molecular nonadiabatic process by ultrashort chirped laser pulses"; Journal of Chemical Physics, vol. 109, No. 5; Aug. 1, 1998; pp. 1801-1809.
H.A. Kim et al., "Expanded concept of the adiabatic population transfer using dressed states"; Physical Revaiew A, vol. 59, No. 2; Feb. 1999; pp. 1404-1407.
Jianshu Cao et al.; "Molecular pie pulses: Population inversion with positively chirped short pulses"; Journal of Chemical Physics, vol. 113, No. 5; Aug. 1, 2000; pp. 1898-1909.
A.J. Wurzer et al.; "Highly localized vibronic wavepackets in large reactive molecules"; Appl. Phys. B 71, 2000; pp. 405-409.
F. Legare et al.; "Laser pulse control of Raman processes by chirped non-adiabatic passage"; Journal of Raman Spectroscopy; 2000; pp. 15-23.
Moshe Shapiro et al.; "Coherently Controlled Asymmetric Synthesis with Achiral Light"; Physical Review Letters, vol. 84, No. 8; Feb. 21, 2000; pp. 1669-1672.
Gabriel Turinici et al.; "Quantum wavefunction controllability"; Chemical Physics 267; 2001; pp. 1-9.
M. Gruebele; "Fully quantum coherent control"; Chemical Physics 267; 2001; pp. 33-46.
V.S. Malinovsky et al.; "General theory of population transfer by adiabatic rapid passage with intense, chirped laser pulses"; The European Physical Journal D 14; 2001; pp. 147-155.
Z.W. Shen et al.; "Selective preparation of ground state wave-packets: a theoretical analysis of femtosecond pump-dump-probe experiments on the potassium dimer"; The European Physical Journal D 14; 2001; pp. 167-172.
Sanislav S. Bychkov et al.; "Laser coherent control of molecular chiral states via entanglement of the rotational and torsional degrees of freedom"; Journal of Raman Spectroscopy; 2002; 33: pp. 962-973.
S.E. Harris; "Control of Feshbach resonances by quantum interference"; Physical Review A66; 2002; pp. 010701-1-010701-4.
John M. Jean et al.; "Application of a multilevel Redfield theory to electron transfer in condensed phases"; J. Chem. Phys. 96; No. 8; Apr. 15, 1992; pp. 5827-5842.

(56) References Cited

OTHER PUBLICATIONS

Bjarne Amstrup et al.; "Control of HOD photodissociation dynamics via bond-selective infrared multiphoton excitation and a femtosecond ultraviolet laser pulse"; J. Chem. Phys., vol. 97, No. 11; Dec. 1, 1992; pp. 8285-8295.
L.D. Ziegler et al.; "Nonlinear polarization description of phase-locked pulse-pair spectroscopy"; J. Chem. Phys., vol. 97, No. 7; Oct. 1, 1992; pp. 4704-4713.
S. Meyer et al.; "Photoelectron distributions from femtosecond pump/probe excitation with chirped probe pulses"; Journal of Chemical Physics, vol. 108, No. 18; pp. 7631-7636.
V.M. Akulin et al.; "Laser Control of Atomic Motion inside Diatomic Molecules"; J. Phys. Chem. A, vol. 102, No. 23; 1998; pp. 4310-4320.
Jianshu Cao et al.; "Molecular Pi PUIse for Total Inversion of Electronic State Population"; Physical Review Letters, vol. 80, No. 7; Feb. 16, 1998; pp. 1406-1409.
Moshe Shapiro et al.; "Nonadiabatic wave packet dynamics: Experiment and theory in IBr"; Jornal of Chemical Physics, vol. 110, No. 5; Feb. 1, 1999; pp. 2465-2473.
Zhenwen Shen et al.; "Pump-dump control and the related transient absorption spectroscopies"; Journal of Chemical Physics, vol. 110, No. 15; Apr. 15, 1999; pp. 7192-7201.
Kenji Mishima et al.; "Theoretical study on quantum control of photodissociation and photodesorption dynamics by femtosecond chirped laser pulses"; Journal of Chemical Physics, vol. 110, No. 16; Apr. 22, 1999; pp. 7756-7769.
H.S. Moon et al.; "Coherence control using the ratio of Rabi frequencies for complete coherent inversion in a four-level system"; J. Phys. B vol. 32; 1999; pp. 987-999.
Jeffrey A. Cina; "Nonlinear wavepacket interferometry for polyatomic molecules"; Journal of Chemical Physics, vol. 113, No. 21; Dec. 1, 2000; pp. 9488-9496.
F. Gelmukhanov et al.; "Dynamics of two-photon absorption by molecules and solutions"; J. Opt. Soc. Am. B, vol. 19, No. 5; May 2002; pp. 937-945.
Philip H. Bucksbaum; "Ultrafast control"; Nature magazine, vol. 421; Feb. 6, 2003; Kuhn & Weyn SR2 Sep. 4, 2001; pp. 593-594.
Christopher J. Bardeen et al.; "Effect of Pulse Shape on the Efficiency of Multiphoton Processes: Implications for Biological Microscopy"; Journal of Biomedical Optics, vol. 4, No. 3; Jul. 1999; pp. 362-367.
T. Hornung et al.; "Optimal control of one and two-photon transitions with shaped femtosecond pulses and feedback"; Applied Physics B 71; 2000; pp. 277-284.
T. Brixner et al.; "Photoselective adaptive femtosecond quantum control in the liquid phase"; Nature magazine, vol. 414; Nov. 2001; pp. 57-60.
B.J. Pearson et al.; "Coherent control using adaptive learning algorithms"; Physical Review A, vol. 63; 2001; pp. 063412-1-063412-12.
Jennifer L. Herek et al.; "Quantum control of energy flow in light harvesting"; Nature magazine, vol. 417; May 30, 2002; pp. 533-535.
Nirit Dudovich et al.; "Single-pulse coherently controlled nonlinear Raman spectroscopy and microscopy"; Nature magazine, vol. 418; Aug. 1, 2002; pp. 512-514.
Dan Oron et al.; "Single-Pulse Phase-Contrast Nonlinear Raman Spectroscopy"; Physical Review Letters, vol. 89, No. 27; Dec. 30, 2002; pp. 27300-1-273001-4.
T. Brixner et al.; "Liquid-phase adaptive femtosecond quantum control; Removing intrinsic intensity dependencies"; Journal of Chemical Physics, vol. 118, No. 8; Feb. 22, 2003; pp. 3692-3701.
R. Netz et al.; "Observation of Selectivity of Coherent Population Transfer Induced by Optical Interference"; Physical Review Letters, vol. 90, No. 6; Feb. 14, 2003; pp. 063001-1-063001-4.
D.W. Schumacher et al.; "Phase Dependence of Intense-Field Ionization"; Physical Review A, vol. 54, No. 5; Nov. 1996; pp. 4271-4278.
Christopher J. Bardeen et al.; "Feedback quantum control of molecular electronic population transfer"; Chemical Physics Letters 280; 1997; pp. 151-158.
Christopher J. Bardeen et al.; "Quantum Control of Population Transfer in Green Fluorescent Protein by Using Chirped Femtosecond Pulses"; J. Am. Chem. Soc., vol. 120, No. 50; 1998; 13023-13027.
Doron Meshulach et al.; "Coherent quantum control of two-photon transitions by a femtosecond laser pulse"; Nature magazine, vol. 396; Nov. 19, 1998; pp. 239-242.
A. Baltuska et al.; "Attosecond control of electronic processes by intense light fields"; Nature magazine, vol. 421; Feb. 6, 2003; pp. 611-615.
D.J. Maas et al.; "Population transfer via adiabatic passage in the rubidium quantum ladder system"; Physical Review A, vol. 59, No. 2; Feb. 1999; pp. 1374-1381.
Zohar Amitary et al.; "Phase-tailoring molecular wave packets to time shift their dynamics"; Chemical Physics 267; 2001; pp. 141-149.
T.C. Weinacht et al.; "Coherent learning control of vibrational motion in room temperature molecular gases"; Chemical Physics Letters 344; 2001; pp. 333-338.
R. van Leeuwen et al.; "Manipulation of differential electron yields via autoionizing wave-packet control"; Physical Review A, vol. 63; 2001; pp. 033403-1-033403-5.
Dan Oron et al.; "Quantum control of coherent anti-Stokes Raman processes"; Physical Review A, vol. 65; 2002; pp. 043408-1-043408-4.
Nirit Dudovich et al.; "Coherent Transient Enhancement of Optically Induced Resonant Transitions"; Physical Review Letters, vol. 88, No. 12; Mar. 25, 2002; pp. 123004-1-123004-4.
Jerome Degert et al.; Realization of a Time-Domain Fresnel Lense with Coherent Control; Physical Review Letters, vol. 89, No. 20; Nov. 11, 2002; pp. 203003-1-203003-4.
M. Wollenhaupt et al.; "Interferences of Ultrashort Free Electron Wave Packets"; Physical Review Letters, vol. 89, No. 17; Oct. 21, 2002; pp. 173001-1-173001-4.
R.R. Jones; "Multiphoton Ionization Enhancement Using Two Phase-Coherent Laser Pulses"; Physical Review Letters, vol. 75, No. 8; Aug. 21, 1995; pp. 1491-1494.
D.J. Maas et al.; "Vibrational ladder climbing in NO by ultrashort infrared laser pulses"; Chemical Physics Letters 270; May 16, 1997; pp. 45-49.
Christopher J. Bardeen et al.; "Quantum control of I2 in the gas phase and in condensed phase solid Kr matrix"; J. Chem. Phys., vol. 106, No. 20; May 22, 1997; pp. 8486-8503.
D.J. Maas et al.; Vibrational ladder climbing in NO by (sub)picosecond frequency-chirped infrared laser pulses; Chemical Physics Letters 290; 1998; pp. 75-80.
Vladislave V. Yakovlev et al.; "Chirped pulse enhancement of multiphoton absorption in molecular iodine"; Journal of Chemical Physics, vol. 108, No. 6, Feb. 8, 1998; pp. 2309-2313.
Radoslaw Uberna et al.; "Phase and amplitude control in the formation and detection of rotational wave packets in the E1E+g state of Li2"; Journal of Chemical Physics, vol. 108, No. 22; pp. 9259-9274.
John M. Papanikolas et al.; "Erratum: Manipulation of rovibrational wave packet compostiion in the Li2 E(Eg) shelf state using intermediate state selection and shaped femtosecond laser pulses"; J. Chem Phys. 107, 4172; 1997; p. 10830.
T.C. Weinacht et al.; "Measurement of the Amplitude and Phase of a Sculpted Rydberg Wave Pocket"; Physical Review Letters; vol. 80, No. 25; Jun. 22, 1998; pp. 5508-5511.
Radoslaw Uberna et al.; "Phased control of wavepacket dynamics using shape femtosecond pulses"; Faraday Discuss, vol. 113; 1999; pp. 385-400.
T.C. Weinacht et al.; "Toward Strong Field Mode-Selective Chemistry"; J. Phys. Chem. A, vol. 103, No. 49; 1999; pp. 10166-10168.
Mohamed Aziz Bouchene et al.; "Wavepacket interferometry with chirped pulses"; J. Phys. B; 1999; pp. 5167-5177.
D.J. Maas et al.; "Rotational interference in vibrational ladder climbing in NO by chirped infrared laser pulses"; Physical Review A, vol. 60, No. 2; Aug. 1999; pp. 1351-1362.
R. van Leeuwen et al.; "Coherent Control of the Energy and Angular Distribution of Autoionized Electrons"; Physical Review Letters, vol. 82, No. 14; Apr. 5, 1999; pp. 2852-2855.

(56) References Cited

OTHER PUBLICATIONS

Celine Nicole et al.; "Saturation of wave-packet interferences: Direct observation of spin precession in potassium atoms"; Physical Review A, vol. 60, No. 3; Sep. 1999; pp. R1755-R1758.
Mohamed Aziz Bouchene et al.; "Interplay between wave packet interferences and second harmonic generation"; Optics Communications 181; 2000; pp. 327-336.
Radoslaw Uberna et al.; "Ultrafast spectroscopy of wavelength-dependent coherent photoionization cross sections of Li2 wave packets in the E1Eg state: The role of Rydberg states"; Journal of Chemical Physics, vol. 114, No. 23; Jun. 15, 2001; pp. 10311-10320.
Lorenzo Pesce et al.; "Quantum dynamics simulation of the ultrafast photoionization of Li2"; Journal of Chemical Physics, vol. 114, No. 3; Jan. 15, 2001; pp. 1259-1271.
M.F. DeCamp et al.; "Dynamics and coherent control of high-amplitude optical phonons in bismuth"; Physical Review B, vol. 64; 2001; pp. 092301-1-092301-3.
J. Ahn et al.; "Quantum Phase Retrieval of a Rydberg Wave Packet Using a Half-Cycle Pulse"; Physical Review Letters, vol. 86, No. 7; Feb. 12, 2001; pp. 1179-1182.
Sebastien Zamith et al.; "Observation of Coherent Transients in Ultrashort Chirped Excitation of an Undamped Two-Level System"; Physical Review Letters, vol. 87, No. 3; Jul. 16, 2001; pp. 033001-1-033001-4.
Hans U. Stauffer et al.; "Simultaneous phase control of Li2 wave packets in two electronic states"; Journal of Chemical Physics, vol. 116, No. 3; Jan. 15, 2002; pp. 946-954.
Joshua B. Ballard et al.; "Optimization of wave packet coefficients in Li 2 using an evolutionary algorithm: The role of resonant and nonresonant wavelengths"; Journal of Chemical Physics, vol. 116, No. 4; Jan. 22, 2002; pp. 1350-1360.
Elizabeth Mirowski et al.; "Effect of nonresonant frequencies on the enhancement of quantum beat amplitudes in rovibrational states of Li2: The role of state spacing"; Journal of Chemical Physics, vol. 117, No. 24; Dec. 22, 2002; pp. 11228-11238.
S.N. Pisharody et al.; "Phase-controlled stair-step decay of autoionizing radial wave packets"; Physical Review A, vol. 65; 2002; pp. 033418-1-033418-10.
R. Netz et al.; "Coherent population dynamics of a three-level atom in spacetime"; Physical Review A, vol. 65; pp. 043406-1-043406-12.
Joshua B. Ballard et al.; "Simultaneous control of time-dependent population transfer dynamics and wave-packet quantum interferences in Li2 by shaped ultrafast pulses"; Physical Review A 66; 2002; pp. 043402-1-043402-7.
Dan Oron et al.; "Narrow-Band Coherent Anti-Stokes Raman Signals from Broad-Band Pulses"; Physical Review Letters, vol. 88, No. 6; Feb. 11, 2002; pp. 063004-1-063004-4.
M.M. Salour et al.; "Observation of Ramsey's Interference Fringes in the Profile of Doppler-Free Two-Photon Resonances"; Physical Review Letters, vol. 38, No. 14; Apr. 4, 1977; pp. 757-760.
N.F. Scherer et al.; "Time resolved dynamics of isolated molecular systems studied with phase-locked femtosecond pulse pairs"; J. Chem Phys. vol. 93, No. 1; Jul. 1, 1990; pp. 856-857.
J.S. Melinger et al.; "Adiabatic population inversion in 12 vapor with picosecond laser pulses"; J. Chem. Phys. vol. 95, No. 3; Aug. 1, 1991; pp. 2210-2213.
J.J. Gerdy et al.; "Femtosecond selective control of wave packet population"; Chemical Physics Letters, vol. 171, No. 1/2; Jul. 27, 1990; pp. 1-4.
Norbert F. Scherer et al.; "Fluorescence-detected wave packet interferometry: Time resolved molecular spectroscopy with sequences of femtosecond phase-locked pulses"; J. Chem. Phys., vol. 95, No. 3; Aug. 1, 1991; pp. 1487-1511.
N.F. Scherer et al.; "Fluorescence-detected wave packet interferometry. II. Role of rotations and determination of the susceptibility"; J. Chem. Phys., vol. 96, No. 6; Mar. 15, 1992; pp. 4180-4194.
L.D. Noordam et al.; "Redistribution of Rydberg States by Intense Picosecond Pulses"; Physical Review Letters, vol. 68, No. 10; Mar. 9, 1992; pp. 1496-1499.
J.S. Melinger et al.; "Generation of Narrowband Inversion with Broadband Laser Pulses"; vol. 68, No. 13; Mar. 30, 1992; pp. 2000-2003.
B. Broers et al.; "Efficient Population Transfer in a Three-Level Ladder System by Frequency-Swept Ultrashort Laser Pulses"; Physical Review Letters, vol. 69, No. 14; Oct. 5, 1992; pp. 2062-2065.
R.R. Jones et al.; "Ramsey Interference in Strongly Driven Rydberg Systems"; Physical Review Letters, vol. 71, No. 16; Oct. 18, 1993; pp. 2575-2578.
J.F. Christian et al.; "Rubidium electronic wavepackets probed by a phase-sensitive pump-probe technique"; Optics Communications, vol. 103, No. 1/2; Nov. 1, 1993; pp. 79-84.
J.S. Melinger et al.; "Adiabatic population transfer with frequency-swept laser pulses"; J. Chem. Phys. vol. 101, No. 8; Oct. 15, 1994; pp. 6439-6454.
P. Balling et al.; "Interference in climbing a quantum ladder system with frequency-chirped laser pulses"; Physical Review A, vol. 50, No. 5; Nov. 1994; pp. 4276-4285.
D.W. Schumacher et al.; "Phase Dependence of Intense Field Ionization: A Study Using Two Colors"; Physical Review Letters, vol. 73, No. 10; Sep. 5, 1994; pp. 1344-1347.
L. Marmet et al.; "Observation of Quasi-Landau Wave Packets"; Physical Review Letters, vol. 72, No. 24; Jun. 13, 1994; pp. 3779-3782.
Valerie Blanchet et al.; "One-color coherent control in Cs2 Observation of 2.7 fs beats in the ionization signal"; Chemical Physics Letters, vol. 233; Feb. 25, 1995; pp. 491-499.
R.R. Jones et al.; "Bound-state interferometry using incoherent light"; J. Phys. B 28; 1995; pp. L405-L411.
D.W. Schumacher et al.; "Programmable cesium Rydberg wave packets"; Physical Review A, vol. 52, No. 6; Dec. 1995; pp. 4719-4726.
R.R. Jones; "Interference Effects in the Multiphoton Ionization of Sodium"; Physical Review Letters, vol. 74, No. 7; Feb. 13, 1995; pp. 1091-1094.
Bern Kohler et al.; "Quantum Control of Wave Packet Evolution with Tailored Femtosecond Pulses"; Physical Review Letters, vol. 74, No. 17; Apr. 24, 1995; pp. 3360-3363.
M. Ovchinnikov et al.; "Quantum interference in resonant Raman spectra of I2 in condensed media"; J. Chem. Phys., vol. 106, No. 13; Apr. 1, 1997; pp. 5775-5778.
Richard M. Williams et al.; "Compositional control of rovibrational wave packets in the E(1Eg) "shelf" state of Li2 via quantum-state-resolved intermediate state selection"; J. Chem. Phys. vol. 106, No. 20; May 22, 1997; pp. 8310-8323.
John M. Papanikolas et al.; "Manipulation of rovibrational wave packet comosition in the Li2 E(1Eg) shelf state using intermediate state selection and shaped femtosecond laser pulses"; J. Chem. Phys., vol. 107, No. 11; Sep. 15, 1997; pp. 4172-4178.
Valerie Blanchet et al.; "Temporal Coherent Control in Two-Photon Transitions: From Optical Interferences to Quantum Interferences"; Physical Review Letters, vol. 78, No. 14; Apr. 7, 1997; pp. 2716-2719.
R. Zadoyan et al.; "Wavepacket diagnosis with chirped probe pulses"; Chemical Physics, vol. 233; 1998; pp. 353-363.
M.A. Bouchene et al.; "Temporal coherent control induced by wave packet interferences in one and two photon atomic transitions"; The European Physical Journal D, vol. 2; 1998; pp. 131-141.
Valerie Blanchet et al.; "Temporal coherent control in the photoionization Cs2: Theory and experiment"; Journal of Chemical Physics, vol. 108, No. 12; Mar. 22, 1998; pp. 4862-4876.
R.A. Bartels et al.; "Nonresonant Control of Multimode Molecular Wave Packets at Room Temperature"; Physical Review Letters, vol. 88, No. 3; Jan. 21, 2002; pp. 033001-1 through 033001-4.
T. Brixner et al.; "Abstract-Femtosecond quantum control"; Advances in Atomic, Molecular, and Optical Physics, vol. 46; 46: 1054; 2001 (1 page).
T. Brixner et al.; "Abstract-Photoselective adaptive femtosecond quantum control in the liquid phase"; Nature, 414 (6859); Nov. 1, 2001; pp. 57-60.
B. Dayan et al.; "Coherent control with broadband squeezed vacuum"; arXiv:quant-ph/0302038 v1; Feb. 5, 2003 (4 pages).

(56) References Cited

OTHER PUBLICATIONS

B. Dayan et al.; "Two Photon Absorption and Coherent Control with Broadband Down-Converted Light"; Physical Review Letters, vol. 93, No. 2; Jul. 9, 2004; pp. 023005-1023005-4.
B. Dayan et al.; "Nonlinear Interactions with an Ultrahigh Flux of Broadband Entangled Photons"; Physical Review Letters, PRL 94; Feb. 4, 2005, 2004; pp. 043602-1-043602-4.
N. Dudovich et al.; "Single-pulse coherent anti-Stokes Raman spectroscopy in the fingerprint spectral region"; J. of chem. Phys., vol. 118, No. 20; May 22, 2003; pp. 9208-9215.
D. Oron et al.; "Femtosecond Phase-and-Polaration Control for Background-Free Coherent Anti-Stokes Raman Spectroscopy"; Physical Review Letters, vol. 90, No. 21; May 30, 2003; pp. 213902-1-213902-4.
N. Dudovich et al.; "Quantum Control of the Angular Momentum Distribution in Multiphoton Absorption Processes"; Physical Review Letters, vol. 93, No. 10; Mar. 12, 2004; pp. 103003-1-103003-4.
D. Oron et al.; "All-optical processing in coherent nonlinear spectroscopy"; Physical Review A 70; 2004; pp. 023415-1-023415-4.
J.G. Underwood et al.; "Switched Wave Packets"; A Route to Nonperturbative Quantum Control; Physical Review Letters, vol. 90, No. 22; Jun. 6, 2003; pp. 223001-1-2230014.
M. Renard et al.; "Controlling ground-state rotational dynamics of molecules by shaped femtosecond laser pulses"; Physical Review A 69; 2004; 043401-1-043401-6.
A. Powe et al.; "Molecular Fluorescence, Phosphorescence, and Chemiluminescence Spectrometry"; Anal. Chem., vol. 76, No. 15; Aug. 15, 2004; pp. 4614-4634.
D. Abramavicius et al.; "Disentangling multidimensional femtosecond spectra of excitons by pulse shaping with coherent control"; J. of Chem. Phys., vol. 120, No. 18; May 8, 2004; pp. 8373-8378.
M.C. Chen et al.; "Coherent control multiphoton processes in semiconductor saturable Bragg reflector with freezing phase algorithm"; Appl. Phys. B 80; 2005; pp. 333-340.
W. Wohlleben et al.; "Coherent Control for Spectroscopy and Manipulation of Biological Dynamics"; Chem. Phys. Chem., 6; 2005; pp. 850-857.
T. Okada et al.; "Optical control of two-photon excitation efficiency of a-perylene crystal by pulse shaping"; Amer. Inst. of Phys., vol. 121, No. 13; Oct. 1, 2004; pp. 6386-6391.
V. Prokhorenko et al.; "Coherent control of the population transfer in complex sovated molecules at weak exitation. An experimental study"; The J. of Chem. Phys., 122; 2005; 184502-1-184502-11.
A. Prakelt et al.; "Phase control of two-photon transition with shaped femtosecond laser-pulse sequences"; Physical Review A 70; 2004; pp. 063407-1-06407-10.
B.J. Pearson et al.; "Control of Raman Lasing in the Nonimpulsive Regime"; Physical Review Letters, vol. 92, No. 24; Jun. 18, 2004; pp. 243003-1-243003-4.
Derryck T. Reid; "Algorithm for Complete and Rapid Retrieval of Ultrashort Pulse Amplitude and Phase from a Sonogram"; IEEE Journal Quantum Electronics; vol. 35, No. 11, Nov. 1999; pp. 1584-1589.
I.G. Cormack et al.; "Rapid measurement of ultrashort-pulse amplitude and phase from a two-photon absorption sonogram trace"; J. Opt. Soc. Am. B; vol. 18, No. 9, Sep. 2001; pp. 1377-1382.
E. Tokunaga et al.; "Frequency-domain interferometer for femtosecond time-resolved phase spectroscopy"; Optics Letters, vol. 17, No. 16; Aug. 15, 1992, pp. 1131-1133.
Victor Wong et al.; "Analysis of ultrashort pulse-shape measurement using linear interferometers"; Optics Letters, vol. 19, No. 4; Feb. 15, 1994; pp. 287-289.
Victor Wong et al.; "Linear filter analysis of methods for ultrashort-pulse-shape measurements"; J. Opt. Soc. Am. B, vol. 12, No. 8; Aug. 1995; pp. 1491-1499.
David M. Jones et al.; "Femtosecond Wavepacket Spectroscopy: Influence of Temperature, Wavelength and Pulse Duration"; J. Phys. Chem.; 1995; pp. 2594-2608.
J. Peatross et al.; "Temporal decorrelation of short laser pulses"; J. Opt. Soc. Am. B, vol. 15, No. 1; Jan. 1998; pp. 216-222.
McGraw-Hill Encyclopedia of Science & Technology, 6th Ed.; "Mass spectrometry"; 1987; pp. 492-502 (12 pages).
Ocean Optics Inc.; "HR4000 High-resolution Spectrometer"; http://oceanoptics.com/products/hr4000.asp; Jun. 25, 2005 (p. 1 of 4-p. 4 of 4).
Ocean Optics Inc.; "USB2000 Miniature Fiber Optic Spectrometer" http://oceanoptics.com/products/usb2000.asp; Jun. 25, 2005 (p. 1 of 7-p. 6 of 7).
Ocean Optics Inc.; "S2000 Miniature Fiber Optic Spectrometer"; http://oceanoptics.com/products/s2000.asp; Jun. 25, 2005 (p. 1 of 4-p. 4 of 4).
M. Schurenberg et al.; "Abstract-Laser desorption/ionization mass spectrometry of peptides and proteins with particle suspension matrixes"; Analytical Chemistry; 71 (1): 221-229; Jan. 1, 1999 (1 page).
F. Hillenkamp et al.; "Abstract-Matrix-assisted laser desorption/ionisation, an experience"; International Journal of Mass Spectrometry; 2000 (1-3); 71-77; Dec. 25, 2000 (1 page).
M.O. Scully, et al.; "Fast Cars: Engineering a laser spectroscopic technique for rapid identification of bacterial spores"; PNAS; vol. 99, No. 17; Aug. 20, 2002; pp. 10994-11001.
B. Natarajan et al.; "Abstract-Innovative pulse shaping for high-performance wireless TDMA"; IEEE Communications Letters; 5 (9): 372-374; Sep. 2001 (1 page).
A. Pe're et al.; "Optical Code-Division Multiple Access Using Broad-Band Parametrically Generated Light"; J. of Lightwave Tech.; vol. 22, No. 6; Jun. 2004; pp. 1463-1471.
J.J. Garcia-Ripoll et al.; "Speed Optimized Two-Qubit Gates with Laser Coherent Control Techniques for Ion Trap Quantum Computing"; Physical Review Letters, vol. 91, No. 15; Oct. 10, 2003; pp. 157901-1-157901-4.
J. Ahn et al.; "Information Storage and Retrieval Through Quantum Phase"; Science Magazine, vol. 287; Jan. 21, 2000; pp. 463-465.
Greg Taft et al.; "Measurement of 10-fs Laser Pulses"; IEEE Journal of Selected Topics in Quantum Electronics, vol. 2, No. 3, Sep. 1996; pp. 575-585.
Daniel J. Kane et al.; "Simultaneous measurement of two ultrashort laser pulses from a single spectrogram in a single shot"; Optical Society of America; vol. 14, No. 4, Apr. 1997; pp. 935-943.
Peter J. Delfyett et al.; "Joint Time-Frequency Meaurements of Mode-Locked Semiconductor Diode Lasers and Dynamics Using Frequency-Resolved Optical Gating"; IEEE Journal of Quantum Electronics, vol. 35, No. 4, Apr. 1999; pp. 487-500.
David N. Fittinghoff et al.; "Frequency-Resolved Optical Gating Measurement of Ultrashort Pulses Passing Through a High Numerical Aperture Objective"; IEEE Journal of Quantum Electronics, vol. 35, No. 4, Apr. 1999; pp. 479-486.
Andrius Baltuska et al.; "Second-Harmonic Generation Frequency-Resolved Optical Gating in the Single-Cycle Regime"; IEEE Journal of Quantum Electronics, vol. 35, No. 4, Apr. 1999; pp. 459-478.
Hilary K. Eaton et al.; "Investigating Nonlinear Femtosecond Pulse Propagation with Frequency-Resolved Optical Gating"; IEEE Journal of Quantum Electronics, vol. 35, No. 4, Apr. 1999; pp. 451-458.
Craig W. Siders et al.; "Multipulse Interferometric Frequency-Resolved Optical Gating"; IEEE Journal of Quantum Electronics, vol. 35, No. 4, Apr. 1999; pp. 432-440.
Atsushi Yabushita et al.; "SHG FROG and XFROG methods for phase/intensity characterization of pulses propagated through an absorptive optical medium"; Optics Communications; Oct. 15, 2001; pp. 227-232.
Roger G.M.P. Koumans et al.; "Time-Resolved Optical Gating Based on Dispersive Propagation: A New Method to Characterize Optical Pulses"; IEEE Journal of Quantum Electronics, vol. 36, No. 2, Feb. 2000; pp. 137-144.
Daniel J. Kane et al.; "Convergence test for inversion of frequency-resolved optical gating spectrograms"; Optics Letters, vol. 25, No. 16, Aug. 15, 2000; pp. 1216-1218.
Julie A. Gruetzmacher et al.; "Time and frequency-gated FID: a new approach to study the vibrational dephasing of water"; pp. 530-532.

(56) References Cited

OTHER PUBLICATIONS

Juan L.A. Chilla et al.; "Analysis of a Method of Phase Measurement of Ultrashort Pulses in the Frequency Domain"; IEEE Journal of Quantum Electronics, vol. 27, No. 5, May 1991; pp. 1228-1235.
David N. Fittinghoff et al.; "Noise sensitivity in frequency-resolved optical-gating measurements of ultrashort pulses"; J. Opt. Soc. am. B, vol. 12, No. 10, Oct. 1995; pp. 1955-1967.
Noriaki Tsurumachi et al.; "Interferometric observation of femtosecond free induction decay"; Optics Letters, vol. 19, No. 22, Nov. 15, 1994; pp. 1867-1869.
C. Dorrer et al.; "Characterization of chirped-pulse amplification systems with spectral phase interferometry for direct electric-field reconstruction"; Applied Physics B 70 (Suppl.), 2000; pp. S77-S84.
C. Radzewicz et al.; "A poor man's FROG"; Optics Communications, Dec. 15, 2000; pp. 329-333.
C. Dorrer et al.; "Spatio-temporal characterization of the electric field of ultrashort optical pulses using two-dimensional shearing interferometry"; Applied Physics B74 (Suppl.), 2002; pp. S209-S217.
K.H. Hong et al.; "Time-frequency analysis of chirped femtosecond pulses using Wigner distribution function"; Applied Physics B74 (Suppl.) 2002; pp. S231-S236.
Christophe Dorrer et al.; "Accuracy criterion for ultrashort pulse characterization techniques: application to spectral phase interferometry for direct electric field reconstruction"; Appl. Phys. B 74, vol. 19, No. 5, May 2002; pp. 1019-1029.
Kazunori Naganuma et al.; "General Method for Ultrashort Light Pulse Chirp Measurement"; IEEE Journal of Quantum Electronics, vol. 25, No. 5; Jun. 1989; pp. 1225-1233.
Y. Ding et al.; "Time-Domain Image Processing Using Dynamic Holography"; IEEE Journal of Selected Topics in Quantum Electronics, vol. 4, No. 2; Mar./Apr. 1998; pp. 332-341.
Chris laconis et al.; "Self-Referencing Spectral Interferometry for Measuring Ultrashort Optical Pulses"; IEEE Journal of Quantum Electronics, vol. 35, No. 4; Apr. 1999; pp. 501-509.
Jung-Ho Chung et al.; "Ambiguity of Ultrashort Pulse Shapes Retrieved From the Intensity Autocorrelation and the Power Spectrum"; IEEE Journal on Selected Topics of Quantum Elecronics, vol. 7, No. 4; Jul./Aug. 2001; pp. 656-666.
V. Kabelka et al.; "Time-frequency imaging of a single ultrashort light pulse from angularly resolved autocorrelation"; Optics Letters, vol. 20, No. 1; Jun. 1, 1995; pp. 1301-1303.
Paul R. Bolton et al.; "Propagation of intense, ultrashort laser pulses through metal vapor: refraction-limited behavior for single pulses"; J. Opt. Soc. Am. B, vol. 13, No. 2; Feb. 1996; pp. 336-346.
Jun.-Koo Rhee et al.; "Real-time dispersion analyzer of femtosecond laser pulses with use of a spectrally and temporally resolved upconversion technique"; J. Opt. Soc. Am. B, vol. 13, No. 8; Aug. 1996; pp. 1780-1785.
Marco A. Krumbugel et al.; "Direct ultrashort-pulse intensity and phase retrieval by frequency-resolved optical gating and a computational neural network"; Optics Letters, vol. 21, No. 2; Jan. 15, 1996; pp. 143-145.
David N. Fittinghoff et al.; "Measurement of the intensity and phase of ultraweak, ultrashort laser pulses"; Optics Letters, vol. 21, No. 12; Jun. 15, 1996; pp. 884-886.
T. Feurer et al.; "Measuring the temporal intensity of ultrashort laser pulses by triple correlation"; Appl. Phys. B; 1998; pp. 163-168.
Alfred Kwok et al.; "Frequency-Resolved Optical Gating Using Cascaded Second-Order Nonlinearities"; Journal of Selected Topics in Quantum Electronics, vol. 4, No. 2; Mar./Apr. 1998; pp. 271-277.
Daniel J. Kane, "Real-Time Measurement of Ultrashort Laser Pulse Using Principal Component Generalized Projection"; IEEE Journal of Selected Topics in Quantum Electronics; vol. 4, No. 2; Mar./Apr. 1998; pp. 278-284.
Scott A. Diddams et al.; "Characterizing the Nonlinear Propagation of Femtosecond Pulses in Bulk Media"; IEEE Journal of Selected Topics in Quantum Electronics, vol. 4, No. 2; Mar./Apr. 1998; pp. 306-316.
Michael J. Stimson et al.; "Noisy-light correlation functions by frequency resolved optical gating"; J. Opt. Soc. Am. B, vol. 15, No. 2; Feb. 1998; pp. 505-514.
J.W. Nicholson et al.; "Full-field characterization of femtosecond pulses by spectrum and cross-correlation measurements"; Optics Letters, vol. 24, No. 23; Dec. 1, 1999; pp. 1774-1776.
F. Romstad et al.; "Measurement of Pulse Amplitude and Phase Distortion in a Semiconductor Optical Amplifier: from Pulse Compression to Breakup"; IEEE Photonics Technology Letters, vol. 12, No. 12; Dec. 2000; pp. 1674-1676.
Tzu-Ming Liu et al.; "Triple-optical autocorrelation for direct optical pulse-shape measurement"; Applied Physics Letters, vol. 81, No. 8; Aug. 19, 2002; pp. 1402-1404.
Yoshihiro Takagi et al.; "Multiple- and single-shot autocorrelator based on two-photon conductivity in semiconductors"; Optics Letters, vol. 17, No. 9; May 1, 1992; pp. 658-660.
Thomas J. Dunn et al.; "Experimental Determination of the Dynamics of a Molecular Nuclear Wave Packet via the Spectra of Spontaneous Emission"; Physical Review Letters, vol. 70, No. 22; May 31, 1993; pp. 3388-3391.
A.N. Naumov et al.; "Frequency-time and time-space mappings for single-shot coherent four-wave mixing with chirped pulses and broad beams"; Journal of Raman Spectroscopy, 2001; pp. 960-970.
E.T.J. Nibbering et al.; "Spectral determination of the amplitude and the phase of intense ultrashort optical pulses"; J. Opt. Soc. Am. B, vol. 13, No. 2; Feb. 1996; pp. 317-329.
Victor Wong et al.; "Ultrashort-pulse characterization from dynamic spectrograms by iterative phase retrieval"; J. Opt. Soc. Am. B, vol. 14, No. 4; Apr. 1997; pp. 944-949.
Sarah M. Gallagher et al.; "Heterodyne detection of the complete electric field of femtosecond four-wave mixing signals"; J. Opt. Soc. Am. B, vol. 15, No. 8; Aug. 1998; pp. 2338-2345.
C. Dorrer et al.; "Single-shot real-time characterization of chirped-pulse amplification systems by spectral phase interferometry for direct electric-field reconstruction"; Optics Letters, vol. 24, No. 22; Nov. 15, 1999; pp. 1644-1646.
C. Dorrer; "Implementation of spectral phase interferometry for direct electric-field reconstruction with a simultaneously recorded reference interferogram"; Optics Letters, vol. 24, No. 21; Nov. 1, 1999; pp. 1532-1534.
C.Y. Chien et al.; "Single-shot chirped-pulse spectral interferometry used to measure the femtosecond ionization dynamics of air"; Optics Letters, vol. 25, No. 8; Apr. 15, 2000; pp. 578-580.
J.W. Nicholson et al.; "Unbalanced third-order correlations for full characterization of femtosecond pulses"; Optics Letters, vol. 25, No. 24; Dec. 15, 2000; pp. 1801-1803.
Sergey Yeremenko et al.; "Frequency-resolved pump-probe characterization of femtosecond infrared pulses"; Optics Letters, vol. 27, No. 13; Jul. 1, 2002; pp. 1171-1173.
J.M. Dudley et al.; "Direct measurement of pulse distortion near the zero-disperson wavelength in an optical fiber by frequency-resolved optical gating"; Optics Letters, vol. 22, No. 7; Apr. 1, 1997; pp. 457-459.
M.C. Chen et al.; "Freezing phase scheme for fast adaptice control and its application to characterization of femtosecond coherent optical pulses reflected from semiconductor saturable absorber mirrors"; J. Opt. Soc. Am. B, vol. 22, No. 5; May 2005; pp. 1134-1142.
I. Amat-Roldan et al.; "Measurement of electric field by interferometric spectral trace observation"; Optics Letters, vol. 30, No. 9; May 1, 2005; pp. 1063-1065.
I. Amat-Roldan et al.; "Starch-based second-harmonic-generated colinear frequency-resolved optical gating pulse characterization at the focal plane of a high-numericalaperture lens"; Optics Letters, vol. 29, No. 19; Oct. 1, 2004; pp. 2282-2284.
Gregory D. Goodno et al.; "Ultrafast heterodyne-defected transient-grating spectroscopy using diffractive optics"; Optical Society of America, vol. 15, No. 6, Jun. 1998; pp. 1791-1794.
L. Misoguti et al.; "Generation of Broadband Vuv Light Using Third-Order Cascaded Processes"; Physical Review Letters, vol. 87, No. 1, Jul. 2, 2001; pp. 013601-1-013601-4.
D. Zeidler et al.; "Amplification of tailored white-light continuum"; Applied Physics, B74 (Suppl), 2002; pp. S51-S56.

(56) References Cited

OTHER PUBLICATIONS

T. Brixner et al.; "Generation and characterization of polarization-shaped femtosecond laser pulses"; Applied Physics B74 (Suppl), 2002; pp. S133-S144.
Jeffrey L. Krause et al.; "Creating and Detecting Shaped Rydberg Wave Packets"; Physical Review Letters, vol. 79, No. 25; Dec. 22, 1997; pp. 4978-4981.
S. Backus et al.; "16-fs, 1-μ J ultraviolet pulses generated by third-harmonic conversion in air"; Optics Letters, vol. 21, No. 9; May 1, 1996; pp. 665-667.
Julie A. Gruetzmacher et al.; "Few-cycle mid-infrared pulse generation, characterization and coherent propagation in optically dense media"; Review of Scientific Instruments, vol. 73, No. 6; Jun. 2002; pp. 2227-2236.
T. Kobayashi et al.; "Tunable visible and near-infrared pulse generator in a 5 fs regime"; Appl. Phys. B 70 (Suppl);2000; pp. S239-S246.
A. Poppe et al.; "Few-cycle optical waveform synthesis"; Applied Physics B 72; 2001; pp. 373-376.
Peifang Tian et al.; "Ultrafast measurement of two-photon absorption by loss modulation"; Optics Letters, vol. 27, No. 18; Sep. 15, 2002; pp. 1634-1636.
M. Hentschel et al.; "Generation of 0.1-TW optical pulses with a single-stage Ti:sapphire amplifier at a 1-kHz repetition rate"; Appl. Phys. B 70 (Suppl); 2000; pp. S161-S164.
Photogen Technologies, Inc., "Photogen-Technology"; www.photogen.com/body/tech_body.html; Dec. 20, 2001 (19 pages).
W.M. Sharman et al.; "Photodynamic therapeutics: basic principles and clinical applications"; DDT, vol. 4, No. 11; Nov. 1991; pp. 507-517.
B.D. Fainberg; "Diagram Technique for Nonlinear Optical Spectroscopy in the Fast Electronic Dephasing Limit"; Journal of the Chinese Chemical Society, 47; 2000; pp. 579-582.
Chantal Daniel et al.; "Deciphering the Reaction Dynamics Underlying Optimal Control Laser Fields"; Science Magazine, vol. 299; Jan. 24, 2003; pp. 536-539.
T. Witte et al.; "Controlling molecular ground-state dissociation by optimizing vibrational ladder climbing"; Journal of Chemical Physics, vol. 118, No. 5; Feb. 1, 2003; pp. 2021-2024.
R.L. Levis et al.; "Closing the Loop on Bond Selective Chemistry Using Tailored Strong Field Laser Pulses"; The Journal of Physical Chemistry, vol. 106, No. 27; Jul. 11, 2002; pp. 6427-6444.
Mustafa Demirplak et al.; "Optical control of molecular dynamics in a liquid"; Journal of Chemical Physics, vol. 116, No. 18; May 8, 2002; pp. 8028-8035.
M. Bergt et al.; "Time-resolved organometallic photochemistry Femtosecond fragmentation and adaptive control of CpFe(CO)2X (X=C1, Br,I)"; Journal of Organometallic Chemistry 661; 2002; pp. 199-209.
Ben R. Torralva et al.; "Mechanisms for laser control of chemical reactions"; Journal of Modern Optics, vol. 49, No. 3/4; 2002; pp. 593-625.
N.H. Damrauer et al.; "Control of bond-selective photochemistry in CH2BrCI using adaptive femtosecond pulse shaping"; The European Physical Journal D, 20, 2002; pp. 71-76.
L. Windhorn et al.; "Molecular dissociation by mid-IR femtosecond pulses"; Chemical Physics Letters, 357, May 3, 2002; pp. 85-90.
Robert J. Levis et al.; "Selective Bond Dissociation and Rearrangement with Optimally Tailored, Strong-Field Laser Pulses"; Science Magazine, vol. 292; Apr. 27, 2001; pp. 709-713.
T. Brixner et al.; "Problem complexity in femtosecond quantum control"; Chemical Physics 267; 2001; pp. 241-246.
O.M. Sarkisov et al.; "Control of elementary chemical reactions by femtosecond light pulses"; Quantum Electronics, vol. 31, No. 6; 2001; pp. 483-488.
Julie A. Mueller et al.; "Competing isomeric product channels in the 193 nm photodissociation of 2-chloropropene and in the unimolecular dissociation of the 2-propenyl radical"; Journal of Chemical Physics, vol. 114, No. 10; Mar. 8, 2001; pp. 4505-4521.
Chantal Daniel et al.; "Analysis and control of laser induced fragmentation processes in CpMn(CO)3"; Chemical Physics 267; 2001; pp. 247-260.
A. Glass et al.; "Control of the photodissociation of CsCl"; Applied Physics B 71; 2000; pp. 267-276.
T. Frohnmeyer et al.; "Femtosecond pump-probe photoelectron spectroscopy on Na2: a tool to study basic coherent control schemes"; Applied Physics B 71; 2000; pp. 259-266.
M. Bergt et al.; "Controlling the Femtochemistry of Fe(CO)5"; J. Phys. Chem. A, vol. 103, No. 49; 1999; pp. 10381-10387.
A. Assion et al.; "Coherent control by a single phase shaped femtosecond laser pulse"; Chemical Physics Letters 259; Sep. 13, 1996; pp. 488-494.
Langchi Zhu et al.; "Coherent Laser Control of the Product Distribution Obtained in the Photoexcitation of HI"; Science Magazine, vol. 270; Oct. 6, 1995; pp. 77-80.
Yu-hui Chiu et al.; "Vibrational mode effects, scattering dynamics and energy disposal in reaction of C2H2 with methane"; J. Chem. Phys., vol. 102, No. 3; Jan. 15, 1995; pp. 1199-1216.
J.S. Keller et al.; "Selective bond fission in methyl mercaptan at 193 nm via radial derivative coupling between the 21A" and 11A"adiabatic electronic states"; J. Chem. Phys. vol. 96, No. 6; Mar. 15, 1992; pp. 4324-4329.
I Bar et al.; "Mode-selective bond fission: Comparison between the photodissociation of HOD (0,0,1) and HOD (1,0,0)"; J. Chem. Phys. vol. 95, No. 5; Sep. 1, 1991; pp. 3341-3346.
Michael J. Bronikowski et al.; "Bond-specific chemistry OD:OH product ratios for the reactions H+HOD(100) and H+HOD(001)"; J. Chem. Phys., vol. 95, No. 11; Dec. 1, 1991; pp. 8647-8648.
I. Bar et al.; "Direct observation of preferential bond fission by excitation of a vibrational fundamental: Photodissociation of HOD (0,0,1)"; J. Chem. Phys., vol. 93; No. 3; Aug. 1, 1990; pp. 2146-2148.
R.L. VanderWal et al.; "Selectively breaking the O-H bond in HOD"; J. Chem. Phys., vol. 92, No. 1; Jan. 1, 1990; pp. 803-805.
Neil Shafer et al.; "Isotope effect in the photodissociation of HOD at 157.5 nm"; J. Chem. Phys., vol. 90, No. 11; Jun. 1, 1989; pp. 6807-6808.
L.J. Butler et al.; "The electronic state-selective photodissociation of CH2BrI at 248,210 and 193nm"; J. Chem. Phys. vol. 86, No. 4; Feb. 15, 1997; pp. 2051-2074.
L.J. Butler et al.; "Bond selective photochemistry in CH2BrI through electronic excitation at 210 nm"; J. Chem. Phys., vol. 84, No. 7; Apr. 1, 1986; pp. 4104-4106.
David J. Tannor et al.; "Control of selectivity of chemical reaction via control of wave packet evolution"; J. Chem. Phys., vol. 83, No. 10; Nov. 15, 1985; pp. 5013-5018.
Christopher J. Bardeen et al.; "Quantum Control of Nal Photodissociation Reaction Product States by Ultrafast Tailored Light Pulses"; J. Phys. Chem. A, vol. 101, No. 20; 1997; pp. 3815-3822.
V.A. Apkarian; "Comment on 'Time-resolved laser induced harpoon reactions'"; J. Chem. Phys. vol. 106, No. 12; Mar. 22, 1997; pp. 5298-5299.
R.B. Vrijen et al.; "Limitations on quantum ladder climbing in complex systems"; Physical Review A, vol. 56, No. 3; Sep. 1997; pp. 2205-2212.
Lutfur R. Khundkar et al.; "Ultrafast Molecular Reaction Dynamics in Real-Time: Progress Over a Decade"; Annu. Rev. Phys. Chem., 1990; pp. 15-60.
Stuart A. Rice; "Optical control of reactions"; Nature magazine, vol. 403; Feb. 3, 2000; pp. 496-497.
Richard N. Zare; "Laser Control of Chemical Reactions"; Science magazine; vol. 279; Mar. 20, 1998; pp. 1875-1879.
Stuart A. Rice; "Active Control of Molecular Dynamics: Coherence versus Chaos"; Journal of Statistical Physics, vol. 101, Nos. 1/2; 2000; pp. 187-212.
Herschel Rabitz et al.; "Whither the Future of Controlling Quantum Phenomena?"; Science magazine, vol. 288; May 5, 2000; pp. 824-828.
Yuri T. Mazurenko; "Spectral Holography and Spectral Nonlinear Optics of Ultrashort Pulses"; Journal of the Chinese Chemical Society, vol. 47, No. 4A; 2000; pp. 679-683.

(56) References Cited

OTHER PUBLICATIONS

Marcos Dantus; "Coherent Nonlinear Spectroscopy: From Femtosecond Dynamics to Control"; Annu. Rev. Phys. Chem, 2001; pp. 639-679, C1-C7.
Stuart A. Rice; "Interfering for the good of a chemical reaction"; Nature magazine; vol. 409; Jan. 18, 2001; pp. 422-426.
Wolfgang Kiefer et al.; "Femtosecond time-resolved spectroscopy of elementary molecular dynamics"; Naturwissenschaften; 2002; pp. 250-258.
Alios Renn et al.; "Multidimensional Holography by Persistent Spectral Hole Burning"; The Journal of Physical Chemistry A, vol. 106, No. 13; Apr. 4, 2002; pp. 3045-3060.
T.C. Weinacht et al.; "Using feedback for coherent control of quantum systems"; Journal of Optics B. Quantum and Semiclassical Optics; 2002; pp. R35-R52.
Niels E. Henriksen; "Laser control of chemical reactions"; Chem. Soc. Rev. 3137 42; 2002; pp. 37-42.
Stuart A. Rice et al.; "Active control of product selection in a chemical reaction: a view of the current scene"; Phys. Chem. Chem. Phys., 2002; pp. 1683-1700.
Allen J. Bard et al.; "Holy Grails in Chemistry"; American Chemical Society, vol. 28, No. 3; Mar. 1995; 1 page.
Marcos Dantus; "Ultrafast Probing and Control of Molecular Dynamics: Beyond the Pump-Probe Method"; pp. 169-188, Kuhn & Weyh SRZ Sep. 4, 2001.
Bern Kohler et al.; "Controlling the Future of Matter"; Acc. Chem. Res., vol. 28, No. 3; 1995; pp. 133-140.
M.R. Fetterman et al.; "Propagation of Complex Laser Pulses in Optically Dense Media"; The American Physical Society, Physical Review Letters, vol. 82, No. 20, May 17, 1999; pp. 3984-3987.
D. Yelin et al.; "Adaptive femtosecond pulse compression"; Optics Letters, vol. 22, No. 23, Dec. 1, 1997; pp. 1793-1795.
A.V. Sokolov; "Subfemtosecond compression of periodic laser pulses"; Optics Letters, vol. 24, No. 17, Sep. 1, 1999; pp. 1248-1250.
H.S. Eisenberg et al.; "Phase Defects in Self-Focusing of Ultrashort Pulses"; Physical Review Letters, vol. 83, No. 3, Jul. 19, 1999; pp. 540-543.
D.M. Villeneuve et al.; "Using frequency-domain manipulation of stretched femtosecond laser pulses to create fast rise and fall times on picosecond pulses"; Applied Physics B74 (Suppl), 2002; pp. S157-S161.
Dai-Sik Kim et al.; "Femtosecond-pulse distortion in quantum wells"; Appl. Phys. B 74, vol. 48, No. 24; Dec. 15, 1993; pp. 17902-17905.
Anthony P. Peirce et al.; "Optimal control of quantum-mechanical systems: Existence, numerical approximation and applications"; Physical Review A, vol. 37, No. 12; Jun. 15, 1988; pp. 4950-4964.
J.M. Geremia et al.; "Incorporating physical implementation concerns into closed loop quantum control experiments"; Journal of Chemical Physics, vol. 112, No. 24; Dec. 22, 2000; pp. 10841-10848.
Thomas Hornung et al.; "Teaching optimal control theory to distill robust pulses even under experimental constraints"; Physical Review A, vol. 65; 2002; pp. 021403-1-021403-4.
Jianshu Cao et al.; "Intrapulse Dynamical Effects in Multiphoton Processes: Theoretical Analysis"; J. Phys. Chem. A; vol. 102, 1998; pp. 4284-4290.
Amichay Vardi et al.; "Laser catalysis with pulses"; Physical Review A, vol. 58, No. 2;Aug. 1998; pp. 1352-1360.
Kazuya Takasago et al.; "Evaluation of Femtosecond Pulse Shaping with Low-Loss Phase-Only Masks"; IEEE Journal of Selected Topics in Quantum Electronics, vol. 4, No. 2; Mar./Apr. 1998; pp. 346-352.
M.E. Fermann et al.; "Shaping of ultrashort optical pulses by using an integrated acoustooptic tunable filter"; Optics Letters, vol. 18, No. 18; Sep. 15, 1993; pp. 1505-1507.
V.L. da Silva et al.; "Nonlinear pulse shaping and causality"; Optics Letters, vol. 18, No. 8; Apr. 15, 1993; pp. 580-582.
E. Zeek et al.; "Adaptive pulse compression for transform-limited 15-fs high-energy pulse generation"; Optics Letters, vol. 25, No. 8; Apr. 15, 2000; pp. 587-589.
A. Apolonski et al.; "Controlling the Phase Evolution of Few-Cycle Light Pulses"; Physical Review Letters, vol. 85, No. 4; Jul. 24, 2000; paes 740-743.
Christophe Dorrer et al.; "Phase Amplitude Coupling in Spectral Phase Modulation"; IEEE Journal of Selected Topics in Quantum Electronics, vol. 4, No. 2; Mar./Apr. 1998; pp. 342-345.
David J. Jones et al.; "Carrier-Envelope Phase Control of Femtosecond Mode-Locked Lasers and Direct Optical Frequency Synthesis"; Science magazine, vol. 288; Apr. 28, 2000; pp. 635-639.
Vladimir Kalosha et al.; "Generation of Single Dispersion Precompensated 1-fs Pulses by Shaped-Pulse Optimized High-Order Stimilated Raman Scattering"; Physical Review Letters, vol. 88, No. 10; Mar. 11, 2002; pp. 103901-1-13901-4.
Donna Strickland et al.; "Compression of Amplified Chirped Optical Pulses"; Optics Communications; vol. 55, No. 6; Oct. 15, 1985; pp. 447-449.
H. Wang et al.; "Abstract-20-fs pulse shaping with a 512-element phase-only liquid crystal modulator"; IEEE Journal of Selected Topics in Quantum Electronics; 7 (4): 718-727; Jul./Aug. 2001 (1 page).
L. Xu et al.; "Abstract-Programmable chirp compensation for 6-fs pulse generation with a prism-pair-formed pulse shaper"; IEEE Journal of Quantum Electronics; 36 (8): 893-899; Aug. 2000 (1 page).
CVI Laser Corporation; "TNM-2 Negative Group Velocity Dispersion Mirrors"; www.cvilaser.com/ultra-fast; Jan. 13, 2002 (2 page).
H. Takada et la.; "Large-ratio stretch and recompression of sub-10-fs pulses utilizing dispersion managed devices and a spatial light modulator"; Appl. Phys. B 74 (Suppl); 2002; pp. S253-S257.
N. Karasawa et al.; "Optical pulse compression to 5.0 fs by use of only a spatial light modulator for phase compensation"; J. Opt. Soc. Am. B, vol. 18, No. 11; Nov. 2001; pp. 1742-1746.
C.P.J. Barty et al.; "Generation of 18-fs, multiterawatt pulses by regenerative pulse shaping and chirped-pulse amplification"; Optics Letters, vol. 21, No. 9; May 1, 1996; pp. 668-670.
Marcos Dantus; GeneticAlgorithm-v4.nb to simulate an adaptive genetic algorithm; Oct. 2001; pp. 1-7.
M. Hacker et al.; "Iterative Fourier transform algorithm for phase-only pulse shaping"; Optics Express, vol. 9, No. 4, Aug. 13, 2001; pp. 191-199.
T. Brixner et al.; "Feedback-controlled optimization of amplified femtosecond laser pulses"; Applied Physics B 68; 1999; pp. 281-284.
A. Efimov et al.; "Minimization of dispersion in an ultrafast chirped pulse amplifier using adaptive learning"; Appl. Phys. B 70 (Suppl); 2000; pp. S133-S141.
D. Zeidler et al.; "Evolutionary algorithms and their application to optimal control studies"; Physical Review A, vol. 64; 2001; pp. 023420-1-023420-13.
C. Rangan et al.; "Optimally shaped terahertz pulses for phase retrieval in a Rydberg-atom data register"; Physical Review A, vol. 64; 2001; pp. 033417-1-033417-5.
T. Tanabe et al.; "Compensation for a Transfer Function of a Regenerative Amplifier to Generate Accurately Shaped Ultrashort Pulses in Both the Amplitude and Phase"; IEEE J. of Selected Topics in Quantum Electronics, vol. 10, No. 1; Jan./Feb. 2004; pp. 221-228.
Hosseini, S. Abbas et al.; "Coherent control of multiphoton transitions with femtosecond pulse shaping"; Physical Review a; pp. 033410-1-033410-7.
Yan, Y.J. et al.; "Electronic dephasing, vibrational relaxation, and solvent friction in molecular nonlinear optical line shapes"; J. Chems. Phys.; Oct. 15, 1988; pp. 5160-5176.
Meshulach, D. et al.; "Coherent quantum control of multiphoton transitions by shaped ultrashort optical pulses"; Phys. Rev. A 60; 1999; pp. 1287-1292.
Weinacht, T.C. et al.; "Controlling the shape of a quantum wavefunction"; Nature, vol. 397; Jan. 1999; pp. 233-235.
Buist, A.H. et al.; "Probing microscopic chemical environments with high-intensity chirped pulses"; Optics Letters 24; 1999; pp. 244-246.
Broers, B. et al.; "Large interference effects of small chirp observed in two-photon absorption"; Opt. Commun. 91; 1992; pp. 57-61.
Broers, B. et al.; "Diffraction and focusing of spectral energy in multiphoton processes"; Phys. Rev. A 46; 1992; pp. 2749-2756.
Walowicz, K.A. et al.; "Multiphoton Intrapulse Interference 1: Control of Multiphoton Processes in Condensed Phases"; J. Phys. Chem A 106 (41); Oct. 17, 2002; pp. 9369-9373.

(56) References Cited

OTHER PUBLICATIONS

Zheng, Z. et al.; "Coherent control of second harmonic generation using spectrally phase coded femtosecond waveforms"; Chem. Phys. 267; 2001; pp. 161-171.
Clara et al.; "Femtosecond laser mass spectroscopy of ferrocenes: Photochemical stabilization by bridged cyclopentadienyl rings?"; International Journal of Mass Spectrometry, Elsevier Science Publishers, vol. 203, No. 1-3; Dec. 26, 2000; pp. 71-81.
Bucksbaum, Philip; "An atomic dimmer switch"; Nature; Nov. 19, 1998; vol. 396; pp. 217-219.
Dela Cruz, J.M. et al.; "Multiphoton Intrapulse Interference 3: Probing Microscopic Chemical Environments"; J. Phys. Chem. A 2004, 108; pp. 53-58.
Goswami, D.; "Optical pulse shaping approaches to coherent control"; Physics Reports 374; 2004; pp. 385-481.
Leibfried, D. et al.; "Quantum information with trapped ions at NIST"; Journal of Modern Optics; vol. 50, No. 6/7; Apr.-May 2003; pp. 1115-1129.
Lozovoy, V.V.; "Multiphoton intrapulse interference. II. Control of two- and three-photon laser induced flurorescence with shaped pulses"; J. Chem. Phys. 118 (7); Feb. 15, 2005; pp. 3187-3196.
Roy, I. et al.; "Ceramic-based nanoparticles entrapping water-insoluble photosensitizing drugs: A novel drug carrier system for photodynamic therapy"; J. Am. Chem. Soc. 125; 2003, pp. 7860-7865.
VandenBout, D.A. et al.; "Discrete intensity jumps and intramolecular electronic energy transfer in the spectroscopy of single conjugated polymer molecules"; Science 277; 2997; pp. 1074-1077.
Paye, J.; "How to Measure the Amplitude and Phase of an Ultrashort Light Pulse with an Autocorrelator and a Spectrometer"; IEEE Journal of Quantum Electronics, vol. 30, No. 11; Nov. 1994; pp. 2693-2697.
Kovtoun et al.; "Mass-Correlated Pulsed Extraction: Theoretical Analysis and Implementation With a Linear Matrix-Assisted Laser Desorption/lonization Time of Flight Mass Spectrometer"; Journal of the American Society for Mass Spectrometry, Elsevier Science Inc.; vol. 11, No. 10; Oct. 2000; pp. 841-853.
Mitra et al.; "Nonlinear Limits to the Information Capacity of Optical Fibre Communications"; Nature; vol. 411; Jun. 28, 2001; pp. 1027-1030.
Brattke, S. et al.; "Generation of Photon No. States on Demand via Cavity Quantum Electrodynamics"; Phys. Rev. Lett.; vol. 86; Apr. 16, 2001; pp. 3534-3537.
Goswami, D.; "Ultrafast Pulse Shaping Approaches to Quantum Computing"; Indian Institute of Technology; Dec. 24, 2003 (8 pages).
Xu, C. et al.; "Two photon optical beam induced current imaging throughout backside of integrated circuits"; Appl. Phys. Lett. 71; 1997; pp. 2578-2580.
Yang, W., et al.; "High-ratio Electro-optical Data Compression for Massive Accessing Networks Using AOM-based Ultrafast Pulse Shaping"; Journal of Optical Communications' vol. 22, No. 1; 2001; pp. 15-18.
Kane, Daniel J., et al.; "Single-shot measurement of the intensity and phase of an arbitrary ultrashort pulse by using frequency-resolved optical gating"; Optics Letters, vol. 18, No. 10; May 15, 1993; pp. 823-825.
Kane, Daniel J. et al.; "Single-shot measurement of the intensity and phase of a femtosecond UV laser pulse with frequency-resolved optical gating"; Optics Letters, vol. 19, No. 14; Jul. 15, 1994; pp. 1061-1063.
Clement, Tracy Sharp et al.; "Single-shot measurement of the amplitude and phase of ultrashort laser pulses in the violet"; Optics Letters, vol. 20, No. 1; Jan. 1, 1995; pp. 70-72.
Kohler, Bern et al.; "Phase and intensity characterization of femtosecond pulses from a chirped-pulse amplifier by frequency-resolved optical gating"; Optics Letters, vol. 20, No. 5, Mar. 1, 1995; pp. 483-485.
Sweetser, John N. et al.; "Transient-grating frequency-resolved optical gating"; Optics Letters, vol. 22, No. 8; Apr. 15, 1997; pp. 519-521.
Trebino, Rick et al.; "Measuring ultrashort laser pulses in the time-frequency domain using frequency-resolved optical gating"; Rev. Sci. Instrum. 68 (9); Sep. 1997; pp. 3277-3295.
Dudley, John M. et al.; "Complete Characterization of Ultrashort Pulse Sources at 1550 nm"; IEEE Journal of Quantum Electronics, vol. 35, No. 4: Apr. 1999; pp. 441-450.
Trebino, Rick et al.; "The Dilemma of Ultrashort-Laser-Pulse Intensity and Phase Measurement and Applications"; IEEE Journal of Quantum Electronics, vol. 35, No. 4: Apr. 1999; pp. 418-420.
Cormack, I.G. et al.; "Practical measurement of femtosecond optical pulses using time-resolved optical gating"; Optics Communications 194; Jul. 15, 2001; pp. 415-424.
Chu, K.C. et al.; "Direct measurement of the spectral phase of femtosecond pulses"; Optics Letters, vol. 20, No. 8; Apr. 15, 1995; pp. 904-906.
Sullivan, A. et al.; "Quantitative investigation of optical phase-measuring techniques for ultrashort pulse lasers"; J. Opt. Soc. Am. B, vol. 13, No. 9; Sep. 1996; pp. 1965-1978.
Baltuska, Andrius et al.; "Amplitude and phase characterization of 4.5-fs pulses by frequency-resolved optical gating"; Optics Letters, vol. 23, No. 18; Sep. 15, 1998; pp. 1474-1476.
Gallmann, L. et al.; "Techniques for the characterization of sub-10-fs optical pulses: a comparison"; Appl. Phys. B 70 (Suppl); 2000; pp. S67-S75.
Anderson, M.E. et al.; "The effects of noise on ultrashort-optical-pulse measurement using Spider"; Appl. Phys. B 70 (Suppl); 2000; pp. S85-S93.
Nicholson, J.W. et al.; "Noise sensitivity and accuracy of femtosecond pulse retrieval by phase and intensity from correlation and spectrum only (PICASO)"; J. Opt. Soc. Am. B; vol. 19, No. 2; Feb. 2002; pp. 330-339.
Dorrer, Christophe et al.: "Precision and consistency criteria in spectral phase interferometry for direct electric-field reconstruction"; J. Opt. Soc. Am. B, vol. 19, No. 5; May 2002; pp. 1030-1038.
Walmsley, Ian A. et al.; "Characterization of the electric field of ultrashort optical pulses"; J. Opt. Soc. Am. B., vol. 13, No. 11; Nov. 1996; pp. 2453-2463.
Lange, H. Rudiger et al.; "Reconstruction of the Time Profile of Femtosecond Laser Pulses through Cross-Phase Modulation"; IEEE Journal of Selected Topics, in Quantum Electronics, vol. 4, No. 2; Mar./Apr. 1998; pp. 295-300.
Iaconis, C. et al.; "Direct Interferometric Techniques for Characterizing Ultrashort Optical Pulses"; IEEE Journal of Selected Topics in Quantum Electronics, vol. 4, No. 2; Mar./Apr. 1998; pp. 285-294.
Iaconis, C. et al.; "Spectral phase interferometry for direct electric-field reconstruction of ultrashort optical pulses", Optics Letters, vol. 23, No. 10, May 15, 1998; pp. 792-794.
Dietrich, P. et al.; "Determining the absolute carrier phase of a few-cycle laser pulse"; Optics Letters, vol. 25, No. 1, Jan. 1, 2000; pp. 16-18.
Reid, D.T. et al.; "Amplitude and phase measurement of mid-infrared femtosecond pulses by using cross-correlation frequency-resolved optical gating"; Optics Letters, vol. 25, No. 19, Oct. 1, 2000; pp. 1478-1480.
Michelmann, K. et al.; "Measurement of the p. function of an ultrashort laser pulse"; Optics Communications; Oct. 15, 2001; pp. 163-170.
Gallmann, L. et al.; "Spatially resolved amplitude and phase characterization of femtosecond optical pulses"; Optics Letters, vol. 26, No. 2; Jan. 15, 2001; pp. 96-98.
Kakehata, Masayuki et al.; "Single-shot measurement of carrier-envelope phase changes by spectral interferometry"; Optics Letters, vol. 26, No. 18; Sep. 15, 2001; pp. 1436-1438.
Geindre, J.P. et al.; "Single-shot spectral interferometry with chirped pulses"; Optics Letters, vol. 26, No. 20; Oct. 15, 2001; pp. 1612-1614.
Dorrer, C. et al.; "Direct space-time characterization of the electric fields of ultrashort optical pulses"; Optics Letters, vol. 27, No. 7; Apr. 1, 2002; pp. 548-550.
Trebino, R., et al.; "Measuring Ultrashort Laser Pulses Just Got a Lot Easier!"; Optics & Photonics News; Jun. 2001; pp. 22-25.

(56) References Cited

OTHER PUBLICATIONS

Zheng, Z. et al.; "Spectral phase correlation of coded femtosecond pulses by second-harmonic generation in thick nonlinearcrystals"; Opt. Lett. 25; 2000; pp. 984-986.
Spielmann, C. et al.; "Ultrabroadband Femtosecond Lasers"; IEEE Journal of Quantum Electronics; vol. 30, No. 4; Apr. 1994; pp. 1100-1114.
Yelin, D. et al.; "Laser scanning third-harmonic-generation microscopy in biology"; Optics Express; vol. 5, No. 8; Oct. 11, 1999; pp. 169-175.
Zipfel, W.R. et al.; "Nonlinear magic: multiphoton microscopy in the biosciences"; Natire Biotechnology, 121 (11); Nov. 2003; pp. 1369-1377.
Larson, D.R. et al.; "Water-soluble quantum dots for multiphoton fluorescence imaging in vivo"; Science 300; May 30, 2003; pp. 1434-1436.
Osborn, D.L. et al.; "Spectral and intensity dependence of spatially resolved two-photon conductivity defects on a GaAsP photodiode"; J. Appl. Phys. 89; 2001; pp. 626-633.
Pastirk, I. et al.; "Selective two-photon microscopy with shaped femtosecond pulses"; Opt. Express 11; 2003; pp. 1695-1701.
Drexler W. et al.; "In vivo ultrahigh-resolution optical coherence tomography"; Optics Letters; vol. 24, No. 17; Sep. 1, 1999; pp. 1221-1223.
Hasan, T. et at; "Photodynamic Therapy of Cancer"; Chapter 40 in Holland Frei Cancer Medicine; BC Dekker Inc.; 2003; (55 pages).
Sharman, W.M. et al.; "Targeted photodynamic therapy via receptor mediated delivery systems"; Adv. Drug Delivery Rev. 56(1); Jan. 2004; pp. 53-76.
Assion, A., et al.; "Control of Chemical Reactions by Feedback-Optimized Phase-Shaped Femtosecond Laser Pulses"; Science Magazine, vol. 282; Oct. 30, 1998; pp. 919-922.
Warren, W.S.; "Chemistry with photons"; Science, vol. 262; Nov. 12, 1993; pp. 1008-1009.
Chilla, Juan L.A. et al.; "Direct determination of the amplitude and the phase of femtosecond light pulses"; Optics Letters; vol. 16, No. 1; Jan. 1, 1991; pp. 39-41.
Kim, D.S. et al.; "Femtosecond pulse distortion in GaAs quantum wells and its effect on pump-probe or four-wave-mixing experiments"; Physical Review B; vol. 50, No. 24; Dec. 15, 1994; pp. 18240-18249.
Kaindl, Robert A. et al.; "Generation, shaping, and characterization of intense femtosecond pulses tunable from 3 to 20 μm"; J. Opt. Soc. am. B; vol. 17, No. 12; Dec. 2000; pp. 2085-2094.
Panasenko, Dmitriy et al.; "Single-shot sonogram generation for femtosecond laser pulse diagnostics by use of two-photon absorption in a silicon CCD camera"; Optics Letters; vol. 27, No. 16; Aug. 15, 2002; pp. 1475-1477.
Baltuska, Andrius et al.; "Visible pulse compression to 4 fs by optical parametric amplification and programmable dispersion control"; Optics Letters; vol. 27, No. 5; Mar. 1, 2002; pp. 306-308.
Meshulach D. et al.; "Adaptive ultrashort pulse compression and shaping"; Optics Communications 138; 1997; pp. 345-348.
Brixner, T. et al.; "Feedback-controlled femtosecond pulse shaping"; Appl. Phys. B 70 (Suppl); 2000; pp. S119-S124.
Stobrawa, G. et al.; "A new high-resolution femtosecond pulse shaper"; Appl. Phys. B 72; 2001; pp. 627-630.
Hacker, M. et al.; Frequency doubling of phase-modulated, ultrashort laser pulses; Appl. Phys. B 73; 2001; pp. 273-277.
Weiner, Andrew M. et al.; "Femtosecond Pulse Shaping for Synthesis, Processing and Time-to-Space Conversion of Ultrafast Optical Waveforms"; IEEE Journal of Selected Topics in Quantum Electronics; vol. 4, No. 2; Mar./Apr. 1998; pp. 317-331.
Dudovich, N. et al.; "Transform-limited pulses are not optimal for resonant multiphoton transitions"; Phys. Rev. Letter. 86; 2001; pp. 47-50.
Hillegas, C.W. et al.; Femtosecond laser pulse shaping by use of microsecond radio-frequency pulses; Optics Letters; vol. 19, No. 10; May 15, 1994; pp. 737-739.
Weiner, A.M. et al.; "Programmable Shaping of Femtosecond Optical Pulses by Use of 128-Element Liquid Crystal Phase Modulator"; IEEE Journal of Quantum Electronics; vol. 28, No. 4; Apr. 1992; pp. 908-920.
Matuschek, N.: "Back-side-coated chirped mirrors with ultra-smooth broadbank dispersion characteristics"; Applied Physics B 71; Sep. 6, 2000; pp. 509-522.
Ding, Y.; "Femtosecond pulse shaping by dynamic holograms in photorefractive multiple quantum wells"; Optics Letters' vol. 22, No. 10; May 15, 1997; pp. 718-720.
Imeshev, G. et al.; "Engineerable femtosecond pulse shaping by second-harmonic generation with Fourier synthetic quasi-phase-matching gratings"; Optics Letters; vol. 23, No. 11; Jun. 1, 1998; pp. 864-866.
Tull, J.X. et al.; "High-Resolution, Ultrafast Laser Pulse Shaping and its Applications"; Advances in Magnetic and Optical Resonance; vol. 20; 1997; pp. 1-65.
Weiner, A.M.; "Femtosecond pulse shaping using spatial light modulators"; Rev. Sci. Instrum. vol. 71(5); 2000; pp. 1929-1960.
Schreier, F. et al.; "Femtosecond pulse shaping with a stratified diffractive structure"; Optics Communications 185; 2000; pp. 227-231.
Bhattacharya, N. et al.; "Implementation of Quantum Search Algorithm using Classical Fourier Optics"; Phys. Rev. Lett.; vol. 88, No. 13; Apr. 1, 2002; pp. 137901-1-137901-4.
Baumert, T. et al.; "Femtosecond pulse shaping by an evolutionary algorithm with feedback"; Appl. Phys. B 65; 1997; pp. 779-782.
Hornung, Thomas et al.; "Adapting optimum control theory and using learning loops to provide experimentally feasible shaping mask patterns"; Journal of Chemical Physics; vol. 115, No. 7; Aug. 15, 2001; pp. 3105-3111.
Meshulach, D. et al.; "Adaptive real-time femtosecond pulse shaping"; J. Opt. Soc. Am. B; vol. 15, No. 5; May 1998; pp. 1615-1619.
Zeidler, D. et al.; "Adaptive compression of tunable pulses from a non-collinear-type OPA to below 16 fs by feedback-controlled pulse shaping"; Appl. Phys. B 70 (Suppl); 2000; pp. S125-S131.
H. Zou, C. Zhou; "Femtosecond Pulse Shaping with Space-to-Time Conversion Based on Planar Optics"; Optik Optics, ScienceDirect, 2006/2007, pp. 5-8.
S. Zhang, et al.; "Coherent Enhancement of Broadband Frequency Up-Conversion in BBO Crystal by Shaping Femtosecond Laser Pulses"; Optics Communications, ScienceDirect, 2006/2007, pp. 559-563.
Y. Oishi, A. Suda, F. Kannari, K. Midorikawa; "Intense Femtosecond Pulse Shaping Using a Fused-Silica Spatial Light Modulator"; Optics Communications, ScienceDirect, 2006/2007, pp. 305-309.
B. Xu, Y. Coello, V.Lozovoy, D. Harris, M. Dantus; "Pulse Shaping of Octave Spanning Femtosecond Laser Pulses"; Optics Express, vol. 14, No. 22, Oct. 30, 2006, pp. 10939-10944.
F.M. Reinert, M. Ninck, W. Luthy, T. Feurer; "Shaping a Femtosecond Pulse with a Programmable Thermo-Optically Driven Phase Modulator"; Optics Express, vol. 15, No. 7, Apr. 2, 2007, pp. 4372-4377.
H. Miao, A. Weiner, C. Langrock, R. Roussev, M. Fejer; "Sensing and Compensation of Femtosecond Waveform Distortion Induced by All-Order Polarization Mode Dispersion at Selected Polarization States"; Optics Letters, vol. 32, No. 4, Feb. 15, 2007, pp. 424-426.
S. Nath, D. Urbanek, S. Kern, M. Berg; "High-Resolution Raman Spectra with Femtosecond Pulses: An Example of Combined Time- and Frequency-Domain Spectroscopy"; Physical Review Letters, 2006, pp. 267401-1 to 267401-4.
Comstock et al., "Multiphoton intrapulse interference 6; binary phase shaping"; Optics Express Opt. Soc. America USA, vol. 12, No. 6, Mar. 22, 2004; pp. 1061-1066.
Hu et al., "A New Nonlinear Optical Crystal-BaAlBO3 F2(BABF)"; Japanese Journal of Applied Physics, vol. 41, No. 10B, Part 2, Oct. 15, 2002; pp. L1131-L1133.
Weiner et al., "Shaping of femtosecond pulses using phase-only filters designed by simulated annealing"; Journal of the Optical Society of America A (Optics and Image Science) USA, vol. 10, No. 5, May 1993; pp. 1112-1120.
M. Dantus et al., "Experimental Coherent Laser Control of Physicochemial Processes", Chem. Rev. 2004, 104, pp. 1813-1859.

(56) References Cited

OTHER PUBLICATIONS

M. Hacker et al., "Iterative Fourier Transform Algorithm for Phase-Only Pulse Shaping", Optics Express, vol. 9, No. 4, Aug. 13, 2001, pp. 191-199.
R. Bartels et al., "Shaped-Pulse Optimization of Coherent Emission of High-Harmonic Soft X-Rays", 2000 Macmillan Magazines Ltd., Nature, vol. 406, Jul. 13, 2000, pp. 164-166.
Dela Cruz, J. et al.; "Use of coherent control methods through scattering biological tissue to achieve functional imaging"; PNAS, vol. 101, No. 49, Dec. 7, 2004, pp. 16996-17001.
Weiner, A.M. et al.; "Generation of terahertz-rate trains of femtosecond pulses by phase-only filtering"; Optics Letters, vol. 15, No. 1, Jan. 1, 1990, pp. 51-53.
Kroner, D. et al.; "Asymmetric Laser Excitation in Chiral Molecules: Quantum Simulations for a Proposed Experiment"; Chemical Physics Letters Elsevier Netherland, vol. 372, No. 1-2, Apr. 22, 203, pp. 242-248.
Hoki, K et al.; "Locally Designed Pulse Shaping for Selective Preparation of Enantiomers from their Racemate"; Journal of Chemical Physics, New York, NY, vol. 114, No. 4, Jan. 22, 2001, pp. 1575-1581.
Bychkov S.S. et al.; "Laser Synthesis of Chiral Molecules in Isotropic Racemic Media"; Journal of Experimental and Theoretical Physics, Nauka/Interperiodica, MO, vol. 93, No. 1, Jul. 1, 2001, pp. 24-32.
Hoki, K. et al.; "Selective Preparation of Enantiomers from a Racemate by Laser Pulses: Model Simulation for Oriented Atropisomers with Coupled Rotations and Torsions"; Chemical Physics Elsevier Netherlands, vol. 267, No. 1-3, Jun. 2001, pp. 59-79.
Brixner, T. et al.; "Quantum Control by Ultrafast Polarization Shaping"; Phys. Lett., vol. 92, No. 20, May 21, 2004, pp. 208301-1-208301-4.
Thanopulos, I. et al.; "Laser-Driven Coherent Manipulation of Molecular Chirality"; Chemical Physics Letters Elsevier Netherlands, vol. 390, No. 1-3, May 21, 2004, pp. 228-235.
Atabek, O. et al.; "Intense Laser Control of the Chemical Bond"; Theochem Elsevier Netherlands, vol. 493, Dec. 15, 1999, pp. 89-101.
Pelfang Tian et al.; "Femtosecond Phase-Coherent Two-Dimensional Spectroscopy"; Science American Assoc. Adv. Sci. USA, vol. 300, No. 5625, Jun. 6, 2003, pp. 1553-1555.
Motzkus, M.; "Open and Closed Loop Control of Complex Molecules with Shaped fs Pulses"; 2003 International Conference Physics and Control Proceedings (Cat. No. 03EX708), IEEE Piscataway, NJ, USA, vol. 3, 2003, p. 746.
Ma, et al.; Intense Femtosecond Laser Field-Induced Coulomb Fragmentation of C2H4, International Journal of Mass Spectrometry, Elsevier, Amsterdam, NL, vol. 242, No. 1, Mar. 15, 200, pp. 43-48.
Wu C. et al.; "Mass and Photoelectron Spectrometer for Studying Field-Induced Ionization of Molecules"; International Journal of Mass Spectrometry, Elsevier Science Publishers, Amsterdam, NL, vol. 216, No. 3, May 15, 2002, pp. 249-255.
Chen Jr. et al.; "Femtosecond Laser-Induced Dissociative Ionization and Coulomb Explosion of Ethanol"; International Journal of Mass Spectrometry, Elsevier, Amsterdam, NL, vol. 241, No. 1, Feb. 15, 2005, pp. 25-29.
Wu, Chengyin et al.; "Laser-Induced Dissociation and Explosion of Methane and Methanol"; J. Phys. B. At. Mol. Opt. Phys.; Journal of Physics B: Atomic, Molecular and Optical Physics, Jun. 14, 2002, vol. 35, No. 11, pp. 2575-2582.
Tomizawa H. et al.; "Development of Automatically Optimizing System of Both Spatial and Temporal Beam Shaping for UV-Laser Pulse"; Proceedings of the SPIE—The International Society for Optical Engineering SPIE-Int. Soc. Opt. Eng USA, vol. 5481, No. 1, 2004, pp. 47-55.
Yu, Huang, et al.; "Application of Adaptive Feedback Loop for Ultra-Violet Femtosecond Pulse Shaper Control"; Optics Express Opt. Soc. America USA, vol. 14, No. 21, Oct. 2006, pp. 10089-10094.
Roth, M. et al.; "Acousto-Optic Femtosecond Pulse Shaping in the Ultraviolet, Lasers and Electro-Optics", 2005. (Cleo). Conference in Baltimore, MD., USA, May 22-27, 2005, Piscataway, NJ, USA. IEEE, May 22, 2005, pp. 2244-2246.
Roth, M. et al.; "Acousto-optical Shaping of Ultraviolet Femtosecond Pulses"; Applied Physics B; Lasers and Optics, Springer-Verlag, BE, vol. 80, No. 4-5, Apr. 1, 2005, pp. 441-444.
Hanna, Sherif F. et al.; "Electronic-resonance-enhanced coherent anti-Stokes Raman spectroscopy of nitric oxide"; Applied Physcis Letters; vol. 83, No. 9, Sep. 1, 2003; pp. 1887-1889.
Beadie, G. et al.; "Towards a FAST-CARS anthrax detector: CARS generation in a DPA surrogate molecule"; Journal of Modern Optics, vol. 50, No. 15-17, 2003, pp. 2361-2368.
Yelin, D. et al.; "Laser scanning third-harmonic-generation microscopy in biology"; Optics Express, vol. 5, No. 8, Oct. 11, 1999; pp. 169-175.
Fowles, "Introduction to Modern Optics," 1989, Dover 2e, pp. 2-19.
Ogawa et al, Dependence of the Laser Two-Photon Ionization Process in Solution on the Laser Pulse Width, Analytical Chemistry, vol. 73, Mar. 20, 2001, pp. 2066-2069.
Zeek, Erik; "Pulse Shaping for High-Harmonic Generation;" Dissertation Submitted in Partial Fulfillment of the Requirements for the Degree of Doctor of Philosophy (Applied Physics) in the University of Michigan, 2000; 126 pages.
Baltuška, Andrius et al.; "Visible Pulse Compression to 4 fs by Optical Parametric Amplification and Programmable Dispersion Control;" Optics Letters, vol. 27, No. 5, Mar. 1, 2002, pp. 306-308.
Feurer, T., et al.; "Coherent Control Over Collective Polariton Excitations: The Dawn of Polaritonics;" 2002 Thirteenth International Conference on Ultrafast Phenomena, Technical Digest (Tops vol. 72); Opt. Soc. America; XP008086358; pp. 541-545.
Sato, Masamichi, et al.; "Adaptive Pulse Shaping of Femtosecond Laser Pulses in Amplitude and Phase Through a Single-Mode Fiber by Referring to Frequency-Resolved Optical Gating Patterns;" Jpn. J. Appl. Phys., vol. 41 (2002); Part 1 No. 6A, Jun. 2002; XP-002436366; pp. 3704-3709.
Gee, S., et al.; "Ultrashort Pulse Generation by Intracavity Spectral Shaping and Phase Compensation of External-Cavity Modelocked Semiconductor Lasers;" IEEE Journal of Quantum Electronics, vol. 36, No. 9, Sep. 2000; XP-002462407; pp. 1035-1040.
Scaffidi, J., et al.; "Spatial and Temporal Dependence of Interspark Interactions in Femtosecond-Nanosecond Dual-Pulse Laser-Induced Breakdown Spectroscopy;" Applied Optics, vol. 43, No. 27, Sep. 20, 2004; XP-002462408; pp. 5243-5250.
Pfeiffer, W., et al.; "Ultrafast Spatio-Temporal Near-Field Control;" IEEE 2005 European Quantum Electronics Conference, 0-7803-8973-5/05; p. 169 (1 page).
Sukharev, Maxim et al.; "Coherent Control Approaches to Light Guidance in the Nanoscale;" The Journal of Chemical Physics 124, 2006; XP008086379; pp. 144707-1-144707-8.
Akozbek, N. et al.; "Continuum Generation of the Third-Harmonic Pulse Generated by an Intense Femtosecond IR Laser Pulse In Air;" Applied Physics B (Lasers and Optics), Springer-Verlag, Germany, vol. B77, No. 2-3, XP002476096; Sep. 2003; pp. 177-183.
Lozovoy, V. V. et al.; "What Role Can Four-Wave Mixing Techniques Play in Coherent Control?;" Advances in Multiphoton Processes and Spectroscopy 14; and Quantum Control of Molecular Reaction Dynamics, edited by R. J. Gordon and Y. Fujimura, World Scientific, Singapore, 2000; pp. 62-79.
Dantus, Marcos; "Laser Control of Chemical Reactions;" Chemical & Engineering News, vol. 79, 2001; p. 191.
Pastirk, I. et al.; "Quantum Control of the Yield of a Chemical Reaction;" J. Chem. Phys., vol. 108, No. 11, Mar. 15, 1998; pp. 4375-4378.
Pastirk, I. et al.; "Sequences for Controlling Laser Excitation With Femtosecond Three-Pulse Four-Wave Mixing;" The Royal Society of Chemistry, vol. 113, 1999; pp. 401-424.
Pastirk, I. et al.; "Femtosecond Ground State Dynamics of Gas Phase $N^2O^4$ and $NO^2$;" Chemical Physics Letters, vol. 349, Nov. 23, 2001; pp. 71-78.
Pastirk, I. et al.: "Control and Characterization of Intramolecular Dynamics With Chirped Femtosecond Three-Pulse Four-Wave Mixing;" J. Phys. Chem. A, vol. 103, No. 49, Sep. 23, 1999; pp. 10226-10236.
Pastirk, I. et al.; "Femtosecond Photon Echo and Virtual Echo Measurements of the Vibronic and Vibrational Coherence Relaxation Times of Iodine Vapor;" Chemical Physics Letters, vol. 333, Jan. 5, 2001; pp. 76-82.

(56) References Cited

OTHER PUBLICATIONS

Dantus, Marcos; "Ahmed Zewail, Nobel Laureate in Chemistry;" European Photochemistry Association (EPA) Newsletter, No. 69, Jul. 2000; 5 pages.
Brown, E. J. et al.; "Femtosecond Transient-Grating Techniques: Population and Coherence Dynamics Involving Ground and Excited States;" J. Chem. Phys., vol. 110, No. 12, Mar. 22, 1999; pp. 5772-5788.
Brown, E. J. et al.; "Population and Coherence Control by Three-Pulse Four-Wave Mixing;" J. Chem. Phys., vol. 111, No. 9, Sep. 1, 1999; pp. 3779-3782.
Brown, E. J. et. al. "Ultrafast Rotational Anisotropy Measurements: Strong-Field Nonlinear Saturation Effects;" J. Phys. Chem. A, vol. 105, No. 34, 2001; pp. 8004-8010.
Brown, E. J. et. al. "Ultrafast Rotational Anisotropy Measurements: Unidirectional Detection;" J. Phys. Chem. A, vol. 103, No. 16, 1999; pp. 2912-2916.
Comstock, M. et al.; "Ultrafast Transient-Grating Study of Molecules After High Intensity Excitation;" in Ultrafast Phenomena XII, 2000; 2 pages.
Comstock, M. et al.; "Ultrafast Laser Induced Molecular Alignment and Deformation: Experimental Evidence From Neutral Molecules and From Fragment Ions;" J. Phys. Chem. A, vol. 107, No. 40, 2003; pp. 8271-8281.
Comstock, M. et al.; "Femtosecond Photon Echo Measurements of Electronic Coherence Relaxation Between the $X(^1E_g+)$ and $B(^3II_{0u}+)$ states of $I_2$ in the Presence of He, Ar, $N_2$, $O_2$, $C_3H_8$;" J. Chem. Phys., vol. 119, No. 13, Oct. 1, 2003; pp. 6546-6553.
Comstock, M. et al.; "Rotational Wavepacket Revivals for Phase Modulation of Ultrafast Pulses;" Chemical Physics Letters, 372, 2003; pp. 739-744.
Rosker, M. J. et al.; "Femtosecond Clocking of the Chemical Bond;" Science, vol. 241, Sep. 2, 1988; pp. 1200-1202.
Rosker, M. J. et al.; "Femtosecond Real-Time Probing of Reactions. I. The Technique;" J. Chem. Phys., vol. 89, No. 10, Nov. 15, 1988; pp. 6113-6127.
Zhang, Q. et al.; "Femtosecond Dynamics of Photoinduced Molecular Detachment From Halogenated Alkanes. II. Asynchronous Concerted Elimination of $I_2$ From $CH_2I_2$;" J. Chem. Phys., vol. 109, No. 11, Sep. 15, 1998; pp. 4428-4442.
Zhang, Q. et al.; "Concerted Elimination Dynamics From Highly Excited States;" Faraday Discussions, 108, 1997; pp. 63-80.
Waner, M. J. et al.; "Imaging the Molecular Dimensions and Oligomerization of Proteins At Liquid/Solid Interfaces;" J. Phys. Chem. B, vol. 102, No. 9, 1998; pp. 1649-1657.
Choi, K-S et al.; "Charge Density Wave Caused by Reducing $ThSe_3$ by One Electron. Superstructure and Short-Range Order in $ATh_2Se_6$ (A = K, Rb) Studied by X-Ray Diffraction, Electron Diffraction, and Diffuse Scattering;" J. Am. Chem. Soc., vol. 120, No. 41, 1998; pp. 10706-10714.
Grimberg, B. I. et al.; "Ultrafast Nonlinear Spectroscopic Techniques in the Gas Phase and Their Density Matrix Representation;" J. Phys. Chem. A, vol. 106, No. 5, Feb. 7, 2002; pp. 697-718.
Gross, P. et al.; "Femtosecond Photoassociation: Coherence and Implications for Control in Bimolecular Reactions;" J. Chem. Phys., vol. 106, No. 19, May 15, 1997; pp. 8013-8021.
Peng, L. W. et al.; "Stepwise Solvation of the Intramolecular-Charge-Transfer Molecule *p*-(Dimethylamino)benzonitrile;" J. Phys. Chem., 91, 1987, p. 6162.
Marvet, Una et al.; "Femtosecond Dynamics of Unimolecular and Unrestricted Bimolecular Reactions;" J. Phys. Chem. A, vol. 102, No. 23, 1998; pp. 4111-4117.
Marvet, Una et al.; "Femtosecond Dynamics of Photoinduced Molecular Detachment From Halogenated Alkanes. I. Transition State Dynamics and Product Channel Coherence;" J. Chem. Phys., vol. 109, No. 11, Sep. 15, 1998.
Marvet, Una et al.; "Femtosecond Concerted Elimination of Halogen Molecules From Halogenated Alkanes;" Phys. Chem. Chem. Phys., 2, 2000; pp. 885-891.
Marvet, Una et al.; "Femtosecond Observation of a Concerted Chemical Reaction;" Chemical Physics Letters, 256, Jun. 21, 1996; pp. 57-62.
Marvet, Una et al.; "Femtosecond Photoassociation Spectroscopy: Coherent Bond Formation;" Chemical Physics Letters, 245, Nov. 3, 1995; pp. 393-399.
Dantus, Marcos; "Femtosecond Laser Pulses: Principles and Experiments;" (Book Review) J. Am. Chem. Soc., vol. 121, No. 37, 1999; pp. 8677-8678.
Dantus, Marcos et al.; "Ultrafast Spectroscopy;" Encyclopedia of Applied Physics, vol. 22, 1998; pp. 431-456.
Dantus, Marcos et al.; "Femtosecond Laser Observations of Molecular Vibration and Rotation;" Nature, vol. 343, Feb. 22, 1990; pp. 737-739.
Dantus, Marcos et al.; "Femtosecond Real-Time Probing of Reactions. V. The reaction of IHgl;" J. Chem. Phys., vol. 91, No. 12, Dec. 15, 1989; pp. 7437-7450.
Dantus, Marcos et al.; "Femtosecond Real-Time Probing of Reactions. II. The Dissociation Reaction of ICN;" J. Chem. Phys., vol. 89, NO. 10, Nov. 15, 1988; pp. 6128-6140.
Dantus, Marcos et al.; "Real-Time Femtosecond Probing of "Transition States" In Chemical Reactions;" J. Chem. Phys., vol. 87, No. 4, Aug. 15, 1987; pp. 2395-2397.
Dantus, Marcos; "Ultrafast Probing and Control of Molecular Dynamics: Beyond the Pump-Probe Method;" Femtochemistry Wiley-VCH, Weinheim, 169, 2000; 35 pages.
Lozovoy, V. V. et al.; "Photon Echo Pulse Sequences With Femtosecond Shaped Laser Pulses As a Vehicle for Molecule-Based Quantum Computation;" J. Chemical Physics Letters 351, Jan. 10, 2002; pp. 213-221.
Lozovoy, V. V. et al.; "Systematic Control of Nonlinear Optical Processes Using Optimally Shaped Femtosecond Pulses;" ChemPhysChem, Wiley-VCH Verlag GmbH & Co. KGaA, Weinheim, 6, 2005; pp. 1970-2000.
Lozovoy, V. V. et al.: "Multiphoton Intrapulse Interference. IV. Ultrashort Laser Pulse Spectral Phase Characterization and Compensation;" Optics Letters, vol. 29, No. 7, Apr. 1, 2004; pp. 775-777.
Lozovoy, V. V. et al.; "Cascaded Free-Induction Decay Four-Wave Mixing;" Chemical Physics 266, 2001, pp. 205-212.
Lozovoy, V. V. et al.; "The Role of Pulse Sequences in Controlling Ultrafast Intramolecular Dynamics With Four-Wave Mixing;" Int. Rev. In Physical Chemistry, vol. 19, No. 4, 2000; pp. 531-552.
Lozovoy, V. V. et al.; "The Role of Microscopic and Macroscopic Coherence in Laser Control;" Chemical Physics 267, 2001; pp. 99-114.
Lozovoy, V. V. et al.; "Femtosecond Spectrally Dispersed Three-Pulse Four-Wave Mixing: The Role of Sequence and Chirp in Controlling Intramolecular Dynamics;" J. Raman Spectroscopy 31, 2000; pp. 41-49.
Pastirk, I. et al.; "2D (time-frequency) Femtosecond Four-Wave Mixing At $10^{14}$ W/cm$^2$: Molecular and Electronic Response;" Symposium on Optical Pulse and Beam Propagation III, Photonics West, 2001; 3 pages.
"Shape Your Pulses. Control Your Experiment." advertisement, Laser Focus World, (Dec. 1997) p. 26, CRI, Inc.
A. Glass et al.; "Control of the photodissociation of CsCI"; Applied Physics B 71; 2000; pp. 267-276.
Allison Albrecht Ferro et al.; "Complete femtosecond linear free induction decay, Fourier algorithm for dispersion relations and accuracy of the rotating wave approximation"; Journal of Chemical Physics, vol. 114, No. 10; Mar. 8, 2001; pp. 4649-4656.
Barry, Liam P., et al., "A High-Speed Optical Star Network Using TDMA and All-Optical Demultiplexing Techniques", IEEE Journal on Selected Areas in Communications, vol. 14, No. 5, (Jun. 1996), pp. 1030-1038.
Christopher J. Bardeen et al.; "Using time-dependent rate equations to describe chirped pulse excitation in condensed phases"; Chemical Physics Letters 302; 1999; pp. 405-410.
Cumpston, B.H. et al.; "New Photopolymers based on Two-Photon Absorbing Chromophores and Application to Three-Dimensional Microfabricaton and Optical Storage"; Mat. Res. Soc. Symp. Proc; vol. 488; 1998; pp. 217-225.

(56) References Cited

OTHER PUBLICATIONS

Cumpston,B.H. et al.; "Two-photon polymerization initiators for three-dimensional optical data storage and microfabrication"; Letters to Nature; vol. 398; Mar. 4, 1999; pp. 51-54.
D. Lalovic et al.; "Quantum mechanics in terms of non-negative smoothed Wigner functions"; Physical Review A, vol. 46, No. 3; Aug. 1, 1992; pp. 1206-1212.
David C. Clary; "Quantum Theory of Chemical Reaction Dynamics"; Science, vol. 279, Mar. 20, 1998; p. 1879.
Delfyett, Peter J., et al., "High-Power Ultrafast Laser Diodes", IEEE Journal of Quantum Electronics, vol. 28, No. 10, (Oct. 1992), pp. 2203-2219.
Dreischuh, A., Experimental Demonstraction of Pulse Shaping and Shortening by Spatial Filtering of an Induced-Phase-Modulated Probe Wave, IEEE Journal of Quantum Electronics, vol. 33, No. 3, (Mar. 1997), pp. 329-335.
Dugan, M.A., et al., "High-resolution acousto-optic shaping of unamplified and amplified femtosecond laser pulses", J. Opt. Soc. Am. B, vol. 14, No. 9, (Sep. 1997), pp. 2348-2358, Optical Society of America.
Efimov, a., et al., "Programmable shaping of ultrabroad-bandwidth pulses from a Ti:sapphire laser", Journal B/vol. 12, No. 10 (Oct. 1995) pp. 1968-1980, Optical Society of America.
Fermann, M.E., et al., "Additive-pulse-compression mode locking of a neodymium fiber laser", Optics Letters, vol. 16, No. 4, (Feb. 15, 1991), Optical Society of America.
Fetterman, et al., "Ultrafast pulse shaping: amplification and characterization", Optics Express, vol. 3, No. 10, (Nov. 9, 1998), pp. 366-375.
Fork, R.L., et al., "Compression of optical pulses to six femtoseconds by using cubic phase compensation", Optics Letters, (Jul. 1987), vol. 12, No. 7, Optical Society of America.
Gomes, A.S.L., et al., "Optical fibre-grating pulse compressors", Tutorial Review, Optical and Quantum Electronics 20, (1988), pp. 95-112.
Haner, M., et al., "Generation of programmable, picosecond-resolution shaped laser pulses by fiber-grating pulse compression", Optics Letters, vol. 12, No. 6, (Jun. 1987), pp. 398-400, Optical Society of America.
Heritage, J.P., "Picosecond pulse shaping by spectral phase and amplitude manipulation", Optics Letters, vol. 10, No. 12, (Dec. 1985), pp. 609-611, Optical Society of America.
J.P. Ogilvie et al.; "Fourier transform measurement of two-photon excitation spectra: applications to microscopy and optimal control"; Optics Letters, vol. 30, No. 8; Apr. 15, 2005; pp. 911-913.
Jianshu Cao et al.; "A simple physical picture for quantum control of wave packet localization"; J. Chem Phys., 107; Aug. 1, 1997; pp. 1441-1450.
K.D. Belfield et al.; "Multiphoton-absorbing organic materials for microfabrication, emerging optical applications and non-destructive three-dimensional imaging"; J. of Phys. Organic Chem., 13; 2000; pp. 837-849.
Kapteyn, Henry C. et al.; "A Comparison of Multipass Vs. Regenerative Ti:Sapphire Laser Amplifiers;" Kapteyn-Murnane Laboratories Inc, Boulder, CO, USA, www.kmlabs.com; 2 pages.
Konorov, S.O., "Laser Breakdown with Millijoule Trains of Picosecond Pulses Transmitted through a Hollow-Core Photonic-Crystal Fiber", Laser Physics, vol. 13, No. 4, (2003) pp. 652-656.
Kosik, Ellen M., et al., "The effects of noise on ultrashort optical pulse measurement using SPIDER"; The Institute of Optics, University of Rochester, Rochester, NY; (2000) pp. 21-23.
Krausz, F., et al., "Generation of 33-fs optical pulses from a solid-state laser", Optics Letters, (Feb. 1, 1992), vol. 17, No. 3, Optical Society of America.
Lemoff, B.E., et al., "Quintic-phase-limited, spatially uniform expansion and recompression of ultrashort optical pulses", Optics Letters, vol. 18, No. 19, (Oct. 1, 1993), pp. 1651-1653, Optical Society of America.
Liu, Yongqian, et al., "Terahertz Waveform Synthesis via Optical Pulse Shaping", IEEE Journal of Selected Topics in Quantum Electronics, (Sep. 1996), vol. 2, No. 3, pp. 709-719.
Lu, Y.M. et al.; "Highly sensitive two-photon chromophores applied to three dimensional lithographic microfabrication: design, synthesis and characterization towards two-photon absorbtion cross section"; J. Mater Chem. 14(1); 2004; pp. 75-80.
M. Ovchinnikov et al.; "Semiclassical molecular dynamics computation of spontaneous light emission in the condensed phase: Resonance Raman spectra"; Journal of Chemical Physics, vol. 114, No. 16; Apr. 22, 2001; pp. 7130-7143.
Meshulach, D., et al., "Adaptive Compression of Femtosecond Pulses", presented at the Ultrafast Optics 1997 Conference, Aug. 1997, Monterey California (3 pages).
Nisoli, M., et al., "Compression of high-energy laser pulses below 5fs", Optics Letters, (Apr. 15, 1997) vol. 22, No. 8, pp. 522-524, Optical Society of America.
Perry, Michael D., et al., "Terawatt to Petawatt Subpicosecond Lasers", Articles, (May 13, 1994), vol. 264, Science.
Postnikova, B.J. et al.; "Towards nanoscale three-dimensional fabrication using two-photon initiated polymerization and near-field excitation"; Microelectron. Eng. 69 (2-4); Sep. 2003; pp. 459-465.
Quiroga-Teixeiro, M.L., et al., "Compression of optical solitons by conversion of nonlinear modes", J. Opt. Soc. Am. B, vol. 12, No. 6, (Jun. 1995), pp. 1110-1116, Optical Society of America.
R. Teets et al.; "Coherent Two-Photon Excitation by Multiple Light Pulses"; Physical Review Letters, vol. 38, No. 14; Apr. 4, 1977; lags. 760-764.
Wolleschensky et al.; "Characterization and Optimization of a Laser-Scanning Microscope in the Femtosecond Regime;" Applied Physics B 67, Lasers and Optics, 1998; pp. 87-94.
Reitze, D.H., et al., "Shaping of wide bandwidth 20 femtosecond optical pulses", Appl. Phys. Lett. 61 (11), (Sep. 14, 1992), pp. 1260-1262, American Institute of Physics.
Yeremenko et al.; "The criterion of pulse reconstruction quality based on Wigner representation"; Applied Physics B 70 (Suppl); 2000; pp. S109-S117.
ScanMail 10K—Scanna; Internet publication from Safer America; 2003.
Spielmann, C., et al., "Ti: Sapphire Laser Produces Intense Sub-5-FS Pulses", Laser Focus World, May 97, vol. 33, Issue 5, p. 127.
Sun, H.B. et al.; "Two-photon laser precision microfabrication and its applications to micronano devices and systems"; J. Lightwave Technol. 21(3); Mar. 2003; pp. 624-633.
Szipöcs, Robert, et al., "Chirped multilayer coatings for broadband dispersion control in femtosecond lasers", Optics Letters, (Feb. 1, 1994), vol. 19, No. 3, Optical Society of America.
T. Okada et al.; "Optical control of two-photon excitation efficiency of $\alpha$-perylene crystal by pulse shaping"; Amer. Inst. of Phys., vol. 121, No. 13; Oct. 1, 2004; pp. 6386-6391.
Trebino, Rick, et al., "Using phase retrieval to measure the intensity and phase of ultrashort pulses: frequency-resolved optical gating", J. Opt. Soc. Am. A, vol. 10, No. 5, (May 1993), pp. 1101-1111, Optical Society of America.
Umstadter, D., et al., "Nonlinear Plasma Waves Resonantly Driven by Optimized Laser Pulse Trains", Physical Review Letters, vol. 72, No. 8, (Feb. 21, 1994), pp. 1224-1227, The American Physical Society.
Warren, W.S., et al., "Coherent Control of Quantum Dynamics: The Dream is Alive", Articles, Science, (Mar. 12, 1993), vol. 259.
Wefers, Marc M., "Programmable phase and amplitude femtosecond pulse shaping", Optics Letters (Dec. 1, 1993), vol. 18, No. 23, pp. 2032-2034.
Wefers, Marc, et al., "Generation of high-fidelity programmable ultrafast optical waveforms", Optics Letters, (May 1, 1995), vol. 20, No. 9, Optical Society of America.
Weiner, "Encoding and decoding of femtosecond pulses", Optics Letters, (Apr. 1988), vol. 13, No. 4, Optical Society of America.
Weiner, A.M., "Enhancement of coherent charge oscillations in coupled quantum wells by femtosecond pulse shaping", J. Opt. Soc. Am. B, vol. 11, No. 12, (Dec. 1994), pp. 2480-2491, Optical Society of America.

(56) References Cited

OTHER PUBLICATIONS

Weiner, A.M., "Femtosecond Optical Pulse Shaping and Processing", Prog. Quant. Electr. (1995) vol. 19, pp. 161; 230-233.
Weiner, A.M., "High-resolution femtosecond pulse shaping", J. Opt. Soc. Am. B., vol. 5, No. 8, (Aug. 1988), pp. 1563-1572, Optical Society of America.
Weiner, A.M., "Programmable femtosecond pulse shaping by use of a multielement liquid-crystal phase modulator", Optics Letters, Optics Letters, (Mar. 15, 1990), vol. 15, No. 6, pp. 326-328, Optical Society of America.
Weiner, A.M., "Spectral holography of shaped femtosecond pulses", Optics Letters, vol. 17, No. 3 (Feb. 1, 1992), pp. 224-226, Optical Society of America.
Weiner, A.M., et al., "Femtosecond multiple-pulse impulsive stimulated Raman scattering spectroscopy", J. Opt. Soc. Am. B., vol. 8, No. 6, (Jun. 1991), pp. 1264-1275.
Weiner, Andrew M., Programmable Shaping of Femtosecond Optical Pulses by Use of 128-Element Liquid Crystal Phase Modulator, (1992) vol. 28, No. 4, pp. 908-919, IEEE Journal of Quantum Electronics.
Xu, J.H., et al., "Study of Pulse Compression from 1.5 μm Distributed Feedback Lasers by a Gires-Tournois Interferometer", Fiber and Integrated Optics, vol. 13, (1994), pp. 365-372.
Yang, W. et al.; "High-ratio Electro-optical Data Compression for Massive Accessing Networks Using AOM-based Ultrafast Pulse Shaping"; Journal of Optical Communications; vol. 22, No. 1; 2001; pp. 694-697.
Yu-Chen Shen et al.; "What can short-pulse pump-probe spectroscopy tell us about Franck-Condon dynamics?"; Journal of Chemical Physics, vol. 110. No. 20; May 22, 1999; pp. 9793- 9806.
Zhou, Jianping, et al., "Generation of 21-fs millijoule-energy pulses by use of Ti:sapphire", Optics Letters, vol. 19, No. 2, (Jan. 15, 1994), pp. 126-128, Optical Society of America.
Zeek, E. et al., "Pulse Compression by Use of Deformable Mirrors," Optics Letters, OSA, Optical Society of America, vol. 24, No. 7, Apr. 1, 1999, pp. 493-495.
Sardesai, H et al. "A Femtosecond Code-Division Multiple-Access Communication System Test Bed," Journal of Lightwave Technology, IEEE Service Center, vol. 16, No. 11, Nov. 1, 1998, p. 1953-1964.
"BNSs Liquid Crystal Solutions Spatial Light Modulators 1 × 12,288 Linear Series," brochure, Apr. 2006, Boulder Nonlinear Systems, Inc., pp. 1-4.
Alexeev, I. et al., "Ultraviolet Light Generation by Intense Laser Filaments Propagating in Air," Conference on Lasers & Electro-Optics (CLEO), Baltimore, Maryland, USA, XP010876479; May 22-27, 2005, pp. 189-191.
Aviv Circular Dichroism Spectrometer, Model 400, Aviv Biomedical, Inc., http://www.avivbiomedical.com, Nov. 29, 2006; 2 pages.
Brixner, T., et al., "Adaptive Shaping of Femtosecond Polarization Profiles," J. Opt. Soc. Am. B. vol. 20, No. 5, May 2003; pp. 878-881.
Brixner, T., et al., "Femtosecond Polarlization Pulse Shaping," Optics Letters, vol. 26, No. 8, Apr. 15, 2001; pp. 557-559.
Butcher, Steve, et al., "Multiphoton approach shapes ultrafast pulses," Pulse Shaping, (2006) Institute of Physics and IOP Publishing Ltd., 3 pages.
Butenko, A.V. et al.; "Factals: Giant Impurity Nonlinearities in Optics of Fractal Clusters;" Z. Phys. D., 10, 1988; pp. 81-92.
CheckGate 9000—Metal detector; Internet publication from Safer America (2003) http://www.saferamerica.com/productDetail.asp?categoryID=19&productID=234; printed Oct. 6, 2004 (3 pages).
Dantus, Marcos et al., "Stereoisomer Recognition by MS with Shaped Laser Pulses," American Chemical Society. Abstracts of paper. At the national meeting, American Chemical Society, Washington, D.C., U.S. vol. 231 (Mar. 26, 2006) pp. 1-ANYL, XP009082814, ISSN: 0065-7727, the whole document.
Dantus, Marcos, et al., "MIIPS characterizes and corrects femtosecond pulses," Ultrafast Optical Systems, Laser Focus World, (May 2007) XP001539450, 4 pages.
Dela Cruz, J. M. et al.; "Coherent Control Improves Biomedical Imaging With Ultrashort Shaped Pulses;" Journal of Photochemistry and Photobiology A: Chemistry 180, Mar. 2006; pp. 307-313.
Dela Cruz, Johanna M., et al., "Multidimensional analysis with shaped femtosecond pulses: identification of conformational and geometric isomers and mixtures using mass spectrometry," American Chemical Society. Abstracts of paper. At the national meeting, American Chemical Society, Washington, D.C., U.S., vol. 230, (Aug. 28, 2005) p. U418, XP009082815, ISSN: 0065-7727, the whole document.
Dela Cruz, Johanna M., et al., "Quantitative mass spectrometric identification of isomers applying coherent laser control," Journal of Physical Chemistry A ACS USA, vol. 109, No. 38 (Sep. 29, 2005) pp. 8447-8450, XP002431289, ISSN: 1089-5639, figure 1.
Delong, K.W., et al., "Frequency Resolved Optical Gating with the Use of 2nd-Harmonic Generation." Journal of Optical Society of America B-Optical Physics, 1994. 11 (11): pp. 2206-2215.
EVD-3000®—Hand-held Explosives Detector, Internet Publication, http://www.saferamerica.com/productDetail.asp?categoryID=16 &productID=235; printed Oct. 6, 2004 (3 pages).
Fujimoto, Masatoshi, et al., "Programmable shaping of a subterawatt, femtosecond laser pulse by modulating the spectral phase of the preamplified pulse," Optics Communications, 280 (2007) ScienceDirect, pp. 404-407.
Gallmann, L., et al., "Characterization of sub-6-fs optical pulses with spectral phase interferometry for direct electric-field reconstruction," Optics Letters, vol. 24, No. 18 (Sep. 15, 1999) p. 13140-1316.
Gunaratne, T. et al.; "Influence of Bandwidth and Phase Shaping on Laser Induced Breakdown Spectroscopy With Ultrashort Laser Pulses;" Chemical Physics Letters 423, Apr. 3, 2006; pp. 197-201.
Gunn, J M et al: "Polarization and phase control of remote surface-plasmon-mediated two-photo-induced emission and waveguiding" Nano Letters American Chem. Soc. USA, vol. 6, No. 12, Aug. 2006.
Jasco Comparison Proven Spectroscopy & Chromatography Technology, J-815 Circular Dichroism Spectropolarimeter, Jasco UK, http://www.jasco.co.uk/j800.asp, Nov. 29, 2006; 2 pages.
Jiang, et al. "Spectral line-by-line pulse shaping," Optics Letters, vol. 30, No. 12 (Jun. 15, 2005) Optical Society of America, pp. 1557-1559.
Jiang, et al., "Line-by-line pulse shaping control of optical arbitrary waveform generation," Optics Express, vol. 13, No. 25, (Dec. 12, 2005) Optical Society of America, pp. 10431-10439.
Lee, P.C. et al.; "Adsorption and Surface-Enhanced Raman of Dyes on Silver and Gold Sols;" Phys. Chem., vol. 86, No. 17, 1982, pp. 3391-3395.
Lim, Sang-Hyun et al.; "Single-Pulse Phase-Control Interferometric Coherent Anti-Stokes Raman Scattering Spectroscopy;" Physical Review A, 72, (Oct. 2005); pp. 041803-1-041803-4.
Link, Stephan et al.; "Optical Properties and Ultrafast Dynamics of Metallic Nanocrystals;" Annu. Rev. Phys. Chem. 54, 2003; pp. 331-369.
Lozovoy, V. V. et al.; "Spectral Phase Optimization of Femtosecond Laser Pulses for Narrow-Band, Low-Background Nonlinear Spectroscopy;" Optics Express, vol. 13, No. 26, Dec. 26, 2005; pp. 10882-10887.
Lozovoy, V. V., et al., "Laser Control of Physicochemical Processes; Experiments and Applications," The Royal Society of Chemistry 2006, Annu. Rep. Prog. Chem, Sect. C, 102. www.rsc.org/annrepc (2006) pp. 227-258.
Midorikawa, Katsumi, et al., "Phase-Matched High-Order Harmonic Generation by Guided Intense Femtosecond Pulses," IEEE Journal of Selected Topics in Quantum Electronics, vol. 5, No. 6 (Nov./Dec. 1999) pp. 1475-1485.
Ogilvie, Jennifer P., et al., "Use of coherent control for selective two-photon fluorescence microscopy in live organisms," Optical Society of America (Jan. 2006) 8 pages.
Ohno, Kimihisa, et al., "Adaptive pulse shaping of phase and amplitude of an amplified femtosecond pulse laser by direct reference to frequency-resolved optical gating traces," J. Opt. Soc. Am. B vol. 19, No. 11 (Nov. 2002) pp. 2781-2790.

(56) References Cited

OTHER PUBLICATIONS

Parmeter, John E., et al., "Overview of Explosives Detection Research and Development in Department 5848 at Sandia National Laboratories"; 16th Annual NDA Security Technology Symposium & Exhibition; Jun. 26-29, 2000.
Pastirk, I., et al., "Multidimensional Analytical Method Based on Binary Phase Shaping of Femtosecond Pulses," J. Phys. Chem. A, vol. 109, No. 11, Feb. 23, 2005; pp. 2413-2416.
Pastirk, I., et al., "No loss spectral phase correction and arbitrary phase shaping of regeneratively amplified femtosecond pulses using MIIPS," Optics Express, vol. 14, No. 20, (Oct. 2, 2006) pp. 9537-9543.
PiStar Kinetic Circular Dichroism Spectrometer, http://www.phtophysics.com/pistar.php, Nov. 29, 2006; 3 pages.
Posthumus, J.H., "The dynamics of small molecules in intense laser fields," Reports on Progress in Physics, 67 (2004) Institute of Physics Publishing, pp. 623-665.
QWPO-AS, Zero Order Waveplates—Air Spaced, Optical Components and Assemblies, www.cvilaser.com, published Nov. 21, 2005; pp. 8-9.
Rodriguez, George, et al., "Coherent Ultrafast MI-FROG Spectroscopy of Optical Field Ionization in Molecular H2, N2, and O2," IEEE Journal on Selected Topics in Quantum Electronics, vol. 7, No. 4 (Jul./Aug. 2001) pp. 579-591.
Sanders, A. W. et al.: "Observation of Plasmon Propagation, Redirection, and Fan-Out in Silver Nanowires" Nano Letters, American Chemical Society, Washington, DC, US, vol. 6, No. 8, Jun. 28, 2006, pp. 1822-1826, XP007901978, ISSN: 1530-6984.
Sandia tests new FAA explosives—detection portal at Albuquerque International Airport; Internet publication from Safer America, Sep. 15, 1997.
Serbin, J., et al., "Femtosecond lasers as novel tool in dental surgery," applied surface science, 197-198 (2002) pp. 737-740.
Shimizu, Satoru, et al., "Spectral phase transfer for indirect phase control of sub-20-fs deep UV pulses," Optics Express, vol. 13, No. 17 (Aug. 22, 2005) pp. 6345-6353.
Siders, C.W., et al., "Blue-shifted third-harmonic generation and correlated self-guiding during ultrafast barrier suppression ionization of subatmospheric density noble gases," J. Opt. Soc. Am. B/vol. 13, No. 2 (Feb. 1996) pp. 330-335.
Stockman, Mark I. et al.; "Coherent Control of Femtosecond Energy Localization in Nanosystems;" Physical Review Letters, vol. 88, No. 6, Feb. 11, 2002; pp. 067402-1-067402-4.
Suzuki, Takayuki et al.; "Nontrivial Polarization Shaping of Femtosecond Pulses by Reference to the Results of Dual-Channel Spectral Interferomtry;" Applied Optics, vol. 43, No. 32, Nov. 10, 2004; pp. 6047-6050.
Tamaki, Y., "Phase-matched third-harmonic generation by nonlinear phase shift in a hollow fiber," Lasers and Optics Applied Physics B, vol. 67, (1998) pp. 59-63.
Ting, A., et al.; "Remote Atmospheric Breakdown for Standoff Detection by Using an Intense Short Laser Pulse," Applied Optics. Opt. Soc. America, USA, vol. 44, No. 25, XP002476098, Sep. 1, 2005; pp. 5315-5320.
Verluise, Frédéric, et al., "Arbitrary dispersion control of ultrashort optical pulses with acoustic waves," J. Opt. Soc. Am. B vol. 17, No. 1 (Jan. 2000) pp. 138-145.
von Vacano, Bernhard, et al., "Shaper-assisted collinear Spider: fast and simple broadband pulse compression in nonlinear microscopy," vol. 24, No. 5, (May 2007) J. Opt. Soc. Am. B, pp. 1091-1100.
Weiner, A.M., "Femtosecond pulse shaping using spatial light modulators," Review Article, Review of Scientific Instruments, vol. 71, No. 5 (May 2000) pp. 1929-1960.
Wollenhaupt, M. et al.; "Femtosecond Laser Photoelectron Spectroscopy on Atoms and Small Molecules: Prototype Studies in Quantum Control;" Annu. Rev. Phys. Chem., 56, 2005; pp. 25-56.
Xu, B et al.; "Quantitative Investigation of the Multiphoton Intrapuse Interference Phase Scan Method for Simultaneous Phase Measurement and Compensation of Femtosecond Laser Pulses;" J. Opt. Soc. Am. B, vol. 23, No. 4, Apr. 2006; pp. 750-759.
Brixner, T., A. Oehrlein, M. Strehle, and G. Gerber "Feedback-controlled femtosecond pulse shaping" Applied Physics B 70 [Suppl.], S119-S124 (2000).
O'Shea, Patrick, Mark Kimmel, Xun Gu, and Rick Trebino "Highly simplified device for ultrashort-pulse measurement" Optics Letter/ vol. 26, No. 12 / Jun. 15, 2001.
Zheng, Z. and A.M. Wolfe "Coherent control of second harmonic generation using spectrally phase coded femtosecond waveforms" Chemical Physics 267 (2001) 161-171 (Received Aug. 31, 2000).
Bartels R. A. et al.: "Nonresonant Control of Multimode Molecular Wave Packets at Room Temperature"; Physical Review Letters APS USA, vol. 88, No. 3, Jan. 21, 2002, pp. 033001/1-4, XP002386694, ISSN: 0031-9007.
Oron D. et al: "Quantum control of coherent anti-Stokes Raman processes"; Physical Review A (Atomic, Molecular, and Optical Physics) APS through AIP USA, vol. 65, No. 4, Apr. 2, 2002, pp. 043408/1-4, XP002386695 ISSN: 1050-2947.
Weiner A. M. et al.: "Generation of terahertz-rate trains of femtosecond pulses by phase-only filtering"; Optics Letters, OSA, Optical Society of America, Washington, D.C., US, vol. 15, No. 1, Jan. 1, 1990, pp. 51-53, XP000095196, ISSN: 0146-9592.
Cruz J. M. D. et al.: "Use of coherent control methods through scattering biological tissue to achieve functional imaging"; Proceedings of the National Academy of Sciences of the United States of America USA, vol. 101, No. 49, Dec. 7, 2004, pp. 16996-17001, XP002386696, ISSN: 0027-8424.
Bowlan, Pamela, et al., "Directly measuring the spatio-temporal electric field of focusing ultrashort pulses," Optics Express, vol. 15, No. 16 (2007) pp. 10219-10230.
Chung, Jung-Ho, "Ambiguity of Ultrashort Pulse Shapes Retrieved From the Intensity Autocorrelation and the Power Spectrum," IEEE Journal on Selected topics in Quantum Electronics, vol. 7, No. 4 (Jul./Aug. 2001) pp. 656-666.
Kubo, Atsushi, et al., "Femtosecond Imaging of Surface Plasmon Dynamics in a Nanostructured Silver Film," Nano Letters, vol. 5, No. 6 (2005) American Chemical Society, pp. 1123-1127.
Montgomery, Matthew A., "Elucidation of Control Mechanisms Discovered during Adaptive Manipulation of [Ru(dpb)3](PF6)2 emission in the Solution Phase," American Chemical Society, J. Phys. Chem. A, vol. 111, No. 8 (2007) pp. 1426-1433.
Nisoli, M., et al., "Generation of high energy 10 fs pulses by a new pulse compression technique," Appl. Phys. Lett., vol. 68, No. 20 (May 13, 1996) pp. 2793-2795.
Nuernberger, Patrick, "Femtosecond quantum control of molecular dynamics in the condensed phase," Invited Article, Physical Chemistry Chemical Physics, The Owner Societies, vol. 9 (2007) pp. 2470-2497.
Oron, Dan, et al., "Scanningless depth-resolved microscopy," Optics Express, vol. 13, No. 5 (Mar. 7, 2005).
Tada, Junji, "Adaptively controlled supercontinuum pulse from a microstructure fiber for two-photon excited fluorescence microscopy," Applied Optics, vol. 46, No. 15, (May 20, 2007) pp. 3023-3030.
Zang, Hegui, et al., "Study on Frequency-doubling Effect of the Dually Doped KTP Crystals," Journal of Synthetic Crystals vol. 29, No. 2 (May 2000).
Takasago, Kazuya, et al., "Design of Frequency-Domain Filters for Femtosecond Pulse Shaping," Part 1, No. 2A (Feb. 1996)pp. 624-629. Jpn. J. Appl. Phys.
Lim, Sang-Hyun et al., "Chemical Imaging by Single Pulse Interferometric Coherent Anti-Stokes Raman Scattering Microscopy," (2006) pp. 5196-5204. vol. 110, No. 11. J. Phys. Chem. B.
"Coherent® Silhouette, Ultrafast Pulse Shaping and Measurement," brochure, (2007) 2 pages. Coherent, Inc.
P. Main et al.; "Generation of Ultrahigh Peak Power Pulses by Chirped Pulse Amplification;" IEEE Journal of Quantum Electronics, vol. 24, No. 2, Feb. 1988; pp. 398-403.
Limpert J. et al.; "All fiber chirped-pulse amplification system based on compression in air-guiding photonic bandgap fiber;" Optics Express, vol. 11, No. 24, Dec. 1, 2003; pp. 3332-3337.
Strickland D. et al.; "Compression of amplified chirped optical pulses;" Optics Communications, vol. 56, No. 3; Dec. 1, 1985; pp. 219-221.

(56) References Cited

OTHER PUBLICATIONS

Backus S. et al.; "High power ultrafast lasers;" Review of Scientific Instruments, vol. 69, No. 3, Mar. 1998; pp. 1207-1223.
Xu L. et al.; "Experimental generation of an ultra-broad spectrum based on induced-phase modulation in a single-mode glass fiber;" Optics Communications, 162 (1999); pp. 256-260.
Weiner A.M.; "Femtosecond pulse processing;" Optical and Quantum Electronics 32, 2000; pp. 473-487.
Efimov A. et al.; "Programmable dispersion compensation and pulse shaping in a 26-fs chirped-pulse amplifier;" Optics Letters, vol. 23, No. 20, Oct. 15, 1998; pp. 1612-1614.
Foing, J.P. et al. "Femtosecond Pulse Phase Measurement by Spectrally Resolved Up-Conversion—Application to Continuum Compression," IEEE J. Quantum Electron. 28, 2285 (1992).
Rhee, T.K. et al. "Chirped-Pulse Amplification of 85-Fs Pulses at 250 Khz with 3rd-Order Dispersion Compensation by Use of Holographic Transmission Gratings," Opt. Lett. 19, 1550 (1994).
Albrecht, T.F. et al. "Chirp Measurement of Large-Bandwidth Femtosecond Optical Pulses Using 2-Photon Absorption," Opt. Commun. 84, 223 (1991).
Ranka et al., "Autocorrelation Measurement of 6-fs Pulses Based on the Two-Photon-induced Photocurrent in a GaAsP Photodiode," Opt. Lett. 22 (17), 1344-1346 (1977).
Rivet, S. et al., "Complete pulse characterization: measurements of linear and nonlinear properties" Opt. Commun. 181, 425-435 (2000).
Weiner, A.M. "Ultrafast Optics" Chapter 3 entitled "Ultrafast-Pulse Measurement Methods" (pp. 85-146), (2009).
Dantus, Marcos et al. "Two-photon microscopy with Sub-8fs laswer pulse" PDPA Frontiers in Optics/Laser Science XXVI; Oct. 24-28, 2010, pp. 1-18.
Eramo, R. et al. "Third-harmonic generation in positively dispersive gases with a novel cell", vol. 33, No. 9, Applied Optics, Mar. 20, 1994, pp. 1691-1696.

* cited by examiner

ULTRA-FAST LASER SYSTEM

CROSS REFERENCE TO RELATED APPLICATIONS

The present application claims priority to U.S. Provisional Patent Application Ser. No. 60/652,772, filed on Feb. 14, 2005, which is incorporated by reference herein.

STATEMENT OF GOVERNMENT INTEREST

This invention was made with government support under DE-FG02-01ER15143 awarded by the U.S. Department of Energy. The government has certain rights in the invention.

BACKGROUND

The present invention generally relates to a laser system and more particularly to an ultra-fast laser system using a pulse shaper.

Conventionally, lasers used for chemical analysis through spectroscopy or mass spectrometry have used a laser beam pulse where the pulse duration and wavelength are fixed and computers are employed for simple chemical analysis processes. The laser beam pulse shape and, in particular the phase of the frequencies within its bandwidth, was not considered an important parameter and was not modified; whatever fixed shape was set by the manufacturer for the laser was used in the tests. The general concept of typically laser selective ion formation from molecules in a molecular beam is disclosed in the following publication: Assion et al., "Control of Chemical Reactions by Feedback-Optimized Phase-Shaped Femtosecond Laser Pulses," Science, Vol. 282, page 919 (Oct. 30, 1998). The pulse shaping process with a learning algorithm is disclosed in Judson et al., "Teaching Lasers to Control Molecules," Physical Review Letters, Vol. 68, No. 10, page 1500 (Mar. 9, 1992). It is noteworthy, however, that the Assion article discloses use of an 80 femtosecond laser pulse and requires molecules to be isolated in a molecular beam, while the Judson article discloses use of a one nanosecond laser pulse and is purely conceptual as it does not include experimental results. Similarly, the findings by Assion et al. had great scientific interest, but the results were not sufficiently reproducible to be considered useful for analytical purposes.

There have been recent experimental attempts to purposely shape the phase of ultrashort pulses since shaped pulses have been shown to increase the yield of certain chemical reactions and multiphoton excitation, although the mechanism for the observed changes remains unknown in most cases. As usually practiced, the output waveform is determined by the Fourier transform (hereinafter "FT") of a spatial pattern transferred by a mask or a modulator array onto the dispersed optical spectrum. The introduction of liquid crystal modulator arrays and acousto-optic (hereinafter "A/O") modulators into FT pulse shapers led to computer programmable pulse shaping, with millisecond and microsecond reprogramming times, respectively, and widespread adoption of this technique. These shaped pulses require a very large data set and in many cases, complex learning calculations for determining the pulse shaping characteristics for a particular application. The optimal pulse for the particular application is not known in advance. Since the variation shape of the possible pulse shapes is huge, scanning the entire parameter space is impossible and as such the optimized pulse shape could not have been predicted by theory. For a pulse shaper with N pixels, one can generate $(P*A)^N$ shaped pulses, where P and A are the number of different phases and amplitudes a pixel can take. If it is assumed 100 pixels, each taking 10 different amplitude values and 100 different phase values, the number of different pulses is of order of magnitude $10^{300}$. This dataset is extremely large, therefore, while in principle, the field exists to achieve the desired photonic transformation or excitation, finding it is a great challenge. Some researchers have attempted to avoid such complexity by binning together every 8 pixels on the pulse shaper, thereby converting a 128 pixel shaper into one with 16 active pixel groups, but with the inherent loss of accuracy. Therefore, it would be desirable for an ultra-fast laser system to control ultrashort pulses with a smaller dataset, operable to generate very complex pulse shapes that are optimal for the particular application and are highly reproducible. The following U.S. patent publications have overcome these traditional concerns and have led to reproducible results: 2004/0233944 entitled "Laser System Using Ultra-Short Laser Pulses," published on Nov. 25, 2004; 2004/0089804 entitled "Control System and Apparatus for Use with Laser Excitation or Ionization," published on May 13, 2004; and 2003/0099264 entitled "Laser System Using Ultrashort Laser Pulses," published on May 29, 2003; all of which are incorporated by reference herein.

U.S. Patent Publication No. 2004/0145735 entitled "Coherently Controlled Nonlinear Raman Spectroscopy and Microscopy" to Silberberg et al. teaches use of a unitary pulse carrying a pump, Stokes and probe photon. This patent is incorporated by reference herein.

Additionally, monitoring the environment for chemical and biological agents, including explosives, from terrorist threats or from industrial contamination has become a necessity for reasons of national security and the well being of humans. Conventional devices are only designed for use to detect a single known agent or are inaccurate. Accordingly, to avoid a costly false positive or false negative identification, it would be desirable to employ an ultra-fast laser to environmental monitoring in order to quickly and accurately identify and/or act upon select molecules.

SUMMARY OF THE INVENTION

In accordance with the present invention, a laser system is provided which selectively excites Raman active vibrations in molecules. In another aspect of the present invention, the system includes a laser, pulse shaper and detection device. A further aspect of the present invention employs a femtosecond laser and binary pulse shaping. Still another aspect of the present invention uses a laser beam pulse, a pulse shaper and remote sensing. In yet another aspect of the present invention, a multiphoton intrapulse interference method is used to characterize the spectral phase of laser pulses and to compensate any distortions. A further aspect of the system of the present invention is employed to remotely monitor environmental chemical and biological agents or specimens, including toxins, explosives, and diseases, among others.

The laser system of the present invention is advantageous over conventional constructions since the present invention allows for remote automated analysis and identification of molecules in complex mixtures. It is envisioned that the present invention is capable of fast (for example, one second), accurate (for example, even in a chemically complex environment), robust (for example, stand alone, closed-loop and portable) and reproducible sensing. Raman active vibration sensing by the present invention provides extremely accurate and redundant identification of specimens. Operationally, the system employs a computer controlled pulse shaping module which interfaces with a commercially available femtosecond pulsed laser, a spectrometer, or a mass spectrometry module thereby using cost effective instruments. The present invention system is ideally suited for remote sensing from large distances. Furthermore, the laser system of the present invention advantageously detects and/or destroys impurities in blood, and assists in photodynamic therapy. Additional advantages and features of the present invention will become apparent from the following description and appended claims, taken in conjunction with the accompanying drawings.

DETAILED DESCRIPTION OF THE PREFERRED EMBODIMENT

An ultra-fast laser system is provided to detect chemical and biological agents in the desired environmental specimen or target area. The approach of the present invention system is based on nonlinear-laser molecule interactions that will yield uniquely selective radiant emissive signatures. The specificity of the method is built on the quantum-mechanical interaction between a shaped laser field and the electronic and molecular structure of the target. Multiphoton intrapulse interference is used to achieve high laser-molecule specificity through controlled reactivity and intramolecular energy flow. In general, three basic steps are employed. First, implementation includes a shaped femtosecond laser source coupled collinearly to a synchronized narrow bandwidth IR pulse. The shaped laser pulse will induce specific vibrational responses on the target molecule, while the narrow bandwidth IR pulse will stimulate the emission and carry a Raman signature back to the detector. Second, an arms-length identification of molecular targets is provided. Third, this technology is applied to remote molecular identification.

Figure 1:
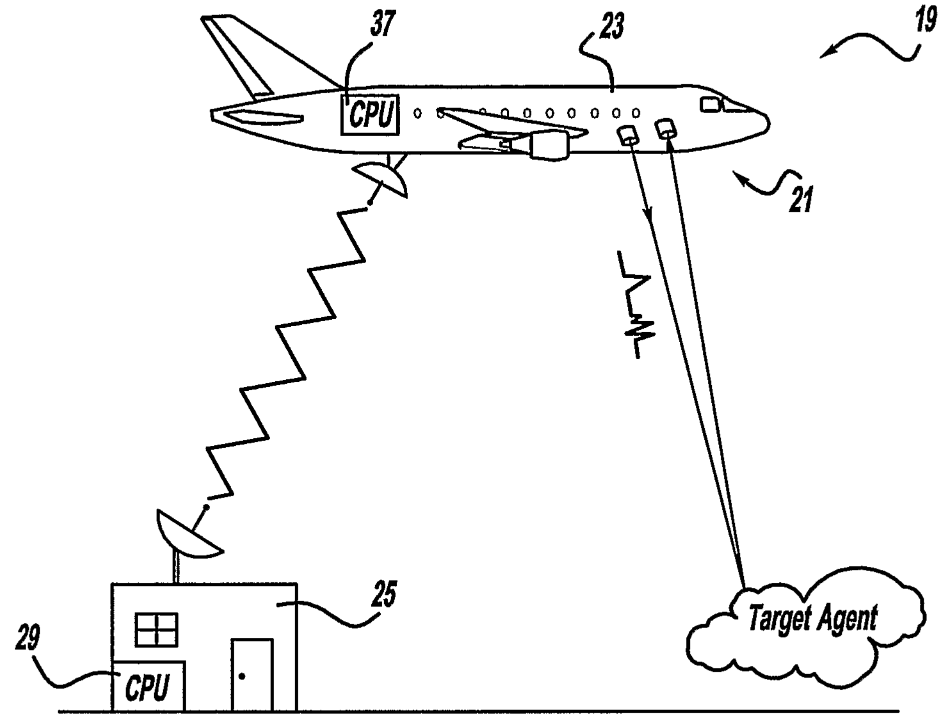
FIG. 1 is a diagrammatic view showing a preferred embodiment of a laser system of the present invention applied to remote sensing of a hazardous specimen.
Figure 8:
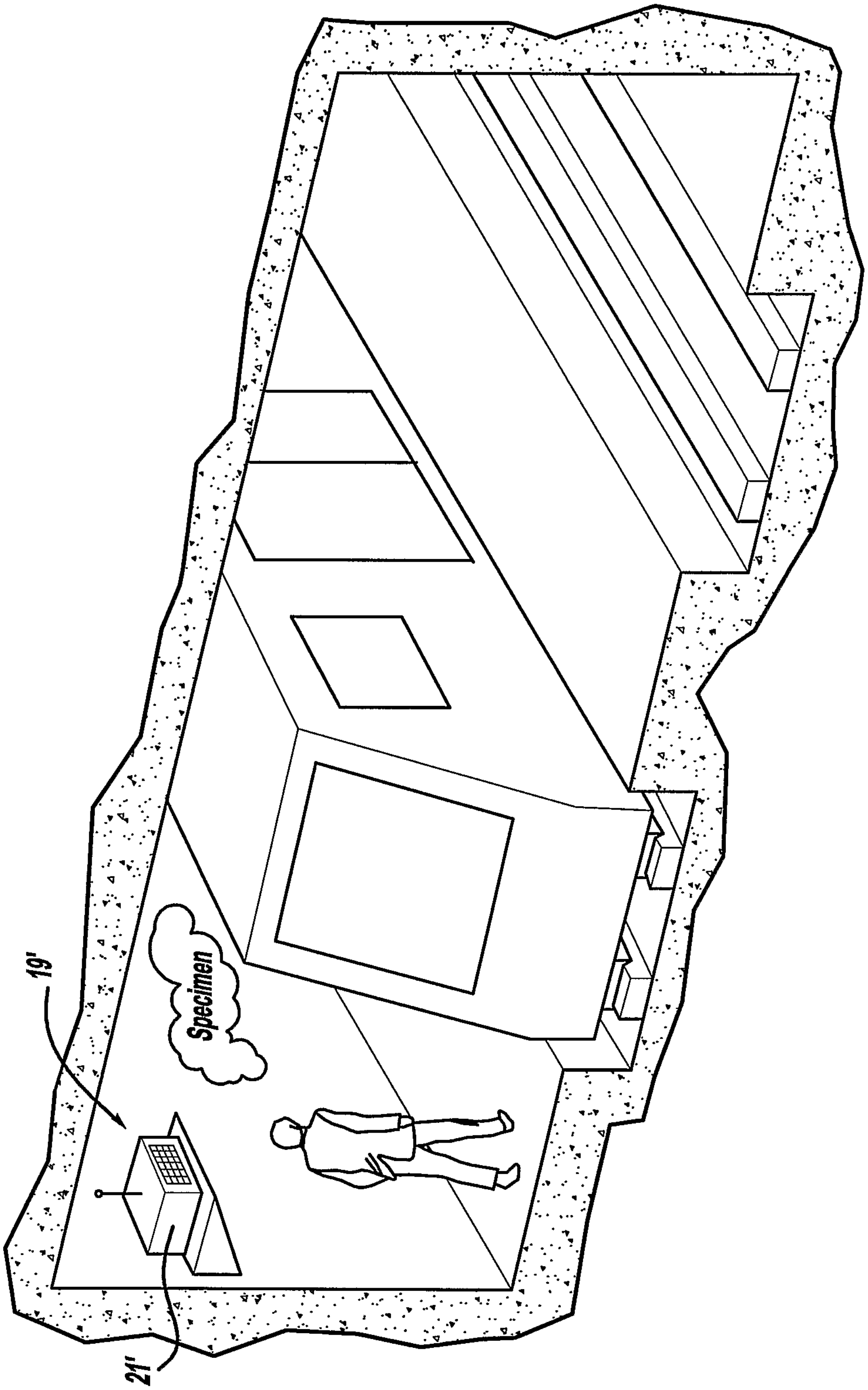
FIG. 8 is a diagrammatic, perspective view showing a first alternate embodiment of the present invention system applied to sensing of a hazardous specimen in a subway station facility.

Referring to FIG. 1, the preferred embodiment system 19 of the present invention includes a laser and detection apparatus 21 inside a remote location 23, such as an aerospace craft (including an artificial satellite, airplane, or helicopter), stationary tower or the like. A remote command center 25, such as a public safety or fire department, is also provided. Laser and detection apparatus 21 includes a femtosecond laser, pulse shaping optics, a spectrometer and a remote computer controller 37 as will be discussed in greater detail hereinafter. Computer controller 37 communicates with an emergency computer controller 29 in command center 25. Alternately, the remote facility containing a laser and detection apparatus 21' of system 19' of the present invention may be a subway station 31 (see FIG. 8), airport, building or the like.

The system is initially set up at its manufacturing facility with a library of pre-stored data of acceptable background data, unacceptable chemical and biological agent data, and the corresponding pulse shaping control data. The self-contained system 19 is subsequently installed at the remote location. System 19 is acting as an "artificial nose" in that it receives and/or analyzes air from inside the target environmental area. Upon installation and set up, and optionally at regular intervals of known-safe conditions, remote computer controller 37 senses or monitors acceptable background chemicals in the air, such as oxygen, carbon dioxide, chlorine (if adjacent a swimming pool), benzene (if adjacent a bus station or high volume street), or hexachlorobenzene (adjacent a hospital), or the like. These acceptable background chemicals are automatically stored in the memory of computer controller 37 and matched with pulse shapes and mass spectrums previously stored in the library of data. Active baseline subtraction is thereafter employed during regular environmental monitoring so these benign chemicals and their fragments are not mistakenly considered part of a dangerous compound, thereby reducing the risk of creating a false detection and warning.

Subsequently, the system automatically samples air from each environmental target area at a repetition rate of approximately one per minute, a rate which is then increased to approximately one thousand times per second if an unusual background chemical or undesirable agent is detected. The background and regularly monitored chemical analyses are stored in the computer memory for later automatic and/or manual comparisons in the event of agent detection. The varying sample rate minimizes the memory and historical trend information from becoming overwhelmed with unnecessary results, and the variable repetition rate saves laser power costs and prolongs the life of laser components and detection equipment.

If an undesirably harmful chemical or biological agent is sensed then remote computer controller 37 will automatically transmit warning and other calculated information to emergency controller 29 at command center 25. Examples of such undesirable agents include and are not limited to: methane, propane, mustard gas, nerve agents, phosgene, vinyl chloride, cyanide, anthrax and other pathogens and diseases. The present invention is advantageously expected to work on solids, liquids and gases, using spectroscopy and/or mass spectrometry. System 19 will also recalibrate itself and use multiple shaped pulses to reduce the likelihood of error, and to insure that there is no mass spec overlap of results between undesired agents and acceptable chemicals. The unit will further calculate a confidence percentage of the test results compared to an unacceptable agent believed to have been identified based on previously stored library data. If a low confidence level is determined then the unit will rapidly conduct one or more further tests on the environment within seconds of the initial noteworthy reading.

If the confidence level calculated of an undesirable agent is statistically significant then remote computer controller 37 will send the appropriate warnings and information to the command center, including currently calculated values and historical trends. This will allow for evacuation and/or countermeasures to be employed. Furthermore, the system will continue sensing all adjacent environmental areas so as to track movement and cross-contamination between environmental areas for use by emergency personnel.

On a more detailed level within the system, using wisdom based evolutionary learning calculation search methods, a series of binary phase shaped (hereinafter "BPS") laser fields is chosen to cause selective excitation of the sample through impulsive Raman scattering (hereinafter "ISRS"). The shaped pulse induces selective ISRS. This involves multiple pump-Stokes transitions but it does not involve the probe photons. This method also takes into account spontaneous emissions that will take place as a result of the intense shaped laser pulse. The BPS phase functions are based on quasi random number sequences that achieve much higher selectivity than periodic functions. The wisdom based evolutionary searches are used to combine knowledge of the chemical agent and map the resulting signals as a function of binary phase functions to determine the optimum excitation. The radiant emissions resulting from BPS-ISRS (mainly in the infrared) will be registered through coherent anti-Stokes Raman scattering and will be used to identify each chemical or biological agent of interest. The selectivity of BPS-ISRS is based on reproducible control of chemical reactivity and energy flow using BPS and mass spectrometry. Detection will also be improved by using an IR pulse to carry the anti-Stokes emission instead of using a UV laser for resonance Raman detection. Significantly, BPS-ISRS produces distinctly different radiant signatures for the identification of chemical or biological samples. The system uses Raman active vibration detection and identification of scattered electromagnetic radiation and scattering of light wavelengths when the molecular specimen is struck by the shaped laser beam pulse(s). The multidimensional analytical tool will thus be used for remote identification. This BPS-ISRS system of the present invention is then incorporated into a field-ready module, such as apparatus 21 or 21', capable of detection of contaminants even in the presence of a chemically complex environment.

The shaped laser pulse will induce a number of nonlinear optical excitations in the sample molecule. These lead to spontaneous and coherent emission. The spontaneous emission identified as fluorescence and phosphorescence from excited electronic states, as well as spontaneous Raman emission. Under strong field excitation, plasma is formed and atomic emissions are observed as well. The coherent emission is mainly identified as the coherent anti-Stokes Raman signal. Both spontaneous and coherent emissions will be recorded and used for identification purposes. This is employed for laser induced breakdown spectroscopy as well as BPS-ISRS.

Furthermore, operational parameters such as ultimate sensitivity are initially obtained: once a number of pre-determined shaped laser pulses (as more fully described hereinafter for the library) are found for a given molecule, together with the TL pulse (also as more fully described hereinafter for the library), the system is ready to make a positive identification of that particular chemical. In fact, every time the measurement is performed with a different pulse shape, the accuracy is improved exponentially with the number of independent measurements. This multidimensional analysis of the present invention is believed to make it a million times more accurate than presently used mass spectrometry units. The goal is to build a library of multidimensional spectra that result from shaped laser pulses that have been optimized for maximum contrast for each given chemical or biological threat agent (and their analogs). It is important to optimize the pulses for each molecule, because each molecule has a distinct electronic and nuclear structure that determines its susceptibility for ionization and fragmentation. It is noteworthy again that the evolutionary learning program searches and database building will only be used in a laboratory setting and not in the field with the preferred embodiment system.

The present invention pulse shaper monitoring of the environment will be carried out as follows. Every second, the system will obtain a mass spectrum using TL pulses. Under these conditions, the system is at its highest sensitivity. If a mass spectrum indicates that a possible chemical agent is present, the system immediately narrows the list of possibilities based on the available TL mass spectrum and performs tests with the first three fields defined in the library for the suspected chemical agents. These subsequent tests are run at the maximum repetition rate. Within seconds the unit should have confirmation of the suspected chemical agent(s) present. At this point the system runs a calibration test to make sure that the laser, shaper and mass spectrometer are operating within specifications. The system performs three additional measurements with the final three shaped laser pulses for a final and definitive determination. If the identification is positive for a known threat, the system contacts a command center and uplinks the experimental data used to make the determination. The command center has the required information to make the best strategic decision based on solid information within a minute of detection. Additional rounds of tests can be requested from the command center, with each full cycle taking less than one minute to complete. The speed and efficiency of the method is achieved by having previously determined the six best shaped laser pulses for each molecule. The pulse shapes in the library are determined using the automated evolutionary learning program in a laboratory setting. Updated pulse shape libraries are periodically uploaded to the remote computer controller of the field system.

Figure 3:
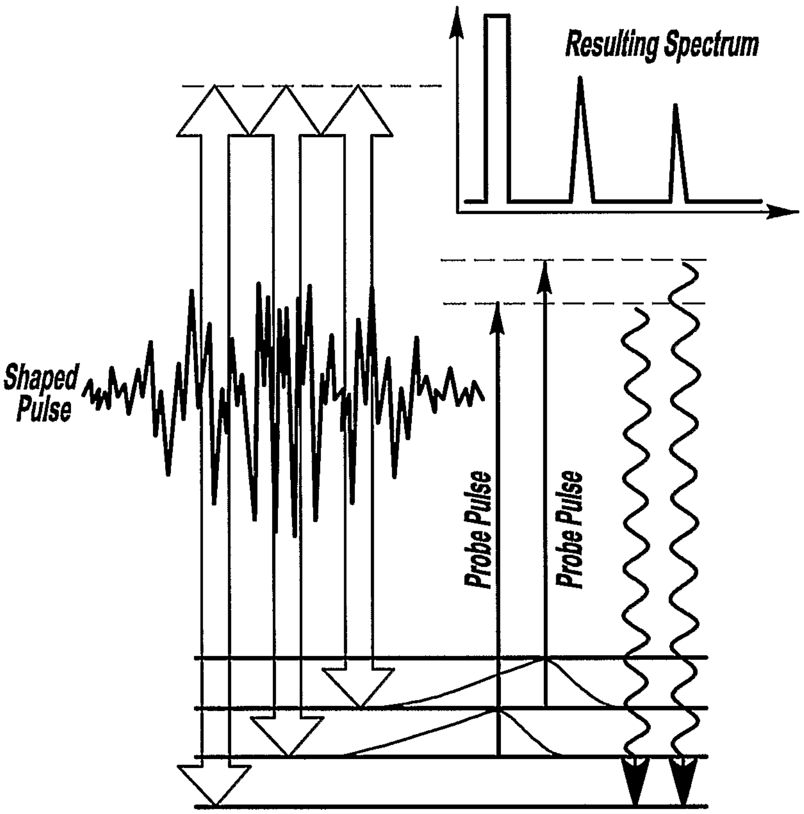
FIG. 3 is a schematic representation showing the ISRS process induced by a shaped pulse used with the preferred embodiment system.

Remote sensing will require the sensitive detection of specific nonlinear excitation of the target molecules induced by BPS-ISRS. In essence, the laser controls the excitation and energy flow in the target molecule to yield specific excitation. The molecular emissions coherent and incoherent will be recorded for identification. If the incoherent emissions are too weak and lost in the background, then detection of the coherent emissions will be accomplished using a narrow bandwidth IR laser, synchronized with the excitation pulse to stimulate the emission and carry the anti-Stokes signal back to the detector. The spectroscopic information (in other words, a signature) can then be used to identify the target molecule based on a database of elicited responses. This is represented in FIG. 3 where a narrow bandwidth laser is used to probe the excitation of the vibrational bands. The result of selective BPS-ISRS is more clearly observed in the anti-Stokes spectrum, as shown schematically in the upper right corner.

Figure 2:
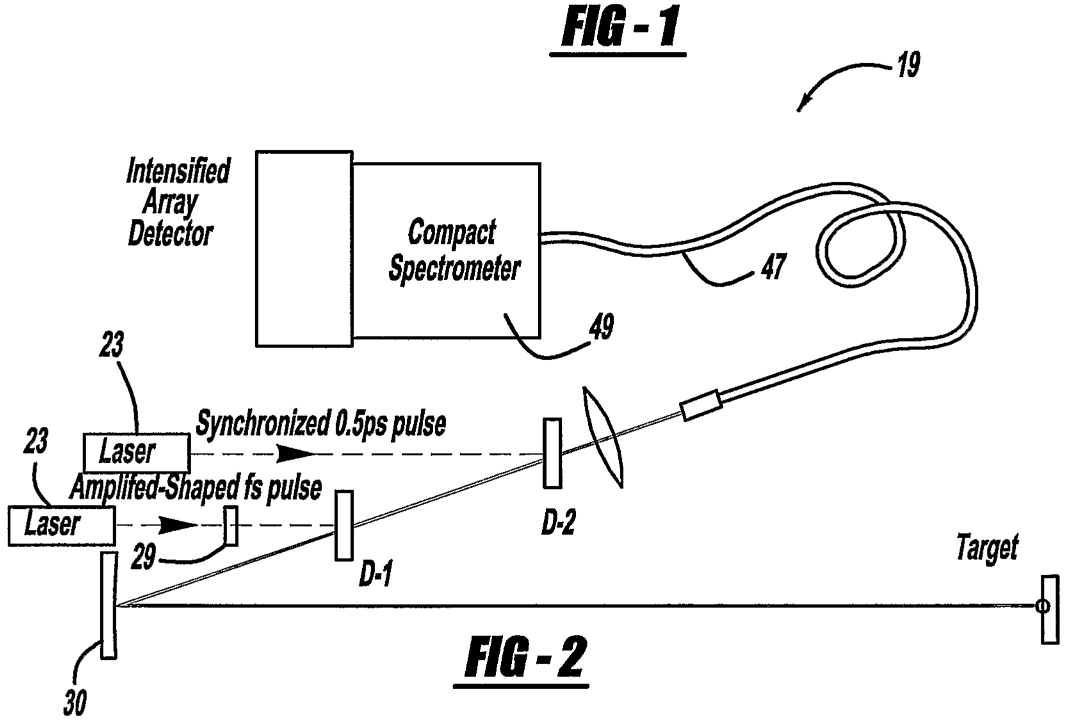
FIG. 2 is a diagrammatic view showing a remote BPS-ISRS setup employed in the preferred embodiment system.
Figure 11:
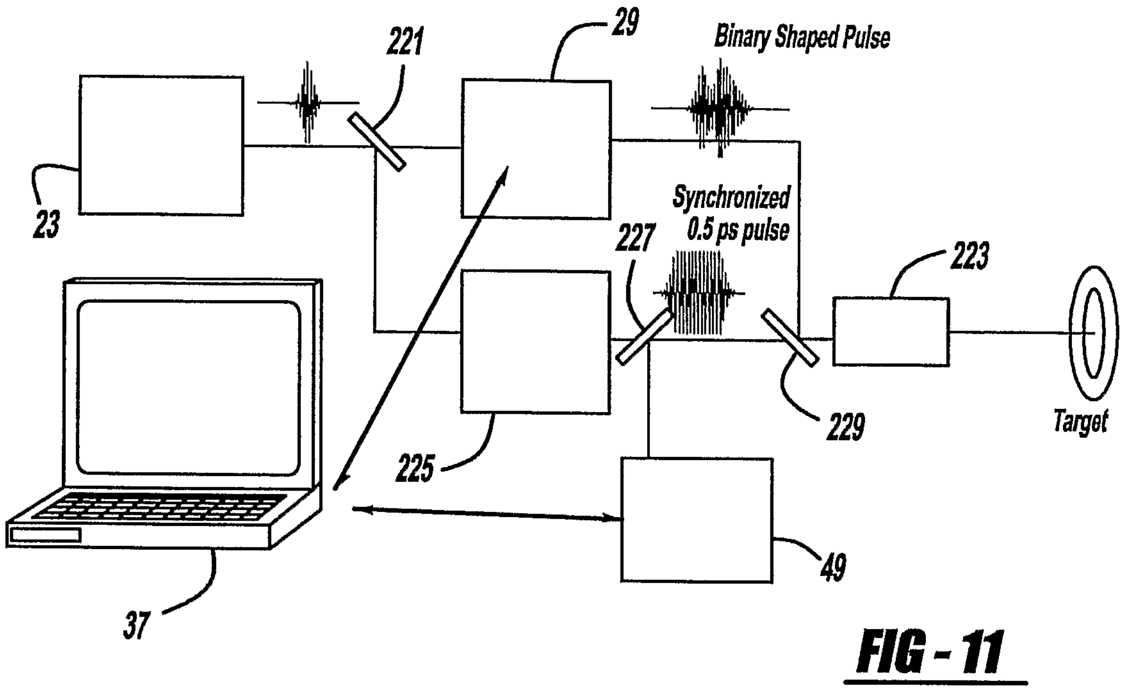
FIGS. 11 and 12 are diagrammatic views showing two variations for the hardware employed with the system of the present invention.
Figure 12:
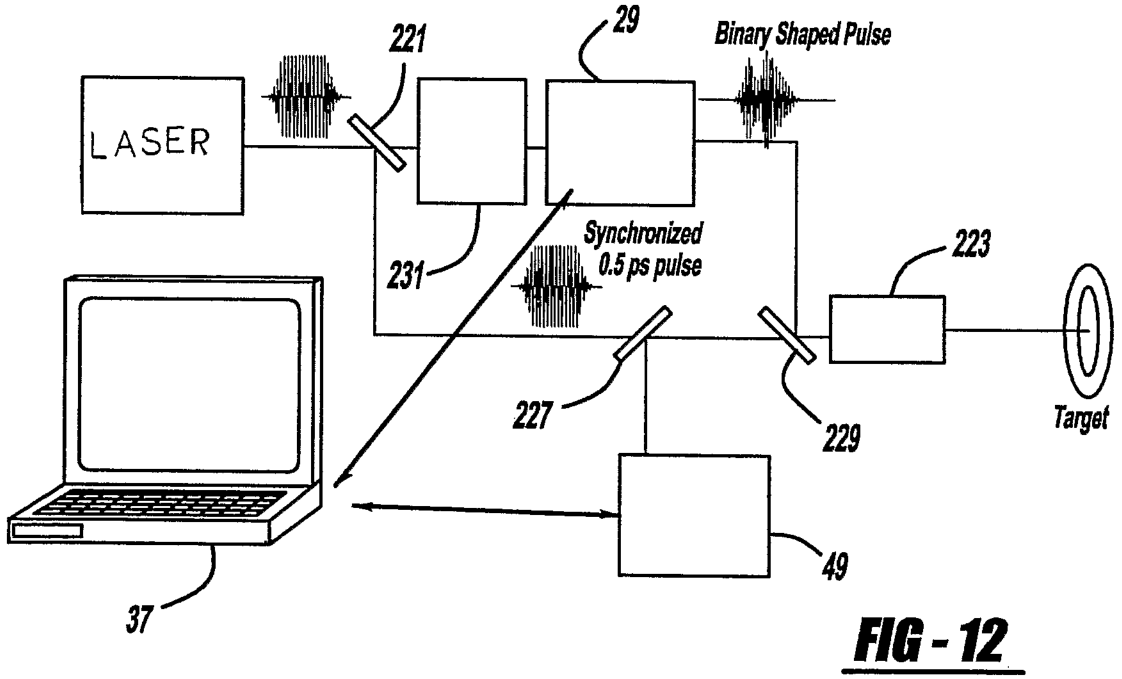

The design and construction of the radiant emission detection system is as follows. For initial testing a system based on a 0.5 m focal length design is shown schematically in FIG. 2. Two laser pulses are used as shown in FIG. 11 or FIG. 12. The laser system 23 is an amplified Ti:Sapphire source which generates sub-45 fs pulses, at a 1 kHz repetition rate, with 0.7 mJ of energy per pulse. The laser is shaped by a 128 pixel phase-amplitude SLM based pulse shaper 29. Furthermore, the pulse shaper is self-calibrating using the MIIPS method. The second laser pulse is derived using a beam splitter 221 and using a portion of the laser pulse to pump a non collinear optical parametric amplifier 225 that will generate the local field from the same laser 23. The wavelength of the local field will be chosen to be near 1064 nm with 0.5 picosecond duration and a narrow bandwidth. Moreover, two dichroic mirrors D-1 and D-2, and a focusing mirror 30 are provided. Mirror D-1 has maximum reflection from 700 to 900 nm, and is AR coated in the back. Mirror D-2 has a very sharp high reflectance window from 1050 to 1075 nm, and is AR coated in the back. Thus, mirror D-1 reflects the femtosecond laser pulse but transmits the reference pulse. Both mirrors transmit the backwards propagating signal and the use of a concave gold coated mirror for both the femtosecond laser and the reference beam provides wavelength independent focusing.

Referring to FIG. 11, an amplified Ti:Sapphire, ultra-fast laser 23 has an output of 1 milli-Joule, but greater than 1 micro-Joule centered at 800 nm. With this embodiment, laser 23 emits 50 femtosecond or less pulses, and more preferably pulses around 20 femtoseconds. A pulse shaper 29 can be like those discussed hereinafter, and a non-collinear, optical parametric amplifier 225 are employed. Amplifier 225 generates a synchronized pulse at a different wavelength than the incoming pulse; for example, to generate a synchronized and narrow bandwidth pulse that is at least 2000 wave numbers detuned from the amplified laser system. A spectrometer detector 49 records a spectrum and is preferably a compact unit with an array detector. A telescope 223 or microscope is used for both excitation and detection paths, or alternately, two telescopes can be used. Furthermore, a beam splitter 221 and dichroic mirrors 227 and 229 are in the optical paths. A CPU computer controller 37 is used to build a database and/or uses a prestored database library for sample identification.

The alternate system of FIG. 12 is similar to that of FIG. 11, but with some differences. In this exemplary embodiment, a Ytterbium based, amplified laser produces 10-500 femtosecond pulses, which is more compact and less expensive. The output is centered near 1050 nm and has an output of at least 1 mJ. A Chromium Forsterite laser can also be used. A bandwidth expander 231 is provided which expands the coherent bandwidth of the laser pulse, in combination with a noncollinear optical parametric amplifier or a micro-structured optical fiber.

Figure 4A:
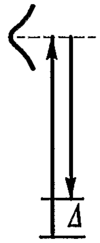
FIGS. 4*a-c* are graphical representations showing the rationale for optimizing ISRS with a shaped pulse used in the preferred embodiment system.

The stimulated Raman scattering step by the femtosecond laser is optimized in the present invention. As illustrated in FIG. 4*a*, impulsive stimulated Raman scattering requires a double interaction with the field and defines the Raman shift Δ following the principle of MII. This is in accordance with the equation:

$$S^{(ISRS)} \propto \int |E^{(1-1)}(\omega)|^2 d\omega$$

Figure 4B:
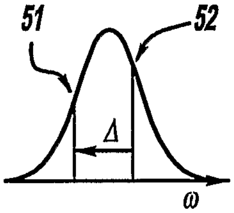
Figure 4C:
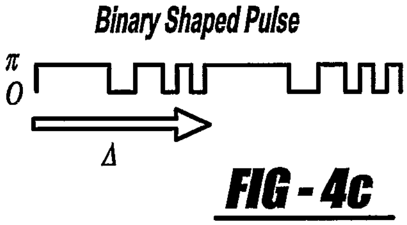

The MII condition is based on the design of two regions in the field that stimulate the two steps involved in the ISRS process. In FIG. 4*b* the expression for the field responsible for ISRS is as follows:

$$E^{(1-1)}(\Delta) \propto \int E(\Omega+\Delta)E*(\Omega)d\Omega$$

$$|E(\Omega)|e^{-i\phi(\Omega)t} \quad (1)$$

$$|E(\Delta+\Omega)|e^{i\phi(\Delta+\Omega)t} \quad (2)$$

where equation (1) is at point 51 and equation (2) is at point 52. Note that there are two components (left and right), and it is the difference between these two that determines the transition. FIG. 4*c* shows how BPS designs a phase that optimizes the condition given in FIG. 4*b*, using the equation:

$$\phi^{(1-1)}(\Delta,\Omega)-\phi(\Omega+\Delta)-\phi(\Omega)$$

The search for optimal ISRS phase functions using genetic algorithms is highly inefficient. Nevertheless, by restricting the shaper to binary phase only and not to amplitude, the best solutions have not been lost. Furthermore, the search space is highly symmetric. It is believed that the best solutions are given by pseudorandom number series, that is, series that have little or no repetition. In particular, Galois series are used to construct phases with up to 128 pixels that optimize very narrow ISRS processes at a desired detuning frequency.

This new method employs spectral phase functions of pseudorandom binary sequences with translation symmetry. A pseudorandom binary number is chosen from a list of sequences with minimal correlation. Such lists can be found in: M. R. Schroeder, *Number Theory in Science and Communication: with applications in cryptography, physics, digital information, computing, and self-similarity* (1997), p. 362; and J. Knauer, http://www.cecm.sfu.ca/jknauer/labs/records.html (Oct. 8, 2004). The symmetrized functions can then be obtained as follows: First, a pseudorandom binary number from a list of sequences with minimal correlation (for N=8, for example, it is 10110000) is selected. Second, the number is symmetrized (or antisymmetrized) depending on the nonlinear process, using reflection for two photon excitation [1011000000001101' and translation for stimulated Raman scattering; 1011000010110000], producing a phase function that will cause the desired selective nonlinear optical excitation excitation.

It is estimated that the target to background ratio selectively gained by pulse shaping is at least one order of magnitude greater for the present approach compared to conventional attempts. The selectivity and tuning range of the present invention are ideal for discriminating between different molecular species. The highly nonlinear interaction between the laser and the sample allows excitation of much higher vibrational levels with much longer pulses. Thus, it is believed that the present invention will achieve selective excitation within the first 500 $cm^{-1}$ and perhaps well beyond that range.

Another advantage of the present invention is the preferred use of IR as the local field to carry the signal instead of UV. First, scattering and spontaneous emission rates increase roughly as the cube of the frequency of the incident light, for a conventional proposal with UV and a third harmonic of the YAG laser for the local field, resulting in almost an order of magnitude greater background compared to infrared probing. Second, the transmission of IR is much greater that that of IR light in the atmosphere, therefore providing a greater range for remote sensing. Another advantage is the confocal excitation/probing arrangement of the present invention setup shown in FIG. 2. Given that the two lasers are in the near infrared, both can be focused with the same gold mirror and the signal can be collected with the same mirror, therefore minimizing losses due to misalignment or chromatic distortions. Detection can be achieved using a fiber optic line 47 coupled to a miniature spectrometer 49, such as an intensified Ocean Optics device.

A computer program interfacing between the pulse shaper and the detector sub-systems is used to achieve BPS-ISRS. The most efficient data acquisition and the number of averages that are required to extract the desired signal to noise ratio are determined. Finally, a protocol that collects spectra from a pre-selected number of binary phase pulse shapes is also determined.

A multidimensional database for remote molecule identification using BPS-ISRS, including pulse shapes and expected signatures, is used for unequivocal and fast sample identification. This database has selective excitation data at particular vibrational modes which translates into enhanced peak intensity in the recorded Raman line. The database also includes excitation data that does not cause enhancement, which is used by the remote controller to automatically discriminate from other compounds that may have similar Raman spectra. With each spectra recorded and used for identification, an exponential increase in the confidence value is gained. For example, if the method of the present invention has a 10% uncertainty, per measured spectra, N-differently stimulated spectra will result in a reduced uncertainty of $(0.1)^N$, provided that each spectra is distinguishably different based on the ISRS process induced by the shaped pulse.

Figure 6:
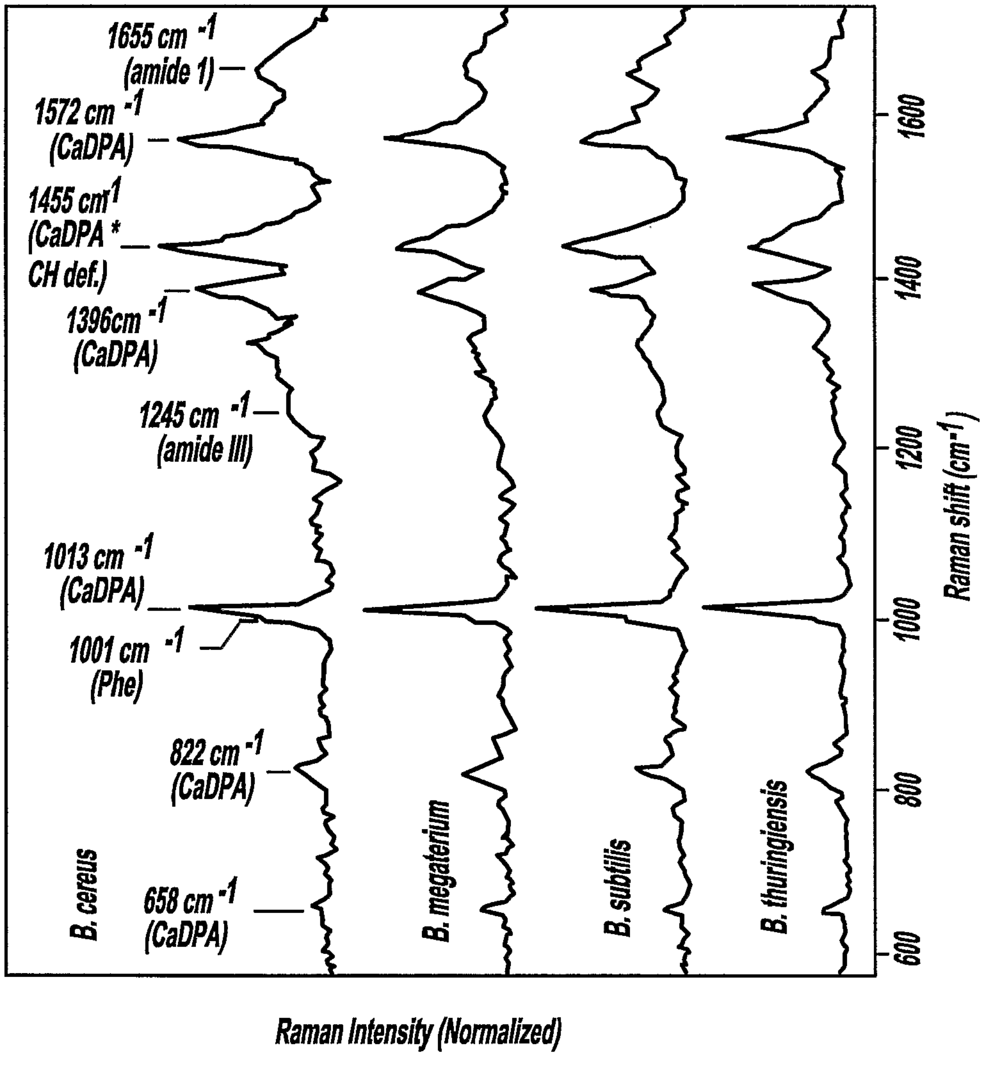
FIG. 6 is a graphical representation of microscopic Raman spectra for four different *Bacillus* spore specimens for analysis by the preferred embodiment system.

Identification of biological agents has traditionally been very difficult because of great similarities between these species. Essentially, all living material is composed of organic compounds with C—H, C—O and C—N bonds. Living materials form domains where a large concentration of a particular type of bond is prevalent, for example membranes have a high concentration of C—H bonds due to the saturated hydrocarbon chains. One of the greatest challenges for biological sample identification is to identify different types of spores, and in particular anthrax spores. *B. anthracis* belongs to the *B. cereus* group of six *Bacillus* species (e.g., anthracis, cereus, thuringiensis, mycoides, pseudomycoides, and weihenstephanensis). Despite such close affinities to *B. anthracis*, no other members of the *B. cereus* group are so deadly to humans. FIG. 6 shows the close similarity in the Raman spectrum of the *Bacilus* spores, which are usually identified by their sharp calcium dipicolinate (CaDPA) band. Due to their similarity positive identification of anthrax spores requires PCR amplification followed by identification of chromosomal markers. The incubation time is typically 18 hours.

A method capable of identifying anthrax within minutes, such as that expected with the present invention, would be ideal and could save lives. It is believed that the method disclosed herein would be able to take advantage of the multi-dimensional selective ISRS excitation afforded by the shaped laser pulse, and the resulting coherent and incoherent emissions to distinguish among the different *Bacillus* spores. The rationale would be that the nonlinear interactions between the shaped pulses and the spores may amplify the differences. To find the differences, the acquisition of spectra for 10,000 differently shaped pulses is used, with each spectrum having the average of 100 laser shots for a total of 20 minutes of data acquisition. A key parameter, such as the height of the CaDPA peak (1013 $cm^{-1}$) divided by the height of the amide III band (1245 $cm^{-1}$), could be identified. A data set for each of the *Bacillus* variants allows comparison. It is important to find the greatest differences and then to reduce the experimental space to 1024 shaped pulses responsible for the greatest orthogonality. The resulting 32×32 space would be a multidimensional analysis that can be acquired in 2 minutes and provide a pattern that can be used to identify the different spores within minutes.

Figure 5:
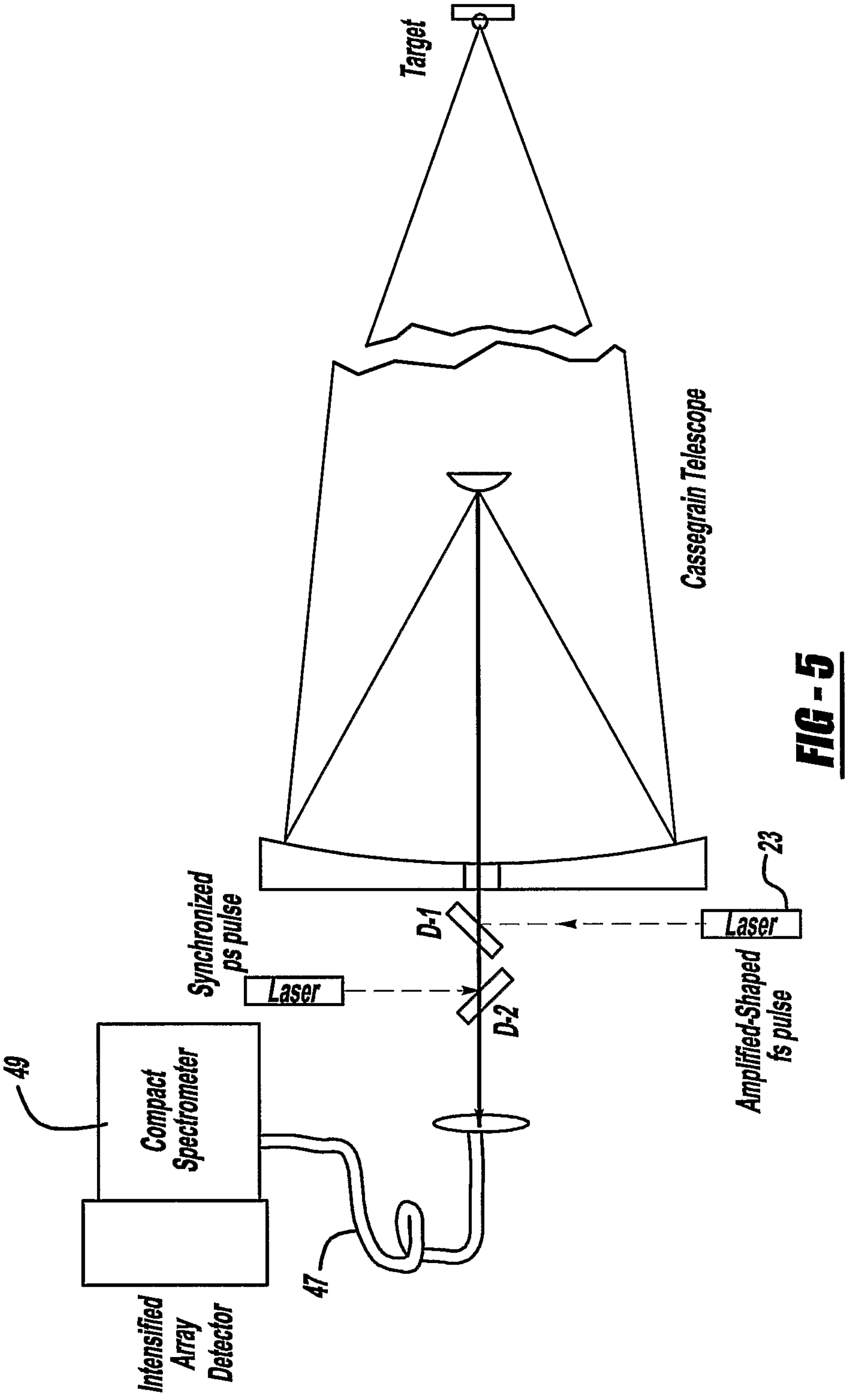
FIG. 5 is a diagrammatic view showing a remote BPS-ISRS detection setup used in the preferred embodiment system.

The system of the present invention lends itself to be used for remote detection. The main modification required is the use of a telescope (for example, a 5-inch Meade ETX-125 Maksutov-Cassegrain telescope having a 127 mm clear aperture and 1.9 m focal length) to expand the two laser beams and have them focus at the specimen target. The same telescope also collects the signal using the confocal arrangement previously disclosed hereinabove. This setup will permit scaling to longer distances, although a system where the signal is acquired by a separate telescope could be alternately employed. The situation where both the shaped pulse and the reference pulse have similar wavelength will further prevent chromatic aberration in the setup and as the lasers and signals propagate through turbulent air. The reference or probe beam can act as a local oscillator and be used for heterodyne detection and amplification of the signal. Alternately, FIGS. 1 and 5 show a similar system but without the use of a confocal telescope; one telescope is in the excitation path and a second one is in a detection path.

Beyond the selective excitation of a single Raman active vibration, it will be possible to excite a number of bands simultaneously. While TL pulses will excite all Raman active vibrations (as well as all multiphoton processes), pulses which excite two or three of the strongest Raman active vibrations for a particular compound are preferred. It is believed that these types of shaped pulses will provide much greater molecular discrimination than pulses that selectively excite a single Raman band. Experimental phase functions are optimized on a computer (at 3 GHz) and then transported to the laboratory or field with success. The close correlation between experiments and theory comes from the accuracy of the MII approach. It is believed that as long as the specimen molecule does not undergo fragmentation, the off-resonance laser-molecule interaction will be most strongly influenced through the more intense Raman active modes. Selective excitation using MII and BPS-ISRS should also work satisfactorily for intermediately strong excitation. Under intense field excitation, the laser-molecule interactions are highly nonlinear and it is possible to excite Raman active modes that are clearly outside the bandwidth of the excitation pulse. The selective excitation depended on the intensity and the phase-amplitude shaping.

Again, one of the advantages of the system and method of the present invention is that it is robust enough to operate in the presence of a complex chemical environment. For example, if the environment being monitored is next to many automotive vehicles or a bus stop, the unit will detect diesel, gasoline and exhaust fumes. Under these conditions, it will be imperative to take advantage of the multidimensional properties of the present invention. TL pulses will yield mass spectra with a number of suspect ion masses. However, upon further analysis, the system will determine that no unacceptable, dangerous chemicals are present. If these conditions persist, the remote computer will automatically define a background level of contaminants and actively subtract it. The power of multidimensional analysis is extremely valuable if a mixture of chemical agents is present. The present invention system would have no problems determining which chemicals are present even under these adverse conditions. Finally, if a new chemical threat is developed by a terrorist group, the command center can update all the systems in the field with a new library that contains the spectrometric signature that is obtained by multidimensional laser interrogation of that compound. The addition to the library would take less than a day to generate in the laboratory, and would be available for immediate use by the monitoring systems upon upload.

One laser and detector system creates the library. That unit is in a laboratory and is capable of handling nasty chemicals. The other field system is compact and automated and uses the libraries prepared by the first system. The second system can be compact and is field transportable. Both systems have fs laser, shaper, miips, binary shaping, computer controller. The only difference is that one is used to generate the library in a laboratory setting. The other one is fully automated and field deployable. The field system is made to be a closed box that requires minimum maintenance.

Pulse Shaping System

Figure 7:
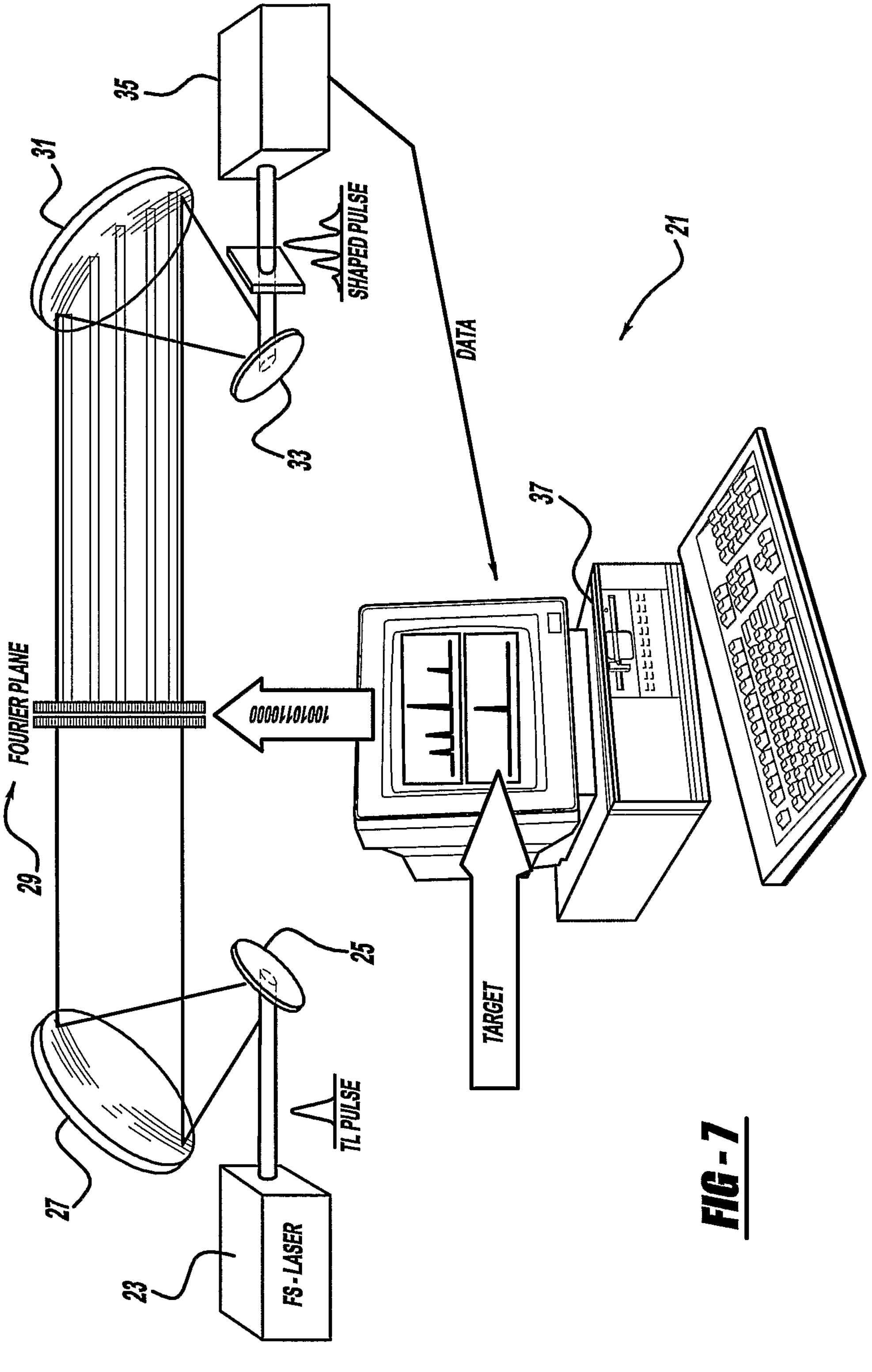
FIG. 7 is a diagrammatic view showing the preferred embodiment system setup for initial identification operation.

The preferred embodiment hardware of an apparatus 21 for use with the laser system is generally shown in FIG. 7. This hardware setup is ideally suited for use in an initial laboratory situation to first correlate the desired pulse shapes to best differentiate and identify target molecules in a specimen. Apparatus 21 includes a femtosecond laser 23, an upstream grating 25, an upstream convex mirror 27, a spatial light modulator 29, a downstream concave mirror 31, a downstream grating 33, a detection device 35, and a personal computer 37. The pulse shaper is the entire optical setup from grating to grating. As will be discussed later, the gratings can be replaced by a prism, and the spatial light modulator can be a deformable mirror, a liquid crystal spatial light modulator or a microelectronic micromechanical system MEMS. The pulse shaper can also be reflective instead of transmissive. Finally, the pulse shaper can also be an accousto optic shaper.

Personal computer 37 has a microprocessor based electrical control system, memory, an output screen, a data storage device, an input keyboard, and a storage disk. More specifically, the detection device is a mass spectrometer. Alternatively, the detection device is a compact spectrometer with an array detector. Bursts or pulses of a laser beam are emitted from laser 23, through the optics 25, 27, 31 and 33, as well as through the spatial light modulator 29 for detection and sensing by the spectrometer detector device 35 for further evaluation, analysis, comparison and subsequent control by personal computer 37.

The laser is preferably an ultra-fast femtosecond laser capable of high peak intensity (with a typical peak greater than $10^{14}$ watts/$cm^2$) which preferably emits laser beam pulses of less than 100 femtosecond duration, and more preferably at or less than 25 femtoseconds, and for the environmental monitoring and/or Raman active vibrational excitation applications even more preferably as short as 10 femtosecond duration, for each pulse burst or shot. The intense optical pulses are formed in a Kerr-Lens mode locked titanium sapphire oscillator. Such lasers are capable of producing hundreds of nanometers of coherent bandwidth, although only about 50 nm are typically used. The output is amplified in a 1 kHz regenerative chirped pulsed amplifier. The output pulse is typically 100 fs long with a central wavelength of 800 nm and total pulse energy of 0.1 to 1 mJ. Preferred lasers include: the Kapteyn and Murnane femtosecond laser oscillator, which can produce less than 15 fs pulses at 100 MHz; and the Hurricane model from Spectra Physics Inc., which is diode pumped and gives 0.8 mJ per pulse with sub-50 fs pulses at 1 kHz. More compact and less expensive lasers provide another excellent alternative. Among these are the CPA-2001+ model from Clark-MXR Inc., which gives 1.3 mJ per pulse with sub-150 fs pulses at 1 kHz, and the diode-pumped Ytterbium laser producing intense 300 fs pulses at 1 kHz. These less expensive and more compact units produce pulses that have narrow bandwidths, therefore it is important to use the alternative setup depicted in FIG. 12 that pumps a Clark-MXR Inc. non-collinear parametric amplifier (hereinafter "NOPA") which produces 0.2 mJ per pulse, and is capable of generating sub-20 fs pulses. A time of flight mass spectrometer (TOF-MS), or a compact Ocean Optics spectrometer, are preferred for detection purposes.

A Fourier plane pulse shaper is preferably used with the present invention for the transmissive construction illustrated with this embodiment. Ultra-short laser pulses contain from one to fifty optical cycles, and last only a few femtoseconds. This is much faster than most current electronics and therefore shaping with fast time gates is very difficult. On the other hand, because of the uncertainty principle, the optical spectrum spans tens to hundreds of nanometers. Such a large bandwidth is relatively easy to measure and to filter, and there are several techniques to shape the spectrum in the frequency domain, and thereby shape the temporal pulse upon recompression.

In order to access the frequency domain and the individual frequency components that comprise the pulse, a geometric arrangement is employed, using two back-to-back spectrometers. The spectrometers are especially designed to introduce no net temporal dispersion: that is, all colors pass through the spectrometers within the same amount of time. The first spectrometer (including grating 25 and mirror 27) spreads the unshaped pulse spectrum along a line according to its dispersion function y(α). The light intercepts spatial amplitude and phase mask spatial light modulator 29 at this point. The mask output then forms the entrance to a second spectrometer (including grating 33 and mirror 31) which recombines the colors into a single shaped pulse.

The heart of the pulse shaper is the programmable 256 pixel liquid-crystal mask (consisting of two overlapping 128 pixel liquid crystal arrays) that is placed at the Fourier plane 29. For the applications envisioned herein, the mask must be capable of shifting the phase of individual frequencies. For alternate embodiment pulse shapers, a different electronically programmable mask that is capable of controlling phase has been demonstrated: a liquid crystal display (hereinafter "LCD"), an acousto-optic modulator (hereinafter "AOM"), a deformable mirror, and a permanently deformed mirror. A LCD pulse shaper can be obtained from CRI Co. and has a modulator electronic driver.

The AOM consists of an anti-reflection coated Tellurium Dioxide ($TeO_2$) crystal with a piezo electric transducer glued onto one end. The central frequency of the acoustic wave is αc/2π=200 MHz. The acoustic velocity vs in the crystal is 4.2 km/s and the light pulse spends less than 10 ps in the crystal, so the acoustic wave moves less than 0.002λ acoustic during the transit of the light field through the crystal. Since the acoustic wave is essentially frozen as the optical pulse travels through the crystal, the complex amplitude of the acoustic wave traveling through the crystal in the y direction, A(t) cos αct=A(y/vs) cos αct, is mapped onto the optical field E(α) as it passes through the AOM. If some of the dispersed optical field encounters a weak acoustic wave, that frequency is attenuated; if the acoustic wave carrier is shifted by phase angle ø, that phase shift is imposed on the optical field. This pulse shaper has a total efficiency of about 20% including the diffraction efficiency of the AOM and the diffraction efficiency of the gratings. The diffracted light is used and the undiffracted "zero order" beam is blocked, to allow full modulation of both amplitude and phase in the shaped beam. The shaped beam then has the form $$E_{shaped}(\omega)=E_{input}(\omega)x\alpha(\omega)xe^{i\phi(\omega)t}$$

where $\alpha(\omega)e^{i\phi(\omega)}=A[y(\omega)/v_s]$; α is the frequency, and e is a constant.

Fixed pulse shaping optics, such as chirped mirrors or permanently etched reflective masks, can also be employed. The laser pulses are fed into the pulse shaper where the grating 25 causes dispersion. Curved mirror 27 focuses the spectrum onto Fourier plane 29. Changes in the phase ø of the spectral components indicated by the computer are used to tailor the laser pulse before reconstruction with second curved mirror 31 and grating 33. Once shaped, a small portion of the pulse is directed to spectrometer 39 for evaluation and calibration using MIIPS. The greater percentage of the laser, for example 95%, is sent towards the mass spectrometer for monitoring purposes.

In this embodiment, the phase and amplitude masks of the pulse shaper are controlled by the computer wherein the laser pulse shape takes a dynamic role. The microprocessor within personal computer 37 will then control laser 23, receive an essentially real time feedback input signal from the spectrometer, and then perform calculations, comparisons and evaluations, and possibly automatic variation of subsequent pulse shapes. These automated steps can be substituted with manual user calculations and decisions if desired based on personal computer outputs.

As applied to the environmental monitoring applications herein, selective control of multiphoton processes in large molecules, including proteins, is possible using a simple pulse shaping method that is based on taking maximum advantage of the multiphoton intrapulse interference caused in short pulses with large bandwidths, and the resulting fluctuations in the electromagnetic pulse. An extraordinary level of control can be achieved that is robust and sample independent, with contrast ratios near two orders of magnitude. Such large contrast ratios allow for more precise cancellation control of undesired photons and other laser beam characteristics, such that nonlinear transitions induced by each pulse are controlled. Moreover, a fs-pulse shaper arrangement can be used to achieve selective fragmentation of the sample molecules, and this property can be exploited for identification. The details of the underlying technology will be described in greater detail hereinafter. Alternately, instead of an LCD-SLM to introduce phase functions prestored in the memory unit of the controller, phase functions can be incorporated into a passive optical component such as a turret with different static phase masks manufactured on a transparent substrate. The turret can toggle the static phase masks in front of the mirror. A system with such a turret would reduce the complexity and expense of computer controlled LCD-SLM. Nevertheless, the ability to run a MIIPS test is valuable to make sure that the laser is operating properly, thus, a computer controller pulse shaper will be preferred for this application.

Multiphoton Intrapulse Interference

A multiphoton intrapulse interference phase scan (hereinafter "MIIPS") system and method are preferably employed with the present invention system to characterize the spectral phase of the femtosecond laser pulses. The phase across the spectrum of an ultrafast pulse can affect the multiphoton process in a number of ways. Phase can increase the pulse length and hence reduce the peak intensity of the pulse, thereby preventing saturation, a common result under high intensity excitation. Phase can also be used to synchronize changes in the electric field with intramolecular wave packet dynamics. Finally, phase can be used to cause interference in the way multiple frequencies combine to achieve multiphoton excitation. This process is known as multiphoton intrapulse interference (hereinafter "MII").

The technique of MII and its application to control multiphoton processes is based on rationally designing an electric field required to achieve a particular target with a minimum number of parameters. The method is based on calculating the amplitude of the nth-order electric field and comparing it to the absorption spectrum of the molecules being controlled. This provides a strong physical understanding of the control process, which can be very useful in the interpretation of experiments where the field is optimized by computer programs based on evolutionary learning or similar methods. For strong field photofragmentation and ionization, required for environmental monitoring, less is known about the pulse shapes to be used. The preferred method will be to address the molecules through their Raman active vibrations taking advantage of selective ISRS. Determination of the optimum pulse shapes to identify each molecule will be obtained experimentally using a wisdom based learning method that will combine known molecular parameters, and maps of the resulting spectra as a function of the binary shaped functions.

Multiphoton intrapulse interference phase scan is capable of both pulse characterization and compensation of subsequent pulses. Within minutes, the pulses are characterized and compensated to yield transform-limited (hereinafter "TL") or user-specified shaped pulses at the sample. This capability is important for the reproducibility of the present invention. This will ensure that the pulse shaper and laser are operating within specifications.

MIIPS is a single-beam method that does not require an interferometer. To make a precise and accurate measurement of the spectral phase using MIIPS, a known phase delay is imposed on the frequencies that make up the pulse using a calibrated pulse shaper. The pulse shaper essentially behaves as two back-to-back spectrometers. In one variation, the pulse emitted by the laser is dispersed with a grating and collimated with a 200-mm cylindrical lens. At the Fourier plane, where all the frequencies are isolated, their phases are manipulated by a computer-controlled. LCD spatial light modulator (hereinafter "SLM"). The SLM applies the reference phase function to the input pulse. The resulting pulse is then retro reflected and reconstituted to the time domain and the output is picked by the mirror. The SLM can be updated every pulse (presently limited to 1 kHz). The LCD has a 250-ms response time, so in principle it can be updated at 4 kHz. A small percent of the output beam is reflected by a partially reflective mirror and is analyzed by focusing (with a lens) onto a 0.10-mm-thick beta barium borate crystal for second-harmonic generation (hereinafter "SHG") in its path, usually at the place where optimum pulses are required. The use of the second harmonic is important to the method. The average SHG output is collimated by the second lens and directed to a dispersive spectrometer and detected by a detector array. For each reference phase function that is introduced by the computer-controlled SLM, a different spectrum is recorded and stored in the computer controller. In a sense, the pulse autocorrelates itself at the SHG crystal.

Pulse characterization involves the introduction of a reference phase-modulation function of the form $\Phi = \alpha \cos(\gamma\Omega - \delta)$, where $\alpha$ is the magnitude of the phase delay, $\gamma$ is the periodicity $\Omega$ is the frequency detuning from the carrier frequency of the pulse, and $\delta$ is the position in the spectrum at which the cosine function is equal to one. The reference phase function, with typical values $\alpha = 2\pi$, and $\gamma$ =pulse duration, is programmed into the SLM and scanned for different values of $\delta$ ranging from 0 to 2 $\pi$. For each value of $\delta$, the spectrum of the frequency-doubled pulse changes, achieving a maximum in the spectral region over which the SLM compensates for the phase distortions.

Qualitatively, the distance between the diagonal features determines linear chirp while the angle between the features determines the quadratic chirp. The full quantitative determination of the spectral phase by integration can be obtained. Once the MIIPS system has characterized the pulse and retrieved the phase distortions inherent to the pulses, it can use that information to drive the SLM such that it compensates for the distortions. The first step in compensation is to take the phase determined from the first scan and program it into the SLM with a negative sign so that it subtracts the distortions. The system carries out a new phase scan to determine the remaining spectral phase modulation (usually about 10% of the original). Typically, three such iterations will yield transform-limited pulses. Because the laser is not focused in the pulse shaper, the method can be used with pulses that are relatively high in energy. Pulses ranging from about 10 pJ to about 30 mJ and pulse durations from less than 5 to about 500 fs can be used. Once the pulses are compensated (transform-limited), the laser can be focused to produce peak intensities from about $10^{12}$ to about $10^{18}$ W/cm$^2$, depending on the input energy.

This single beam method is capable of retrieving the magnitude and sign of second and third order phase modulation (in other words, linear and quadratic chirp) directly, without iteration or inversion procedures. MIIPS achieves accurate phase retrieval from chirped ultrashort pulses. For MIIPS, no synchronous autocorrelation, beam splitting, or time delays are required because the second harmonic spectrum depends on the relative phases of all frequencies within the pulse. The amplitude of the pulse is obtained directly from a spectrometer in a communications receiver. In order to precisely determine of the phase of all frequency components in a pulse from a femtosecond laser, a pulse shaper, such as the one described in A. M. Weiner, "Femtosecond pulse shaping using spatial light modulators," Rev. Sci. Instrum. 71, pp. 1929-1960 (2000), is employed to introduce a reference phase function designed to yield this information directly, as further described hereinafter. The shaped pulses are frequency doubled by a thin SHG crystal and the output is directed to the spectrometer.

The MIIPS method is based on the principle that second harmonic generation, as well as other nonlinear optical processes, depend on the phase function $\phi(\omega)$ across the spectrum of the laser pulse. Higher order phase distortions, such as self-phase modulation and quadratic phase components can be obtained from the curvature of the line defined by the maximum SHG response. The MIIPS can be programmed to find the phase distortions on the laser pulses directly by integration and to introduce a compensation phase function that eliminates the distortions. This mode of operation can be used to find arbitrary phase deformations and yield transform limited pulses, which in a MIIPS scan, look like straight parallel lines separated by $\pi$.

The present invention provides a system and method to characterize and compensate for the spectral phase distortion of femtosecond pulses. This single beam method is capable of retrieving the magnitude and sign of linear and quadratic chirp with high resolution. Pulse retrieval is based on analytical expressions that yield the phase distortion, without iteration or inversion procedures. Linear and quadratic chirp values, and to some extent cubic chirp values, are important because there are knobs on the laser that can be used to correct for this distortion by mechanically adjusting the grating spacing in the laser beam amplifier compressor. The method can be used with very short pulses. This adjustment can be automatically controlled with the computer controlled software. The method is very versatile, and can be used with high or very low intensity pulses for any wavelength for which low cost, off-the-shelf SHG crystals exist. MIIPS can also be used by obtaining third or higher order harmonics in gases. The maximum signal makes the method useful for the characterization of pulses in wavelength regions for which SHG crystals are not available.

Binary Phase Shaping

Laser control is dominated by interference between different nonlinear optical pathways connecting the initial and final states. The challenge is finding the proper phase for each frequency within the pulse to achieve constructive interference at the desired pathway and destructive interference elsewhere. To a very good approximation, it is sufficient to set the phase of different frequency components of femtosecond pulse to two values separated by $\pi$. To obtain a very good approximation, it is sufficient to set the phase of different frequency components of a femtosecond pulse to two values separated by $\pi$. The phase between photons of different frequencies takes only two values, preferably 0 or $\pi$, to maximize or minimize a given pathway. Any two values whose difference is $\pi$ work equivalently well. This method is defined as binary phase shaping. BPS is preferably used to solve the problem of selective multiphoton excitation with ultrashort laser pulses. The use of a small number of phase values between 3 and 10 is regarded as a trivial extension of our binary approach.

In order to control the behavior of molecules under the intense radiation of a femtosecond laser, it is important to modulate the phase of the frequencies within the bandwidth of the pulse. For the invention being described, this implies, finding the best binary value for each of the spectral components that traverses a discrete region in the shaper corresponding to a pixel. In some shapers, the pixel may be discrete as in a liquid crystal, or a moving MEMS component. In other cases the pixel may be continuous as a region in an AO crystal or a deformable mirror. The appropriate phases that generate a specific desired outcome that is useful in the identification of a chemical, is found using an evolutionary learning calculation and program.

In another variation of the present invention, specific phase functions designed to produce a specific time-domain fluctuation of the electric field in the time domain will be programmed in the analyzer, and the behavior of all chemical agents of interest evaluated for their behavior when interrogated by these specific phase functions. These functions could be introduced as fixed optics produced by etching or other micromachining methods, or programmed on 128-pixel SLM or a SLM with greater than 256 pixels.

A titanium-sapphire regeneratively amplified laser is preferably employed, which can be obtained from Coherent Lasers, and it is capable of generating pulses as short as 30 fs. Alternately, multipass amplification may be used. The spectral phase of the pulse is tailored using a computer-controlled pulse shaper. Preferably, the pulses are centered near 800 nm. A Ytterbium laser, centered at 1040 nm, may alternately be used. The spectral phase of each pulse is corrected using the MII phase-scan (MIIPS) method, which compensates phase distortions to obtain transform-limited (TL) pulses. The binary phase is introduced as an addition to the compensation phase. About 1% of the shaped laser pulse intensity, with energy ~0.003 mJ per pulse and 1 kHz repetition rate, is focused, to a spot size of ~20 microns in diameter, on a 100 micron thin beta barium borate (βBBO) type I SHG crystal. The frequency-doubled light is collected with an optical fiber and dispersed on a compact spectrometer, preferably obtainable from Ocean Optics. This setup is used at regular intervals to ascertain that the laser system and pulse shaper are operating properly. Most of the intensity of the laser beam with energy ~0.3 mJ is directed towards the target where it interacts with the sampled air, causing photofragmentation and ionization.

The advantage of BPS is that computational redundancies are greatly reduced. For BPS and 128 active pixels, the search space is reduced by hundreds of orders of magnitude compared to arbitrary phase and amplitude pulse shaping as discussed above. The resulting space is small enough that a greater percentage of the search space can be evaluated experimentally. A learning feedback method or simple evolutionary learning computer program can quickly converge towards significantly improved solutions. BPS has significant technological advantages. A retardation equivalent to π is easy and fast to obtain and calibrate. Permanently etched masks can be made in advance and used for specific applications.

Library Evolutionary Learning Computer Program

Initially, the pulse shaper is programmed for monitoring the environment based on requirements of a library of data stored in memory of the computer. Fast, accurate and reproducible monitoring of the environment for chemical and biological agents, will not usually permit the pulse shaper to run in an evolutionary learning mode in the field, although such field use still falls within the scope of the present invention. Instead, a much more efficient mode of operation is used, whereby the unit is continuously monitoring the environment with transform-limited pulses. Under these circumstances, the unit takes a fraction of a second to make preliminary, but highly sensitive measurements. In the event that a suspected molecular ion fragment is detected, then the unit activates a library search for the pre-stored suspected agents and employs a series of pre-programmed shaped pulses to make an absolute identification. While in the search mode, the unit can speed by three to six orders of magnitude in repetition rate to provide the fastest analysis possible. Because it is using a pre-programmed series of shaped pulses, the whole identification process can be completed in under a minute.

The wisdom based evolutionary learning program is used in a laboratory setting to define a library of pulses and begins by evaluation of a set of 512 binary phases that are chosen to represent all functions that are possible with 10 groups of pixels. Each pulse shape is tested for its fitness (ability to generate the result that most resembles a target selected in advance). The map of fitness as a function of binary phase function reveals important information regarding symmetry and complexity of the search space. New sets of pulse parameters are created by enhancing the resolution near the regions found to have the best fitness parameters. Finally, in some cases the best phases can be modified through (mutating) and recombining (via crossover) elements of the best of the previous pulse shapes to create new ones (survival of the fittest). This basic series of processes is iterated and the fitness converges toward a "best" value.

In simple terms, the role of the pulse shaper is to advance or retard individual frequencies within a laser pulse by a factor of π. For example, in a TL pulse, all the frequencies are locked, and have net zero retardation. In this case, the spectral phase is flat. The pulse shaper can be used on a TL pulse to make some frequencies arrive before others. In these general terms, a pulse shaper can be defined by a number of parameters: input bandwidth, frequency resolution, and maximum retardance. The spectral resolution of a pulse-shaper setup is determined at the Fourier plane, where the pulse is resolved in the frequency domain. The phase retardation must be calibrated and checked for accuracy and reproducibility. This step will be done by MIIPS as described earlier.

Once the shaping unit is calibrated, it is imperative that the pulse shaper compensates the phase deformations in the femtosecond laser system. Even under ideal conditions, a commercial femtosecond laser produces pulses with phase deformations that are primarily quadratic or cubic in the frequency domain. Multiphoton Intrapulse interference phase scan automatically determines the spectral phase deformations and compensates for them. Within a minute, the phase distortions are eliminated and TL pulses are obtained. The MIIPS method is believed to be at least one order of magnitude more accurate than alternative methods commercially available. The shaper calibration described above, together with accurate phase characterization and compensation provided by MIIPS, are important steps that are believed to ensure the robustness and reproducibility sought by the system of the present invention.

The present invention system depends on the identification of certain shaped laser fields that will produce different uniquely identifiable fingerprints from each chemical or biological compound. The search for these shaped laser fields requires the search of a large parameter space using the evolutionary learning program. BPS reduces the search space and drastically increases the reproducibility. Each chemical will be interrogated by the focused shaped laser field. The spectrum resulting from the nonlinear laser-molecule interaction will be recorded and compared to others. The wisdom-based evolutionary learning program will have a search target and will determine the shape that best approaches the target. The ability of strong shaped laser fields to influence the nonlinear laser-molecule interaction is utilized in order to find uniquely identifying pulses shapes for each molecule. Because laser-molecule control depends on the electronic and nuclear structure of the molecule, no two compounds would yield the same results.

The adaptive laser source may be part of a learning feedback method that modifies the laser pulse shape based on its success at optimizing the yield of charged agents, which may include chemicals or proteins. In the present application, the laser pulse shape takes a dynamic role. The physical process runs itself by an intelligent "feedback" method by means of an intelligent loop. The learning method tries various pulse shapes, assesses their success in achieving the desired target excitation, and uses the knowledge gained in this way to improve the pulse shapes on subsequent laser shots, all with only minimal intervention of the researcher or system user. Changing conditions are automatically corrected within the learning method or feedback loop. The details of the software used in the evolutionary learning program are discussed in U.S. patent application Ser. No. 10/884,798 entitled "Laser System Using Ultra-Short Laser Pulses" filed on Jul. 2, 2004, which is incorporated by reference herein.

Photodynamic Therapy

Figure 9:
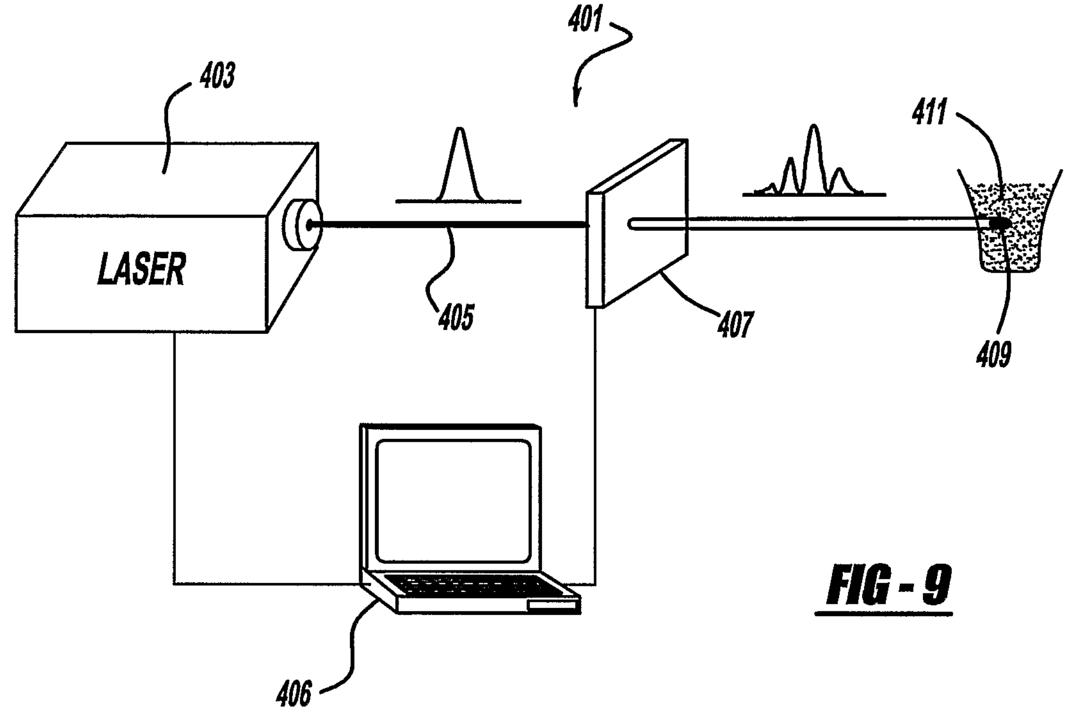
FIG. 9 is a diagrammatic, perspective view showing a second alternate embodiment of the present invention system applied to photo dynamic therapy.

Another embodiment of the present invention uses a system shown as 401 in FIG. 9 for laser excitation or ionization with photodynamic therapy (hereinafter "PDT"), including selective Raman active vibrational excitation of target molecules. PDT is a treatment that involves the combination of visible light and a photosensitizer. Each factor is harmless by itself, but when combined with oxygen, can produce lethal cytotoxic agents that can inactivate tumor cells. This enables greater selectivity towards diseased tissue as only those cells that are simultaneously exposed to the photosensitizer, light and oxygen are exposed to the cytotoxic effect. The dual selectivity of PDT is produced by both a preferential uptake of the photosensitizer by the diseased tissue and the ability to confine activation of the photosensitizer to this diseased tissue by restricting the illumination to that specific region. Therefore, PDT allows for the selective destruction of tumors while leaving normal tissue intact.

PDT is based on the concept that (1) certain photosensitizers can be localized (somewhat preferentially) in neoplastic tissue, and (2) subsequently, these photosensitizers can be activated with the appropriate wavelength (energy) of light to generate active molecular species, such as free radicals and singlet oxygen ($^1O_2$) that are toxic to cells and tissues. PDT is a binary therapy, and a potential advantage of PDT is its inherent dual selectivity. First, selectivity is achieved by an increased concentration of the photosensitizer in target tissue, and second, the irradiation can be limited to a specified volume. Provided that the photosensitizer is nontoxic, only the irradiated areas will be affected, even if the photosensitizer does bind to normal tissues. Selectivity can be further enhanced by binding photosensitizers to molecular delivery systems that have high affinity for target tissue. Traditionally, the wavelength of light is matched to the electronic absorption spectrum of the photosensitizer so that photons are absorbed by the photosensitizer and the desired photochemistry can occur. This poses a number of problems because the laser causes activation outside the focal region. This limitation can be overcome by nonlinear excitation. Except in special situations, where the lesions being treated are very superficial, the range of activating light is typically between 600 and 900 nm. This is because endogenous molecules, in particular hemoglobin, strongly absorb light below 600 nm and therefore capture most of the incoming photons. The net effect would be the impairment of penetration of the activating light through the tissue. The reason for the 900 nm upper limit is that energetics beyond this wavelength are insufficient to produce $^1O_2$, the activated state of oxygen, perhaps critical for successful PDT.

Upon illumination, the photosensitizer is excited from the ground state ($S_0$) to the first excited single state ($S_1$), followed by conversion to the triplet state ($T_1$) via intersystem crossing. The longer lifetime of the triplet state enables the interaction of the excited photosensitizer with the surrounding molecules, and it is generally accepted that the generation of the cytotoxic species produced during PDT occurs whilst in this state.

The excited triplet state can react in two ways, defined as Type I and Type II mechanisms. A Type I mechanism involves hydrogen-atom abstraction or electron-transfer reactions between the excited state of the sensitizer and a substrate that is either biological, a solvent or another sensitizer, to yield free radicals and radical ions. These free radical species are generally highly reactive and can readily interact with molecular oxygen to either generate reactive oxygen species such as superoxide anions or hydroxyl radicals or can cause irreparable biological damage. These reactions produce oxidative damage that is eventually expressed as biological lesions. By contrast, a Type II mechanism results from an energy transfer between the excited triplet state of the sensitizer and the ground-state molecular oxygen, generating the first excited state of oxygen, singlet oxygen. This zwitterionic species is extremely reactive and can interact with a large number of biological substrates, inducing oxidative damage and ultimately cell death. While it is generally accepted that Type II processes predominate during PDT and that singlet oxygen is the primary cytotoxic agent responsible for the biological effects displayed, Type I reactions become more important at low oxygen concentrations or in more polar environments. However, the initial reaction is of lesser importance as both Type I and Type II reactions lead to similar oxidative damage and comparable free radical chain-reactions in the presence of oxygen. The overall effect of either a Type I or Type II reaction pathway is the production of oxidative damage within the target cell that will ultimately lead to tumor destruction. Under special circumstances (short pulse, high intensities of irradiation), the upper excited states may be populated, and complex photophysical and photochemical processes may originate from these states, resulting in increased or decreased phototoxicity, which may include oxygen-independent mechanisms such as DNA mutation.

Photosensitizers are compounds that are capable of absorbing light of a specific wavelength and transforming it into useful energy. In the case of PDT, this would involve the production of lethal cytotoxic agents. There are hundreds of natural and synthetic dyes that can function as photosensitizers for PDT, ranging from plant abstracts to complex synthetic macrocycles. The key characteristic of any photosensitizer is its ability to preferentially accumulate in diseased tissue and to then generate cytotoxic agents to induce the desired biological effect. Examples of such photosensitizers can be found in: W. M. Sharman, et al., "Photodynamic therapy: basic principles and clinical applications," Drug Discovery Today 4(11):508-517 (1999); T. Hasan, et al., "Photodynamic Therapy Of Cancer," Chapter 40 in Holland Frei Cancer Medicine, BC Dekker Inc. (2003); W. M. Sharman, et al., "Targeted photodynamic therapy via receptor mediated delivery systems," Adv. Drug Delivery Rev. 56(1):53-76 (January 2004); and Roy I., et al., "Ceramic-based nanoparticles entrapping water-soluble photosensitizing drugs: A novel drug carrier system for photodynamic therapy." J. Am. Chem. Soc. 125:7860-7865 (2003).

The hardware of system 401 employs a femtosecond laser 403 which emits multiple laser beam pulses 405, a computer 406 and a binary pulse shaper 407 which allows two-photon excitations but essentially prevents three-photon excitation. Laser 403 emits a laser beam pulse shorter than 1 picosecond. Shaper 407 is made of two dispersive elements which sandwich a phase mask element. Excitation of the PDT therapy agent takes place through two-photon excitation. The nonlinear excitation process prevents the laser from damaging tissue outside the focal region. Two-photon transitions are optimally controlled using MII and binary phase shaped pulses as described earlier. The shaped pulses from the pulse shaper 407 enhance the laser-induced activity of a therapeutic agent at a cancerous area 409 but which prevents damage of healthy tissue 411. Use of laser beam pulse shaping of the present invention should provide superior control and results for PDT applications as compared to those practically possible with conventional methods as disclosed, for example, in U.S. Pat. No. 6,042,603 entitled "Method for Improved Selectivity in Photo-Activation of Molecular Agents" which issued to Fisher et al. on Mar. 28, 2000, which is incorporated by reference herein. Alternately, the pulse shaper can be tuned to target cancerous cells for multiphoton gene therapy or destruction, with or without the presence of a therapeutic agent, without damaging healthy tissue. The MII, BPS and ISRS processes, that are possible on femtosecond systems that are compensated by MIIPS discussed hereinafter can be advantageously used to activate only certain pharmaceuticals or chemicals, or used to allow the laser pulse to enter human or animal tissue to a known depth, based on the phase tuning and associated nonlinear spectrum tuning of the laser beam pulse. The pulse shaper is used to prevent three-photon and higher order nonlinear optical processes such as continuum generation. Higher order processes usually lead to sample degradation, and in the case of living samples to DNA damage. Suppression of three-photon transitions of four orders of magnitude has been achieved using the MII and BPS methods and this suppression can be coupled with optimization of two-photon signal from living specimens.

Figure 10:
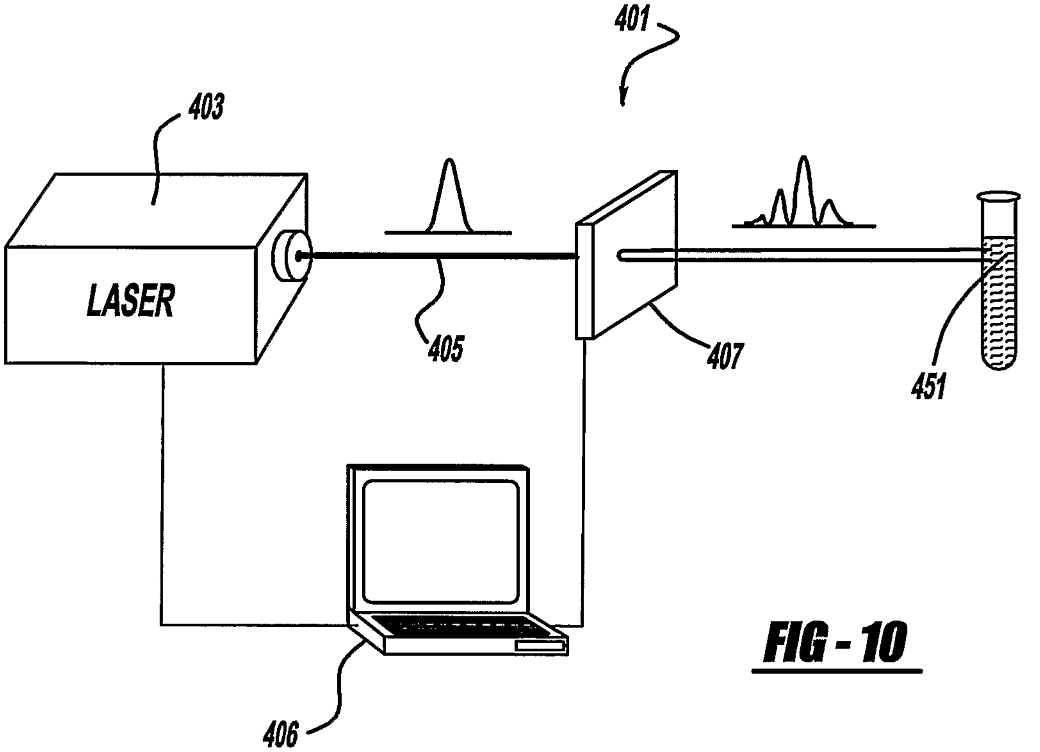
FIG. 10 is a diagrammatic, perspective view showing a third alternate embodiment of the present invention system applied to blood impurity identification.

Finally, reference should be made to FIG. 10. The alternate embodiment system 401' shown includes a laser 403, pulse shaper 407 and computer controller 406 like the prior PDT embodiment. The shaped laser beam pulse, however, targets blood 451 so the computer controller can automatically identify impurities therein. Such impure molecules may include hepatitis, HIV or other undesired contaminants. The system may then be used to destroy or sterilize the blood by ionizing such contaminants with one or a series of shaped fs laser beam pulses.

While various embodiments have been disclosed herein, it should be appreciated that other modifications may be made that are covered by the system and methods of the present invention. For example, alternate lasers, chemicals, optics, computer controllers and remote devices can be employed as long as they function as described. The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A system comprising:

(a) a laser operable to emit a first laser pulse having a duration equal to or less than 20 femtoseconds;

(b) a programmed controller;

(c) a pulse shaper controlled by the controller to correct phase distortions in a path of the pulse and optimized to cause selective stimulated Raman scattering at a specific molecular bond frequency and not at other undesired frequencies, the pulse shaper being operable to control a phase of the pulse;

(d) a second narrower-bandwidth pulse detuned from the first pulse carrying a probe photon, the second pulse being delayed from the first pulse by less than about 10 picoseconds;

(e) a telescope focusing at least one of the pulses at a specimen; and (f) a detector operable to detect both coherent and spontaneous Raman characteristics of the specimen caused by at least one of the pulses striking the specimen, the laser and detector being remotely located at least 10 meters away from the specimen during the emission and detection.

2. The system of claim 1 wherein the second pulse operably heterodynes an emission from the specimen, caused by the first pulse, to the detector.

3. The system of claim 1 wherein the pulse shaper employs spectral phase functions with translational symmetry of pseudorandom binary series.

4. The system of claim 1 further comprising a controller automatically identifying an unknown specimen receiving the pulses based on a database containing information used for discrimination.

5. The system of claim 4 wherein the controller follows a protocol of different pulse sequences and records the corresponding detected outcomes then computes the probability of having identified the specimen based on the database.

6. The system of claim 4 wherein the specimen includes a biological pathogen.

7. The system of claim 4 wherein the specimen includes a harmful chemical molecule in a complex chemical environment.

8. The system of claim 1 further comprising a remote aerospace craft, the laser and shaper being attached to the craft and the craft operably emitting the laser beam pulses, the shaper continuously correcting the dispersion acquired in the beam path by propagation of the pulse during use.

9. The system of claim 1 further comprising multiphoton intrapulse interference created by the shaper acting upon the first pulse.

10. The system of claim 1 further comprising a controller, the detector being connected to the controller, and the controller automatically varying a sampling rate of the detector depending upon its identification results.

11. The system of claim 1 wherein both of the pulses are in the near-infrared to infrared.

12. The system of claim 1 further comprising a beam splitter, mirrors and the telescope used to direct and focus at least one of the pulses.

13. The system of claim 1, wherein the laser includes an optical parametric amplifier to generate the laser beam which includes a broad bandwidth pulse.

14. The system of claim 1 wherein the laser is a Ytterbium fiber laser.

15. The system of claim 1 wherein the controller causes the system to automatically sample air at the specimen multiple times per second.

16. The system of claim 1 wherein the same telescope also collects the sensed Raman characteristic using a confocal arrangement.

17. The system of claim 1 further comprising a second telescope located in a detection path and the first telescope being in an excitation path.

18. The system of claim 1 further comprising a library of pulse shapes accessed by the controller for use by the pulse shaper, the library being field updatable.

19. The system of claim 1 wherein the specimen is an explosive located in a chemically complex background.

20. The system of claim 1 wherein the laser has a pulse intensity of at least 1 micro-Joule.

21. A system comprising:

a first laser beam pulse equal to or less than 20 femtosecond duration and at least 1 micro-Joule intensity, including at least one of: (i) a pump photon and (ii) a Stokes photon;

a second laser beam pulse having a narrower bandwidth and different color than the first pulse, the first pulse carrying a spectral phase function optimized to selectively excite a molecular bond frequency of an explosive specimen, and the second pulse being delayed in emission from the first pulse and further being operable to heterodyne the emitted signal;

a spectrometer detector;

the second pulse operably carrying an emission from the explosive specimen, caused by the first pulse, to the detector;

a pulse shaper operably varying a shape of at least one of the pulses in response to computer control of the shaper, and a moveable remote location spaced at least 0.5 meter from the explosive specimen, the laser beam pulses being emitted from the moveable remote location, and the spectrometer moving with the moveable remote location during its sensing of the emission;

wherein the detector collects both coherent and spontaneous Raman emissions from the specimen; and further comprising a telescope through which at least one of the pulses is transmitted, the specimen being at least 10 meters away from the a laser, the telescope, the shaper and the telescope during pulse emission and spectrometer detection.

22. The system of claim 21 further comprising telescope optics mounted to the moveable remote location which is a flying aerospace craft, the laser and shaper being attached to the craft and the craft operably emitting the laser beam pulses, the shaper correcting phase distortions in the laser and the telescope optics and actively correcting group velocity dispersion introduced by the rapidly varying beam path.

23. The system of claim 21 further comprising a controller automatically identifying an unknown specimen receiving the pulses, the controller being located in the moveable remote location.

24. The system of claim 21 wherein the specimen is located in a complex chemical environment.

25. The system of claim 21 wherein at least one of the pulses is infrared.

26. The system of claim 21 wherein the detector is connected to the computer, the computer automatically varies a sampling rate of the detector depending upon its identification results, the detector samples and the computer identifies the results multiple times per second.

27. An environmental monitoring system comprising:

a femtosecond laser operable to emit a laser beam of less than about 51 femtosecond pulse duration upon a specimen;

a pulse shaper operable to shape the laser beam pulse;

a telescope operably focusing the shaped pulse at the specimen;

a detector, remotely located at least 10 meters away from the specimen, operably sensing both coherent and spontaneous Ramon active characteristics of the specimen after activation by the laser beam; and a computer automatically varying pulse shaping performance of the pulse shaper for subsequent laser beam emissions, the computer operably identifying Raman active vibration characteristics of the specimen, the computer automatically identifying if the specimen is an explosive from an otherwise chemically complex background in a calculated manner with the assistance of the coherent and spontaneous Raman characteristics and free of inversion procedures.

28. The system of claim 27 wherein the femtosecond laser operably creates a laser beam pulse of less than 21 femtosecond duration and at least 1 micro-Joule intensity.

29. The system of claim 27 wherein the laser is a fiber laser, and the computer automatically identifies the specimen in an outdoor environment by comparing the detected Raman characteristics against pre-stored data which can be updated in the field.

30. The system of claim 27 further comprising multiphoton intrapulse interference used by the shaper for at least one of pulse characterization and compensation.

31. The system of claim 27 wherein the computer automatically determines if a biological pathogen is present in the specimen.

32. The system of claim 27, wherein the laser includes an optical parametric amplifier to generate the laser beam which includes a broad bandwidth pulse.

33. The system of claim 27 wherein the laser is a Ytterbium fiber laser.

34. The system of claim 27 further comprising a library of pulse shapes accessed by the computer for use by the pulse shaper, the library being field updatable.

35. The system of claim 27 wherein the laser and detector are located in an aerospace craft.

36. The system of claim 27 wherein the computer causes the system to automatically sample air at the specimen at least once per minute.

37. The system of claim 27 wherein the computer causes the system to automatically sample air at the specimen multiple times per second.

38. The system of claim 27 wherein the same telescope also collects the sensed Raman characteristic using a confocal arrangement.

39. The system of claim 27, further comprising a second telescope located in a detection path and the first telescope located in an excitation path.

40. A method of monitoring an area, the method comprising:

(a) emitting automatically varying shaped laser pulses through a telescope, at a specimen outside of a laboratory, at least one of the laser pulses having a duration equal to or less than 20 femtoseconds and an intensity of at least 0.7 mJ;

(b) automatically comparing Raman active data detected at least in part by step (a) with Raman active data of acceptable background molecules;

(c) automatically identifying harmful molecules based, at least in part, on the Raman active data comparisons;

(d) controlling multiphoton intrapulse interference in the shaped pulses sent through the telescope;

(e) automatically controlling and operating the emitting, analyzing, comparing and identifying steps by a computer at a remote location at least 10 meters away from the specimen within three shaped pulse emissions at the specimen, and (f) emitting the pulses and detecting the Raman active data at least 10 meters away from the specimen; and (g) detecting both coherent and spontaneous Raman emissions from the specimen.

41. The method of claim 40, further comprising monitoring the area in repetitive intervals of about one minute or less for a nominal condition.

42. The method of claim 41 further comprising monitoring the area in repetitive intervals of at least 1000 times per minute if suspicious molecules are identified.

43. The method of claim 40 further comprising moving a laser relative to the specimen while the laser is emitting the pulses.

44. The method of claim 40 further comprising controlling nonlinear optical processes induced by the laser pulses in a calculated manner without inversion procedures, and the telescope focusing the shaped pulses at the specimen.

45. The method of claim 40 wherein the computer uses both of the coherent and spontaneous Raman emissions from the specimen to identify the specimen.

46. The method of claim 40 further comprising using the computer to determine if the specimen is an explosive in complex chemical environment.

47. The method of claim 40 further comprising obtaining a detection signal only within a confocal region near a focus of a laser.

48. The method of claim 40 further comprising using the multiphoton intrapulse interference to achieve selective excitation of at least one vibrational frequency of the specimen.

49. A system comprising:

a) a fiber laser emitting laser pulses each having a duration equal to or less than 20 femtoseconds, and an intensity of at least 1 micro-Joule, in an outside environment;

b) a programmed controller, including a library of acceptable background data, unacceptable chemical data, and pulse shaping control data;

c) a pulse shaper controlled by the controller to correct phase distortions and cause selective Raman activation, without inversion procedures;

d) a telescope focusing the laser pulses on a remote location at least 0.5 meter away; and e) a spectrometer detecting both coherent and spontaneous Raman characteristics which are sent to the controller for identification using the library.

50. The system of claim 49 wherein the laser is a Ytterbium fiber laser.

51. The system of claim 49 wherein the laser, shaper, telescope and spectrometer are all remotely located away from and capable of moving relative to an explosive specimen during the laser pulse emissions and Raman detection.

52. The system of claim 49 wherein the detection and identification occurs in repetitive intervals of about one minute or less.

* * * * *